(12) United States Patent
Jonczyk et al.

(10) Patent No.: US 8,815,893 B2
(45) Date of Patent: Aug. 26, 2014

(54) HETARYLAMINONAPHTHYRIDINES

(75) Inventors: Alfred Jonczyk, Darmstadt (DE); Dieter Dorsch, Ober-Ramstadt (DE); Frank Zenke, Darmstadt (DE); Christiane Amendt, Muehltal/Trautheim (DE)

(73) Assignee: Merck Patent GmbH, Darmstadt (DE)

( * ) Notice: Subject to any disclaimer, the term of this patent is extended or adjusted under 35 U.S.C. 154(b) by 36 days.

(21) Appl. No.: 13/580,277

(22) PCT Filed: Jan. 10, 2011

(86) PCT No.: PCT/EP2011/000054
§ 371 (c)(1),
(2), (4) Date: Aug. 21, 2012

(87) PCT Pub. No.: WO2011/101069
PCT Pub. Date: Aug. 25, 2011

(65) Prior Publication Data
US 2012/0316166 A1    Dec. 13, 2012

(30) Foreign Application Priority Data
Feb. 22, 2010    (EP) .................................... 10001758

(51) Int. Cl.
*C07D 215/38*    (2006.01)
*A61K 31/04*    (2006.01)

(52) U.S. Cl.
USPC .......................................... 514/300; 546/122

(58) Field of Classification Search
USPC .......................................... 546/122; 514/300
See application file for complete search history.

(56) References Cited

U.S. PATENT DOCUMENTS

| | | | |
|---|---|---|---|
| 7,446,112 B2 | 11/2008 | Grootenhuis et al. | |
| 8,614,226 B2 * | 12/2013 | Jonczyk et al. | 514/300 |
| 2005/0171141 A1 | 8/2005 | Grootenhuis et al. | |
| 2005/0245508 A1 | 11/2005 | Weller et al. | |
| 2008/0107623 A1 | 5/2008 | D'Andrea et al. | |
| 2009/0042928 A1 | 2/2009 | Grootenhuis et al. | |
| 2010/0331293 A1 * | 12/2010 | Cushing et al. | 514/210.02 |

FOREIGN PATENT DOCUMENTS

| | | | |
|---|---|---|---|
| WO | WO 2005/056552 A1 | | 6/2005 |
| WO | WO 2005/065691 A1 | | 7/2005 |
| WO | WO2010/151791 | * | 12/2010 |
| WO | WO 2010/151791 A1 | | 12/2010 |

OTHER PUBLICATIONS

International Search Report of PCT/EP2011/000054.
P.L. Ferrarini et al., "Study on Affinity Profile Toward Native Human and Bovine Adenosine Receptors of a Series of 1,8-Naphthyridine Derivatives", Journal of Medicinal Chemistry, vol. 47, No. 12 (Jan. 1, 2004) pp. 3019-3031.
G. Abbiati et al., "An Efficient Synthesis of 2,4-Substituted [1,8]Naphthyridines from 3-(2-Amino-5-methylpyridin-3-yl)-1-arylprop-2-yn-1-ones", Synthesis, No. 13 (Jan. 1, 2002) pp. 1912-1916.
G. Abbiati et al., "Palladium-Assisted Multicomponent Synthesis of 2-Aryl-4-aminoquinolines and 2-Aryl-4-amino[1,8]naphthyridines", Journal of Organic Chemistry, vol. 70, No. 16 (2005) pp. 6454-6460.

* cited by examiner

*Primary Examiner* — D M Seaman
(74) *Attorney, Agent, or Firm* — Millen, White, Zelano & Branigan, P.C.

(57) ABSTRACT

Novel hetarylaminonaphthyridine derivatives of formula (I)

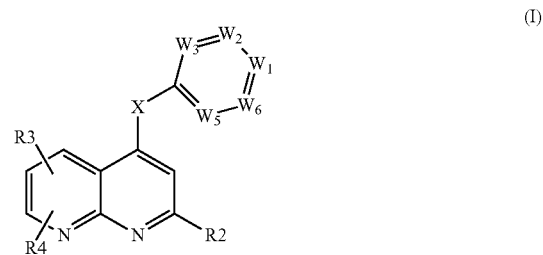

wherein X, R1, R2, R3, R4, W1, W2, W3, W5 and W6 have the meaning according to claim 1, are inhibitors of ATP consuming proteins, and can be employed, inter alia, for the treatment of tumors.

20 Claims, No Drawings

HETARYLAMINONAPHTHYRIDINES

The present invention relates to compounds and to the use of compounds in which the inhibition, regulation and/or modulation of signal transduction by ATP consuming proteins like kinases plays a role, particularly to inhibitors of TGF-beta receptor kinases. Objects of the invention are also pharmaceutical compositions that comprise these compounds, and to the use of the compounds for the treatment of kinase-induced diseases.

Proteins which bind ATP and utilize its energy to change conformation, to phosphorylate substrates, and to initiate signaling cascades are known from many classes, like kinases, phosphatases, chaperones or isomerases. With specific tools and techniques ATP-binding proteins can be enriched.

From the large family of protein kinases, split into subfamilies of tyrosine kinases and serine threonine kinases, a partial list includes cAbl, Akt, ALK, ALK1 and its family members like ALK1 and ALK5, Axl, Aurora A and B, Btk, Dyrk2, EGFR, Erk, Ephrin receptors like EphA2, FAK, FGF receptors like FGFR3, insulin receptor IR and insulin like growth factor receptor IGF1R, IKK2, Jak2, JNK3, cKit, LimK, VEGF receptors 1, 2, and 3, Meki, Met, P70s6K, PDGFR, PDK1, PI3K, Plk1, PKD1, bRaf, RSK1, Src and its family members, TAK1, Trk A, B, C, Zap70. The different kinases can be described under several synonyms, well known to the one skilled in the art and accessible in data bases like Kinweb to find a gene and protein report with alternative names, classification, gene annotation, sequence and gene structure, and links to the pdb 3D structure information. Similarly, proteomics server will give access to a lot of information and analysis and prediction tools for genes and proteins, including kinases.

As a mechanistic part of the hallmarks of cancer, Ser/Thr kinases and receptor tyrosine kinases (RTK) are phosphorylating enzymes essential in cellular signaling. Cell cycle, survival, proliferation and cell death are cellular processes, regulated by cell signaling, to permit tissue to grow, to regenerate and to be in homeostasis, or to regress. Some kinases are therefore exquisite targets for mammalian therapy.

Of the different families of kinases, which are part of the human kinome the receptor tyrosine kinase KDR, also called VEGF receptor 2, can stimulate endothelial cell survival and proliferation if ligated extra cellular by VEGF. Ligand binding can then lead to intracellular phosphorylation events, a signaling cascade and ultimately to proliferation.

Inhibition of this KDR signaling is attempted by various therapies. Other kinases and ligands important for function of endothelial cells are TIE2 kinase and the angiopoietins, PDGF receptor and PDGF as well as PlGF. Ephrin receptor kinase and ephrins, especially EphB4 and ephrin-B2. In addition, the ligand TGFβ and its receptors TGFβR, i.e. Alk1/Alk5, play an important role in maintenance of vascular integrity. By binding to the TGFβ type II receptor TGFβ can activate 2 distinct type I receptors in endothelial cells, i.e. the EC-restricted ALK1 and the broadly expressed ALK5 with opposite effects on EC behavior. ALK1 stimulates EC proliferation and migration via Smad1/5 transcription factors, ALK5 inhibits those functions via Smad2/3 transcription factors. One example for an Alk5 kinase inhibitor that facilitates EC proliferation and sheet formation is SB-431542. Ligand binding inhibition might be an additional approach to modulate TGFβ receptor signaling also in angiogenesis. This was shown with 2 peptides and also discussed for soluble TGFβ receptor sTβR-Fc. Use of anti-TGFβ antibodies, even a TGFβ trap, would be another strategy to inhibit TGFβ signaling.

The TGFβ proteins comprise a family of conserved dimeric proteins with a molecular weight of ~25 kDa, which are ubiquitously expressed and secreted in an inactive form. Local proteolysis in response to appropriate stimuli leads to active TGFβ ligands. TGFβ signaling is implicated in numerous conditions and diseases, including cancer, cardiovascular, bone, CNS, PNS, inflammatory and neurodegenerative disorders.

In epithelial cells, TGFβ inhibits cell proliferation. The transition of normal epithelial cell into carcinoma cells is accompanied by down-regulation of the growth-inhibition response to TGFβ, allowing the cells to escape the autocrine tumor suppressor activities of TGFβ signaling. The increased production of TGFβ by carcinoma cells contributes to the invasive and metastatic behavior of the cancer cells. TGFβ can induce an epithelial-to-mesenchymal transition (EMT) that allows the cells to become invasive and migratory. In addition, the increased TGFβ production exerts effects on stromal and immune cells to provide a favorable microenvironment for cancer progression. TGFβ proteins signal through TβR-I/II receptor kinases and their Smad substrates, but can also signal independent of Smads, such as ERK MAP kinases, PI3 kinase, Rho-like GTPases, protein phosphatase 2A, and Par6. Activated type I TβR kinases enhance survival of cells and can accelerate pathological cell progression. TGFβ receptor type I and II (TβR I, TβR II) are single-pass transmembrane-spanning intracellular serine/threonine kinases presenting extracellular ligand (TGFβ) binding receptors. Intra-cellular signaling proceeds via auto-phosphorylation, trans-phosphorylation and substrate phosphorylation, leading to modulation of target gene expression. Cloning and genomic organization of TβR proteins is well-known. TβR sequences are deposited in www.uniprot.org as TGFR1_human with accession number P36897, and as TGFβR2_human with accession number P37173. On protein level, type I TβR is described to contain a region rich in Gly and Ser (GS domain) preceding the receptor kinase domain. TβR II is in its auto/phosphorylated state a constitutively active kinase which binds to the type I receptor and phosphorylates it in the GS domain.

TβReceptor, a ligand TGFβ-bound (activated) tetrameric complex of 2 TβR I and 2 TβR II units, is able to phosphorylate Smads (Smad 2 and Smad 3) in their C-terminal SSXS motifs as substrates which in turn are bound to/by Smad4 to be translocated to the cell nucleus, where they modulate TGFβ responsive genes. The different domains which regulate homomeric and heteromeric complex formation among type I and type II TβRs are known. Mutations in the GS domain of TβR I can be constitutively activating. Kinase inactivating mutation were found with K232R for type I and K277R for type II TβR. Inactivating or attenuating mutations in the genes for Type I and Type II TβR genes are found in a variety of cancers. In addition, signaling of TβRs is regulated by phosphorylation and dephosphorylation mechanisms, ubiquitinylation and sumoylation, and by endocytosis and by TACE-mediated ectodomain shedding of type I, but not type II receptors TACE, aka ADAM-17, which mediates shedding of cytokines, GF receptors, and adhesion proteins and is highly expressed in cancers.

The X-ray co-crystal structure of TβR I and FKBP12 has been described, and the kinase activation process was discussed. Meanwhile, several crystal structures can be found in the PDB data base: 1B6C, 1IAS, 1PY5, 1RW8, 1VJY, 2PJY, and a model 1TBI. For TβR II only X-ray studies for the extracellular ligand binding domain are known to the public: 1KTZ, 1M9Z, and 1PLO (NMR), but none of the kinase domain.

TGFβ signal transduction involves Smads, the only substrates for TβR type I receptor kinases. The human genome encodes eight Smads from 3 subfamilies (R-, Co-, I-Smads), which are ubiquitously expressed throughout development and in adult tissue. Smads not only are phosphorylated by Type I TGFβ receptor kinases but they are also regulated by oligomerization, ubiquitinylation and degradation, and nucleoplasmatic shuttling.

It was shown that VEGF release is regulated by ALK1 and ALK5, whereas TGFβ enhanced and BMP-9 suppressed expression of VEGF.

Studies with truncated ALK4 isoforms suggest involvement of this type I kinase in growth and development of pituitary tumors, by a dominant negative inhibition of activin signaling. Studies of the spatiotemporal window of roles of ALK4 in embryonic development, regulation of the mesoderm induction, primitive streak formation, gastrulation, primary axis formation and left-right axis determination are still not clarifying the role of ALK4 in adult. In a large scale human candidate screen it was found that dominant-negative ALK2 alleles are associated with congenital heart disease, like improper atrioventrikular septum development.

ALK1 binds TβR-II and Endoglin/CD105/TβR-III and phosphorylates SMAD-1 and -5. The role of endoglin and especially the differential modulation of TGFβ signaling by two variants, L- and S-endoglin, have been shown. ALK1 functions in vascular remodeling and is found with ALK5 in balancing the activation state of endothelium in inflamed tissue, wounds and tumor. ALK1 is expressed in lung, placenta, and other highly vascularized tissue, and is selectively found on ECs. In addition, ALK1 was detected on neurons.

Loss of expression of type II TβR correlates with high tumor grade in human breast carcinomas, indicating a contribution to beast cancer progression. Tumor growth can be characterized by deregulated i.e. autonomous cell growth due to perturbation of RTK signaling by mutations or other genetic alterations. Of the 32000 human coding genes which are involved in signal transduction, more than 520 protein kinases and 130 protein phosphatases exert tight and reversible control on protein phosphorylation. Selectivity is found for tyrosine and for serine/threonine phosphorylation. There are more than 90 known PTK genes in the human genome, more than 50 encode transmembrane RPTKs distributed in 20 subfamilies, and 32 encode cytoplasmic, non-receptor PTKs in 10 subfamilies. For example Trk A has an important role in thyroid carcinomas and neuroblastomas, EphB2 and B4 are over-expressed in carcinomas, Axl and Lck are over-expressed in leukemia.

TGFβ inhibitors for the treatment of cancer were reviewed. There are further indications and pathologies, indirect targeting cancer, wound healing and inflammation via anti-angiogenesis, blood vessel formation, stabilization, maintenance and regression. Angiogenesis, the development of new vessels from pre-existing vessels, is critical in vascular development in embryogenesis, organogenesis, and wound healing. In addition to those physiological processes, angiogenesis is important for tumor growth, metastasis and inflammation, resulting in diseases like tumors of the breast, uterine cervix, uterine corpus (endometrium), ovary, lung, bronchus, liver, kidney, skin, oral cavity and pharynx, prostate, pancreas, urinary bladder, blood cells, colon, rectum, bone, brain, central and peripheral nervous system, exemplified as breast cancer, colorectal cancer, gliomas, lymphomas, and so on, and of inflammatory diseases like rheumatoid arthritis and psoriasis, or diseases of the eye, like macula degeneration, and diabetic retinopathy. Molecular mechanisms of blood vessel formation and the angiogenic switch in tumorigenesis were recently discussed. Vascular patterning is regulated by Eph receptor tyrosine kinases and ephrin ligands, e.g. ephrin-B2 signaling via Eph B4 and Eph B1. EphB4 controls vascular morphogenesis during postnatal angiogenesis. The maturation of nascent vasculature, formed by angiogenesis or vasculogenesis, requires mural cells (pericytes, smooth muscle cells), generation of extracellular matrix and specialization of the vessel wall for structural support and regulation of vessel function. Regulation of those processes and interaction between endothelial cells and their mural cells involves several ligand kinase pairs, like VEGF/VEGFR1, VEGFR2, EphrinB2/EphB4, PDGFR/PDGFRB, Angiopoietins/TIE2, TGFβ/TGFβR-ALK1/ALK5. Vessel assembly, capillary formation, sprouting, stabilization and destabilization, even regression, is regulated by a functional balance of those kinases and ligands. Lymphangiogenesis is regulated via VEGF receptor 3 and its ligands VEGF C, and D, as well as TIE2 and its ligands angiopoietins 1, 2. Inhibition of VEGFR3 and/or TIE2 signaling and therefore inhibition of formation of lymphatic vessels can be a mean to stop metastasis of tumor cells. The whole body of information about pathological vascularization leads to the assumption for inhibition of angiogenesis being a promising strategy for treatment of cancer and other disorders.

The importance of TGFβ receptors for angiogenic processes is shown by Alk1, endoglin, Alk5 and TβRII KO mice all exhibiting an embryonic lethal phenotype due to vascular defects. In addition, in ECs TGFβ ligands are able to stimulate two pathways, with Smad 1/5/8 phosphorylation downstream of Alk1 and Smad2/3 phosphorylation downstream of Alk5. Both pathways cross-talk with each other. Alk5 knock-in mice with L45 loop mutations show defective Smad activation. TGFβ/Alk5 signaling is antagonized by ALK1 in ECs.

TGFβ exists in at least five isoforms (TGFβ1-5), which are not related to TGFa, with TGFβ1 as the prevalent form. TGFβ is a ubiquitous and essential regulator of cellular and physiological processes including proliferation, differentiation, migration, cell survival, angiogenesis and immunosurveillance. Since cancer cells express tumor-specific antigens they normally would be recognized by the immune system and would be destroyed. During tumorigenesis cancer cells acquire the ability to evade this immunosurveillance by multiple mechanisms. A major mechanism is cancer cell mediated immunosuppression by secretion of TGFβ, a potent immunosuppressive cytokine. TGFβ has the potential to switch from being a tumor suppressor to a tumor promoter and prometastatic factor.

TGFβ function is transmitted by a tetrameric receptor complex, consisting of two groups of transmembrane serine-threonine kinase receptors, called type I and type II receptors, which are activated following engagement of members of the TGFβ superfamily of ligands, which is divided in 2 groups, the TGFβ/Activin and BMP/GDF branches. TGFβ1, 2, and 3 belong to the TGFβ/Activin branch of ligands. These binding events specify downstream responses that are differentially regulated in different cell types.

Importance of fibroblasts in mesenchymal-epithelial interaction in skin during wound repair was described in an inducible postnatal deletion of TGFβ RII in skin fibroblasts. During wound repair, expression of the ligand TGFβ and its receptor types RI and RII are timely and spatially regulated. CD109, a GPI linked cell surface antigen, expressed by CD34+ acute myeloid leukemia cell lines, ECs, activated platelets and T-cells are part of the TβR system in human keratinocytes. Follicle Stem Cells (FSCs) in the bulge region of hair follicle can give rise to multiple lineages during hair cycle and wound healing. Smad4, a common mediator of TGFβ signaling is part of FSCs maintenance. Smad4 KO studies in mouse skin showed hair follicle defects and squamous cell carcinoma formation. The potential suppression of TGFβ delayed catagen progression in hair follicles. The well described role of TGFβ in keratinocyte apoptosis during catagen phase is likely to involve anagen-specific hair follicle components also involving co-localized TβRI and TβRII.

Abnormal activity of TGFβ in fibrosis of several organs, such as skin, kidney, heart and liver, is known, being a rational for use of TβR inhibitors in fibrotic diseases. Systemic sclerosis (scleroderma), a complex disorder of connective tissue leading to fibrosis of the skin and inner organs, was shown to be TGFβ/receptor RI dependent. Pulmonary arterial hypertension (PAH) is a condition potentially treatable with ALK5 inhibitors because abnormal proliferation of peripheral arterial smooth muscle cells is driven by activated TGFβ receptors. Treatment in rats was successful with SB525334. Benefit in rat was also shown with IN-1233. Renal fibrosis can lead to diabetes.

Beneficial side effects of TβR kinase inhibitor derivatives and a connection between TGFβ signaling and hepatitis C virus (HCV) replication is known. TGFβ signaling is discussed as an emerging stem cell target in metastatic breast cancer. TGFβ1, 2, 3 and their receptors are expressed in neurons, astrocytes and microglia. Improvement of pathological outcome with TGFβ signaling modulators can be expected. The TGFβ superfamily in cardiovascular disease, like atherosclerosis, myocardial ischemia and cardiac remodeling is focus of an issue of cardiovascular research.

Further details on the biochemistry of TGFβ are disclosed in WO 2009/004753, which is incorporated in its entirety by reference in the disclosure of the invention hereby.

Several TGF-beta receptor kinase inhibitors (TβR inhibitors) and compounds series are described to the public from non-clinical studies and several inhibitors are known by code in public domain. In particular, several new chemical entities are known from patent literature, in which they are claimed to be inhibitors of TGFβ receptor kinases. WO 2009/133070 describes imidazopyridines, WO 2009/124653 teaches thienopyrimidines, WO 2009/087225 concerns pyrrolopyridines/pyrimidines and WO 2009/049743 relates to thienopyridines. None of the references is directed to the synthesis and use of compounds of formula (I) as described below.

The invention had the object of finding novel compounds having valuable properties, in particular those which can be used for the preparation of medicaments.

It has been surprisingly found that the compounds according to the invention and salts thereof have very valuable pharmacological properties while being well tolerated. In particular, they exhibit TGF-β receptor I kinase-inhibiting properties. The invention relates to compounds of formula (I)

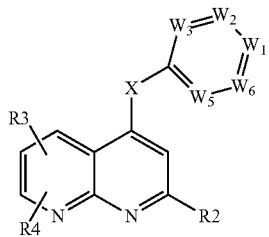

(I)

wherein
W1, W5, W6 denotes independently from one another N or CH;
W2 denotes N or CR6;
W3 denotes N or CR5;
under the proviso that at least one of W1, W2, W3, W5 or W6 denotes N;
X denotes NR1, Alk, O, S or C=R1;
R1 denotes H, A or Cyc;
R5 denotes H, A, Hal, OY, CN, -Alk-OY, COOY, —CO—NYY, SA, $SO_2A$, NYY, —OAlk-OY, —OAlk-NYY, —OAlk-NY—COOY, —OAlk-$Het^3$, $NO_2$, —NH-Alk-COOY, —NH—CO-Alk-OY, —NH—CO-Alk-OCOY, —NH—CO-Alk-NYY, —NH—CO—NYY, —NH—CO-$Het^3$, —NY—COOY, —NY—$SO_2$Y, —NH—$SO_2$—NYY, —NH-$Het^2$, —NH—R2, —NY—CO—R2, —NY—CO—NY—R2, —NY—COO—R2, —NY—$SO_2$—R2, —NY—$SO_2$—NY—R2, —OAr, —NY—Ar, —O$Het^1$, NY-$Het^1$, —CO—NYY—NYY, —CO-$Het^3$ or —CO—NH-Alk-$Het^3$;
R1, R5 together also denote —CH=CH—, —C(Y)=N—, —N=C(Y)—, —C(COY)=N—, —C(CO—R2)=N—, —CO—NH—, —NH—CO—, —$SO_2$—NH—, —NH—$SO_2$—, =CH—NH—CO—, —CH—N(Alk-$Het^3$)—CO—, —CH=C($NO_2$)— or —CH=C(Hal)-;
R6 denotes H, A, Hal, OY, CN, -Alk-OY, COOY, —CO—NYY, NYY, —NY—COOY, —NH-Alk-NYY, —NH—COA, —NH—CO-Alk-NYY, —NH-$Het^2$, $Het^3$, —OAr, —NY—Ar, —O$Het^1$, NY-$Het^1$, $Het^1$, —NH—$SO_2$Y, —NH-Cyc, —NH-$Het^3$, —NH-Alk-$Het^3$, —NH-Alk-OY, —NH—CO—NYY, —NH—CO-$Het^3$, —CO—NH-$Het^3$, —NH—CO-Alk-OY, —NH—CO-Alk-$Het^3$, —CO—NH-Alk-$Het^3$, —NH—CO-Alk-NH—COOY or —CO—NH-Alk-NYY;
R2 denotes a monocyclic carboaryl having 5-8 C atoms or a monocyclic heteroaryl having 2-7 C atoms and 1-4 N, O and/or S atoms,
each of which can be substituted by at least one substituent selected from the group of A, Hal, CN, NYY, OY, =O;
R3, R4 denotes independently from one another H, A, Hal, CN, NYY, OY, —OAlk-NYY, —OAlk-OY;
Y denotes H or A;
A denotes unbranched or branched alkyl having 1-10 C atoms,
in which 1-7 H atoms can be replaced by Hal;
Cyc denotes cycloalkyl having 3-7 C atoms,
in which 1-4 H atoms can be replaced independently from one another by A, Hal and/or OY;
Alk denotes alkylene having 1-6 C atoms,
in which 1-4 H atoms can be replaced independently of one another by Hal and/or CN;
Ar denotes a saturated, unsaturated or aromatic, mono- or bicyclic carbocycle having 6-10 C atoms,
which can be substituted by at least one substituent selected from the group of $Het^3$, A, Hal, OY, COOY, -Alk-OY, -Alk-$SO_2$, -Alk-$Het^1$, —OAlk-$Het^1$, NYY, —CO—NYY, —$SO_2$NYY, CN;
$Het^1$ denotes a monocyclic heteroaryl having 2-7 C atoms and 1-4 N, O and/or S atoms,
which can be substituted by at least one substituent selected from the group of A, Hal, OY, COOY, -Alk-OY, -Alk-$SO_2$, NYY, —CO—NYY, —$SO_2$NYY, CN;
$Het^2$ denotes a bicyclic heteroaryl having 2-9 C atoms and 1-4 N atoms,
which can be substituted by at least one substituent selected from the group of R2, A, Hal, OY, COOY, -Alk-OY, -Alk-$SO_2$, NYY, —CO—NYY, —$SO_2$NYY, CN;
$Het^3$ denotes a saturated monocyclic heterocycle having 2-7 C atoms and 1-4 N, O and/or S atoms, which can be substituted by at least one substituent selected from the group of A, Hal, OY, COOY, -Alk-OY, -Alk-SO$_2$, NYY, —CO—NYY, —SO$_2$NYY, CN; and Hal denotes F, Cl, Br or I;

and/or physiologically acceptable salts thereof.

For the sake of clarity, R1; R5; R6; R1, R5 together have the indicated meaning under the proviso that (i) R1, R5 together are absent if R1 and R5 have the indicated meaning, and (ii) R1 and R5 are absent if R1, R5 together have the indicated meaning.

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The invention also comprises solvates of salts of the compounds according to the invention. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995). It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art and are described (e.g. Wermuth C G et al., Chapter 31: 671-696, The Practice of Medicinal Chemistry, Academic Press 1996; Bundgaard H, Design of Prodrugs, Elsevier 1985; Bundgaard H, Chapter 5: 131-191, A Textbook of Drug Design and Development, Harwood Academic Publishers 1991). Said references are incorporated herein by reference. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as "pure" E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or non-chiral phases or by recrystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The nomenclature as used herein for defining compounds, especially the compounds according to the invention, is in general based on the rules of the IUPAC-organization for chemical compounds and especially organic compounds. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent (e.g. YY) the expression of such substituent may differ from each other (e.g. methyl and ethyl). It shall be understood accordingly that a multiple substitution of any radical of the invention may involve identical or different radicals. Hence, if individual radicals occur a number of times within a compound, the radicals adopt the meanings indicated, independently of one another.

The terms "alkyl" or "A" refer to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In a preferred embodiment of the invention, "A" denotes unbranched or branched alkyl having 1-10 C atoms, in which 1-7 H atoms may be replaced by Hal. A more preferred "A" denotes unbranched or branched alkyl having 1-4 C atoms, in which 1-5 atoms may be replaced by F and/or Cl. Most preferred is $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It is a highly preferred embodiment of the invention that "A" denotes methyl. It shall be understood that the respective denotation of "A" is independently of one another in radicals R1 to R6, Y, Cyc, Ar, Het[1], Het[2] and Het[3].

The terms "cycloalkyl" or "cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In a preferred embodiment of the invention, "Cyc" denotes cycloalkyl having 3-7 C atoms, in which 1-4 H atoms may be replaced independently of one another by A, Hal and/or OY. More preferred is $C_5$-$C_7$-cycloalkyl, in which one H atom may be replaced by A, Hal, OH or OA. A highly preferred $C_5$-$C_7$-cycloalkyl radical is unsubstituted, i.e. cyclopentyl, cyclohexyl or cycloheptyl. Moreover, the definition of "A" shall also comprise cycloalkyls and it is to be applied mutatis mutandis to "Cyc".

The term "Alk" refers to unbranched or branched alkylene, alkenyl or alkynyl having 1, 2, 3, 4, 5 or 6 C atoms, i.e. $C_1$-$C_6$-alkylenes, $C_2$-$C_6$-alkenyls and $C_2$-$C_6$-alkynyls. Alkenyls have at least one C—C double bond and alkynyls at least one C—C triple bond. Alkynyls may additionally also have at least one C—C double bond. Example of suitable alkylene radicals are methylene, ethylene, propylene, butylene, pentylene, hexylene, isopropylene, isobutylene, sec-butylene, 1- 2- or 3-methylbutylene, 1,1-, 1,2- or 2,2-dimethylpropylene, 1-ethylpropylene, 1-, 2-, 3- or 4-methylpentylene, 1,1-, 1,2-, 1,3-, 2,2-, 2,3- or 3,3-dimethyl-butylene, 1- or 2-ethylbutylene, 1-ethyl-1-methylpropylene, 1-ethyl-2-methylpropylene, 1,1,2- or 1,2,2-trimethylpropylene. Example of suitable alkenyls are allyl, vinyl, propenyl (—$CH_2CH=CH_2$; —$CH=CH$—$CH_3$; —$C(=CH_2)$—$CH_3$), 1-, 2- or 3-butenyl, isobutenyl, 2-methyl-1- or 2-butenyl, 3-methyl-1-butenyl, 1,3-butadienyl, 2-methyl-1,3-butadienyl, 2,3-dimethyl-1,3-butadienyl, 1-, 2-, 3- or 4-pentenyl and hexenyl. Example of suitable alkynyls are ethynyl, propynyl (—$CH_2$—$C\equiv CH$; —$C\equiv C$—$CH_3$), 1-, 2- or 3-butynyl, pentynyl, hexynyl and or pent-3-en-1-in-yl, particularly propynyl.

In a preferred embodiment of the invention, "Alk" denotes unbranched or branched alkylene having 1-6 C atoms, in which 1-4 H atoms may be replaced independently of one another by Hal and/or CN. A more preferred "Alk" denotes unbranched alkylene having 1-6 C atoms, i.e. methylene, ethylene, propylene, butylene, pentylene or hexylene, in which 1-2 H atoms may be replaced by F and/or Cl. Most preferred is $C_{1-3}$-alkylene; particular examples of which are methylene, ethylene and propylene. It is a highly preferred embodiment of the invention that "Alk" denotes methylene or ethylene. It shall be understood that the respective denotation of "Alk" is independently of one another in the radicals R3 to R6, Ar, Het$^1$, Het$^2$ and Het$^3$.

The term "aryl" or "carboaryl" for the purposes of this invention refers to a mono- or polycyclic aromatic hydrocarbon systems having 3 to 14, preferably 4 to 10, more preferably 5 to 8 carbon atoms, which can be optionally substituted. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula (I) can be effected via any possible ring member of the aryl radical. Examples of suitable "aryl" radicals are phenyl, biphenyl, naphthyl, 1-naphthyl, 2-naphthyl and anthracenyl, but likewise in-danyl, indenyl or 1,2,3,4-tetrahydronaphthyl.

Preferred "carboaryls" of the invention are optionally substituted phenyl, naphthyl and biphenyl, more preferably optionally substituted monocyclic carboaryl having 5-8 C atoms, most preferably optionally substituted phenyl, highly preferably optionally substituted phenyl if defined in terms of R2 radical. The preferred carboaryls of the invention can be substituted by at least one substituent selected from the group of A, Hal, CN, NYY, OY, =O.

The term "heteroaryl" for the purposes of this invention refers to a 2-15, preferably 2-9, most preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, 3 or 4, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula (I) can be effected via any possible ring member of the heteroaryl radical. Examples of suitable "heteroaryl" are pyrrolyl, thienyl, furyl, imidazolyl, thiazolyl, isothiazolyl, oxazolyl, oxadiazolyl, isoxazolyl, pyrazolyl, pyridinyl, pyrimidinyl, pyridazinyl, pyrazinyl, indolyl, quinolinyl, isoquinolinyl, imidazolyl, triazolyl, triazinyl, tetrazolyl, phthalazinyl, indazolyl, indolizinyl, quinoxalinyl, quinazolinyl, pteridinyl, carbazolyl, phenazinyl, phenoxazinyl, phenothiazinyl and acridinyl.

It is preferred that "heteroaryl" in the realms of R2 radical represents a monocyclic heteroaryl having 2-7 C atoms and 1 to 4 N, O and/or S atoms, which can be substituted by at least one substituent selected from the group of A, Hal, CN, NYY, OY, =O. It is also preferred that "carboaryl" in the realms of R2 radical represents a monocyclic carboaryl having 5-8 C atoms, which can be monosubstituted by at least one substituent selected from the group of A, Hal, CN, NYY, OY, =O. Hence, the aforementioned heteroaryl and carboaryl shall represent the preferred Markush group for the radical R2.

In a more preferred embodiment of the invention, the R2 radical denotes phenyl or a monocyclic 5-6 membered heteroaryl having 1-3 N atoms, each of which can be substituted by at least one substituent selected from the group of Hal, A, NAA, CN, OA. Herein, particular preference is given to the heteroaryls thiophenyl, furanyl, thiazolyl, imidazolyl, pyridyl, pyrazinyl or pyrazolyl, each of which can be substituted as defined above. Subject to other substitutions, R2 denotes most preferably phenyl, pyridin-2-, 3-, 4- or 5-yl or pyrazolyl, each of which can be mono- di- or trisubstituted by at least one substituent selected from the group of F, Cl, Br, $CH_3$, $CF_3$, CN, $OCH_3$, $OCF_3$. It is highly preferred that R2 is phenyl, pyridin-2-yl, 2-fluoro-phenyl, 4-fluoro-phenyl, 2-fluoro-5-fluoro-phenyl, 2,4,5-trifluoro-phenyl, 2-fluoro-5-chloro-phenyl, 2-fluoro-5-bromo-phenyl, 2-fluoro-5-trifluoromethyl-phenyl, 2-fluoro-5-trifluoromethoxy-phenyl, 3-chloro-phenyl, 3-trifluoromethyl-phenyl, 6-methyl-pyridin-2-yl, pyrazol-4-yl, 1-methyl-pyrazol-3-yl, 3-methyl-pyrazol-1-yl.

It shall be understood that the respective denotation of "R2" is independently of one another in the radicals Het$^2$, R5 and R1, R5 together.

It is preferred that "heteroaryl" in the realms of "Het$^1$" represents a monocyclic heteroaryl having 2-7 C atoms and 1-4 N, S and/or O atoms, which can be substituted by at least one substituent selected from the group of A, Hal, OY, COOY, -Alk-OY, -Alk-SO$_2$, NYY, —CO—NYY, —SO$_2$NYY, CN. In a more preferred embodiment of the invention, Het$^1$ denotes a monocyclic heteroaryl having 2-7 C atoms and 1-4 N atoms, which can be substituted by —NH-Het$^3$, A and/or Hal. It shall be understood that the respective denotation of "Het$^1$" is independently of one another in the radicals R5 and R6.

It is preferred that "heteroaryl" in the realms of "Het$^2$" represents a bicyclic heteroaryl having 2-9 C atoms and 1-4 N atoms, which can be substituted by at least one substituent selected from the group of R2, A, Hal, OY, COOY, -Alk-OY, -Alk-SO$_2$, NYY, —CO—NYY, —SO$_2$NYY, CN. In a more preferred embodiment of the invention, Het$^2$ denotes a bicyclic heteroaryl having 2-9 C atoms and 1-4 N atoms, which can be substituted by R2, A and/or Hal. In a most preferred embodiment of the invention, Het$^2$ denotes 1,8-naphthyridine, which is monosubstituted by R2. A highly preferred embodiment of the Het$^2$ radical is 2-(2-fluoro-5-chloro-phenyl)-[1,8]naphthyridin-4-yl. It shall be understood that the respective denotation of "Het$^2$" is independently of one another in the radicals R5 and R6.

The terms "heterocycle" or "heterocyclyl" for the purposes of this invention refers to a mono- or polycyclic system of 3 to 20 ring atoms, preferably 3 to 14 ring atoms, more preferably 3 to 10 ring atoms, comprising carbon atoms and 1, 2, 3, 4 or 5 heteroatoms, which are identical or different, in particular nitrogen, oxygen and/or sulfur. The cyclic system may be saturated or mono- or poly-unsaturated. In the case of a cyclic system consisting of at least two rings the rings may be fused or spiro or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocyclyl radical. The bonding to the compounds of the general formula (I) can be effected via any possible ring member of the heterocyclyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

In an aspect of the invention, "Het$^3$" denotes a saturated monocyclic heterocycle having 2-7 C atoms and 1-4 N, O and/or S atoms, which can be substituted by at least one substituent selected from the group of A, Hal, OY, COOY, -Alk-OY, -Alk-SO$_2$, NYY, —CO—NYY, —SO$_2$NYY, CN. In a preferred embodiment of the invention, Het$^3$ denotes a saturated monocyclic heterocycle having 2-7 C atoms and 1-4 N, O and/or S atoms, which can be substituted by A, Hal, COOY and/or NYY. In a more preferred embodiment of the invention, Het$^3$ denotes piperazine, piperidine, morpholine, pyrrolidine, piperidone, morpholinone or pyrrolidone, which can be monosubstituted by A, Hal, COOY or NYY. In a most preferred embodiment of the invention, Het$^3$ denotes piperazine or morpholine, each of which can be monosubstituted by A. Highly preferred embodiments of the Het$^3$ radical are piperazine, which is monosubstituted by A, and unsubstituted morpholine. Herein, "A" is especially methyl, ethyl, propyl, butyl, pentyl, hexyl, isopropyl or trifluoromethyl, and Hal is especially F, Cl or Br. It shall be understood that the respective denotation of "Het$^3$" is independently of one another in the radicals R5, R6 and Ar.

In another embodiment of the invention, a "carbocycle", including, but not limited to, carboaryl, is defined as "Ar", which denotes a saturated, unsaturated or aromatic, mono- or bicyclic carbocycle having 3-10 C atoms, which can be mono-, di- or trisubstituted by at least one substituent selected from the group of Het$^3$, A, Hal, COOY, OY, -Alk-OY, -Alk-SO$_2$, -Alk-Het$^{1/2/3}$, —OAlk-Het$^{1/2/3}$, NYY, —CO—NYY, —SO$_2$—NYY, CN, -Alk-NYY. Examples of suitable "Ar" radicals are phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluoro-phenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethyl-sulfonamido)phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

In another preferred embodiment of the invention, the "Ar" radical denotes a saturated, unsaturated or aromatic, mono- or bicyclic carbocycle having 6-10 C atoms, which can be substituted by at least one substituent selected from the group of Het$^3$, A, Hal, OY, COOY, -Alk-OY, -Alk-SO$_2$, NYY, —CO—NYY, —SO$_2$NYY, CN. In a more preferred embodiment of the invention, Ar denotes a monocyclic carboaryl having 5-8 C atoms, which can be substituted by Hal. In a most preferred embodiment of the invention, Ar denotes phenyl, which can be monosubstituted by Hal. It shall be understood that the respective denotation of "Ar" is independently of one another in the radicals R5 and R6.

For the purposes of the present invention, the terms "alkylcycloalkyl", "cycloalkylalkyl", "alkylheterocyclyl", "heterocyclylalkyl", "alkylaryl", "arylalkyl", "alkylheteroaryl" and "heteroarylalkyl" mean that alkyl, cycloalkyl, heterocycl, aryl and heteroaryl are each as defined above, and the cycloalkyl, heterocyclyl, aryl or heteroaryl radical is bonded to the compounds of the general formula (I) via an alkyl radical, preferably C$_1$-C$_6$-alkyl radical, more preferably C$_1$-C$_4$-alkyl radical.

The term "alkyloxy" or "alkoxy" for the purposes of this invention refers to an alkyl radical according to above definition that is attached to an oxygen atom. The attachment to the compounds of the general formula (I) is via the oxygen atom. Examples are methoxy, ethoxy and n-propyloxy, propoxy and isopropoxy. Preferred is "C$_1$-C$_4$-alkyloxy" having the indicated number of carbon atoms.

The term "cycloalkyloxy" or "cycloalkoxy" for the purposes of this invention refers to a cycloalkyl radical according to above definition that is attached to an oxygen atom. The attachment to the compounds of the general formula (I) is via the oxygen atom. Examples are cyclopropyloxy, cyclobutyloxy, cyclopentyloxy, cyclohexyloxy and cycloheptyloxy. Preferred is "C$_3$-C$_7$-cycloalkyloxy" having the indicated number of carbon atoms.

The term "heterocyclyloxy" for the purposes of this invention refers to a heterocyclyl radical according to above definition that is attached to an oxygen atom. The attachment to the compounds of the general formula (I) is via the oxygen atom. Examples are pyrrolidinyloxy, thiapyrrolidinyloxy, piperidinyloxy and piperazinyloxy.

The term "aryloxy" for the purposes of this invention refers to an aryl radical according to above definition that is attached to an oxygen atom. The attachment to the compounds of the general formula (I) is via the oxygen atom. Examples are phenyloxy, 2-naphthyloxy, 1-naphthyloxy, biphenyloxy and indanyloxy. Preferred is phenyloxy.

The term "heteroaryloxy" for the purposes of this invention refers to a heteroaryl radical according to above definition that is attached to an oxygen atom. The attachment to the compounds of the general formula (I) is via the oxygen atom. Examples are pyrrolyloxy, thienyloxy, furyloxy, imidazolyloxy and thiazolyloxy.

The term "acyl" for the purposes of this invention refers to radicals that are formed by cleaving a hydroxyl group from acids. The attachment to the compounds of the general formula (I) is via the carbonyl C atom. Preferred examples are —CO-A, —SO$_2$-A and —PO(OA)$_2$, more preferably —SO$_2$A.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine and chlorine are more preferred, when the halogens are substituted on an alkyl (haloalkyl) or alkoxy group (e.g. CF$_3$ and CF$_3$O).

It is a preferred embodiment of the invention that the heteroaryl sub-structure

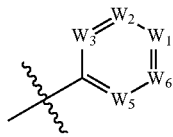

denotes pyridyl, pyrimidinyl, triazinyl, pyridazinyl or pyrazyl, each of which can be substituted by R5 and/or R6. Those skilled in the art know other N-heteroaryl rings can also be active in the meaning of the invention. It goes without saying that R5 is absent if W3 denotes N. For the sake of clarity, H is the substituent in position 1 if W1 is CH, R6 is the substituent in position 2 if W2 is CR6, R5 is the substituent in position 3 if W3 is CR5, H is the substituent in position 5 if W5 is CH, and H is the substituent in position 6 if W6 is CH.

The denotation of W1, W2, W3, W5 and W6 can be easily assigned by the skilled artisan to each N-heteroaryl in the meaning of the invention. In a particular embodiment of the invention, for example, W1 and W5 are independently from one another N or CH, W2 is CR6, W3 is N or CR5, and W6 is CH. In another particular embodiment of the invention, W1 is N, W2 is CR6, W3 is CR5, and W5 and W6 are CH, which corresponds to pyridin-4-yl with the N atom in position 1, which can be optionally substituted by R6 in position 2 and/or R5 in position 3. More particularly, 1-pyridin-4-yl can be monosubstituted by R6 in position 2 or R5 in position 3.

In another particular embodiment of the invention, W1 is N, W2 is CR6, W3 is N or CR5 and W5 is N or CH under the proviso that either W3 or W5 is N, and W6 is CH, which corresponds to 1,3-pyrimidin-4-yl or 1,5-pyrimidin-4-yl, which can be optionally substituted by R6 in position 2. More particularly, 1,5-pyrimidin-4-yl is provided, which can be monosubstituted by R6 in position 2. It is considered to be identical to 1,3-pyrimidin-4-yl, which can be monosubstituted in position 6.

In still another particular embodiment of the invention, W1 is N, W2 is CR6, W3 and W5 are N, and W6 is CH, which corresponds to 1,3,5-triazin-4-yl, which can be optionally monosubstituted by R6 in position 2.

It is more preferred that 1-pyridin-4-yl, 1,5-pyrimidin-4-yl, 1,3,5-triazin-4-yl can be monosubstituted by R6 in position 2 and/or R5 in position 3. In a highly preferred embodiment of the invention, 1-pyridin-4-yl can be monosubstituted by R6 in position 2 or R5 in position 3.

It is a preferred embodiment of the R1 radical according to the present invention to be Y, more preferably H or A, most preferably H.

It is a preferred embodiment of the R5 radical according to the present invention to be H, A, OA, CN, -Alk-OY, COOY, —CO—NYY, NYY, —OAlk-OY, —OAlk-NYY, —OAlk-Het$^3$, —NH—CO-Alk-NYY, Hal, —CO—NYY—NYY or —CO—NH-Alk-Het$^3$. More preferably, R5 denotes H, OA, CN, -Alk-OH, COOA, —CO—NHA, NH$_2$, —OAlk-OY, —OAlk-NAA, —OAlk-Het$^3$, —NH—CO-Alk-NAA, Cl, —CO—NHA-NAA or —CO—NH-Alk-Het$^3$.

It is a preferred embodiment according to the present invention that R1 and R5 together also denote —CH═CH—, —CO—NH—, —SO$_2$—NH—, —N═C(Y)—, —CH═C(NO$_2$)— or —CH═C(Hal)-. More preferably, R1 and R5 denote together —CH═CH—, —N═C(H)— or —CH═C (Br)—.

It is a preferred embodiment of the R6 radical according to the present invention to be H, A, OA, NH$_2$, —NH—COA, —CO—NHA, Hal, NAA, —NH—CO-Alk-NYY, —NH-Alk-Het$^3$, —NH—CO—NH$_2$, —NH—CO-Het$^3$, —CO—NH-Het$^3$, —NH—CO-Alk-OH or —NH—CO-Alk-NH—COOA.

It is a preferred embodiment of the R3 radical according to the present invention to be H.

It is a preferred embodiment of the R4 radical according to the present invention to be H.

It is a preferred embodiment of the X radical according to the present invention to be NR1, CH$_2$, O or S, more preferably NR1, CH$_2$ or S, most preferably NR1 or S, highly preferably NR1.

Accordingly, the subject-matter of the invention relates to compounds of formula (I), in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention. That means, the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

In another preferred embodiment of the present invention, hetarylaminonaphthyridine derivatives of formula (II) are provided,

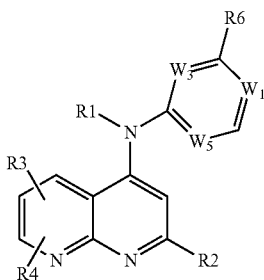

(II)

wherein

W1, W5 denotes independently from one another N or CH;

W3 denotes N or CR5;

under the proviso that at least one of W1, W3 or W5 denotes N;

R1, R3, R4 denotes independently from one another H or A;

R5 denotes H, A, OA, CN, -Alk-OY, COOY, —CO—NYY, NYY, —OAlk-OY, —OAlk-NYY, —OAlk-Het³, —NH—CO-Alk-NYY, Hal, —CO—NYY—NYY or —CO—NH-Alk-Het³;

R1, R5 together also denote —CH=CH—, —CO—NH—, —SO₂—NH—, —N=C(Y)—, —CH=C(NO₂)— or —CH=C(Hal)-;

R6 denotes H, A, OA, NH₂, —NH—COA, —CO—NHA, Hal, NAA, —NH—CO-Alk-NYY, —NH-Alk-Het³, —NH—CO—NH₂, —NH—CO-Het³, —CO—NH-Het³, —NH—CO-Alk-OH or —NH—CO-Alk-NH—COOA;

R2 denotes phenyl, pyridyl, pyrazolyl or pyrazinyl, each of which can be mono-, di- or trisubstituted by at least one substituent selected from the group of F, Cl, Br, CH₃, CF₃, CN, OCH₃, OCF₃;

Y denotes H or A;

A denotes unbranched or branched alkyl having 1-4 C atoms, in which 1-5 H atoms can be replaced by F and/or Cl;

Alk denotes alkylene having 1-3 C atoms;

Het³ denotes piperazine, piperidine, morpholine, pyrrolidine, piperidone, morpholinone or pyrrolidone, which can be monosubstituted by A, Hal, COOY or NYY;

and

Hal denotes F, Cl or Br;

and/or physiologically acceptable salts thereof.

For the sake of clarity, the following sub-structure within formula (IA)

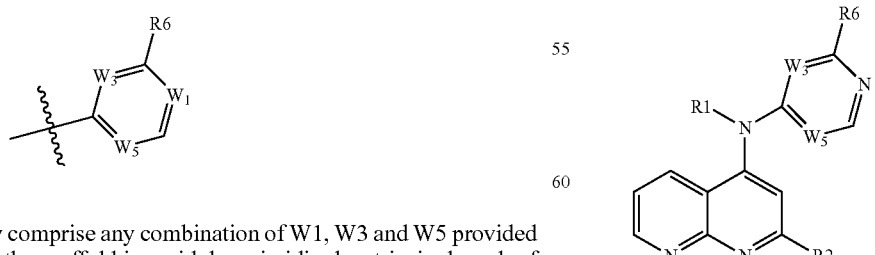

may comprise any combination of W1, W3 and W5 provided that the scaffold is pyridyl, pyrimidinyl or triazinyl, each of which can be optionally substituted as indicated above. Particularly, said sub-structure denotes the following scaffolds within the preferred embodiment according to sub-formula (II):

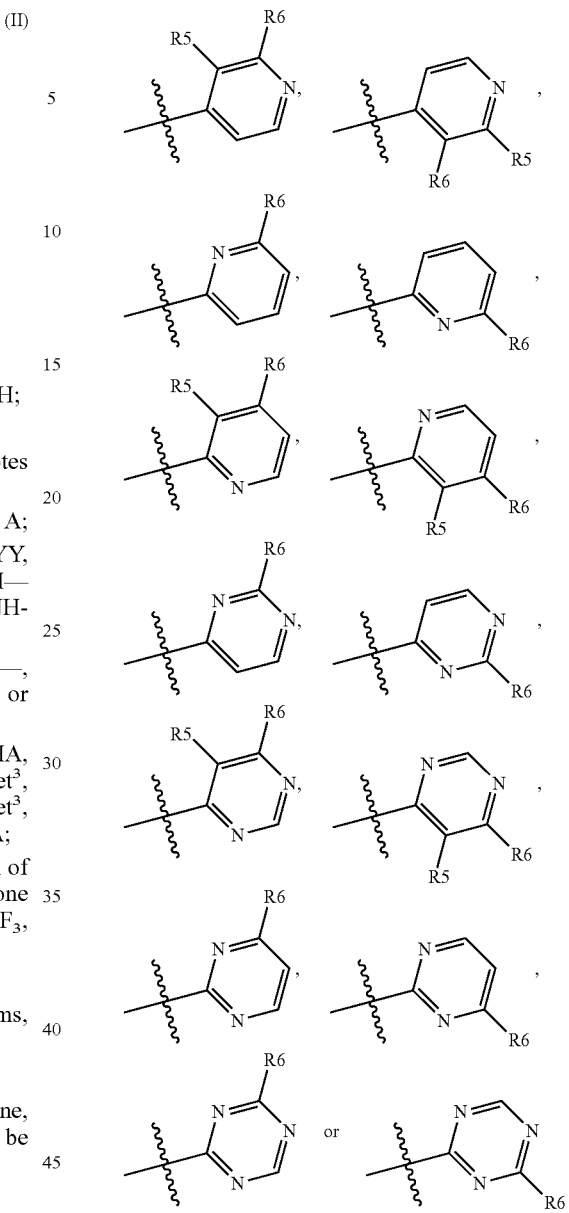

In a more preferred embodiment of the present invention, hetarylaminonaphthyridine derivatives of sub-formula (III) are provided, (III)

wherein

W3 denotes N or CR5;

W5 denotes N or CH;

R1 denotes H;
R5 denotes H, OA, CN, -Alk-OH, COOA, —CO—NHA, NH$_2$, —OAlk-OY, —OAlk-NAA, —OAlk-Het$^3$; —NH—CO-Alk-NAA, Cl or —CO—NHA-NAA;
R1, R5 together also denote —CH=CH—, —N=C(H)— or —CH=C(Br)—;
R6 denotes H, A, OA, NH$_2$, —NH—COA; —CO—NHA, Cl, NAA, —NH—CO-Alk-NH$_2$, —NH-Alk-Het$^3$, —NH—CO—NH$_2$, —NH—CO-Het$^3$, —CO—NH-Het$^3$, —NH—CO-Alk-OH or —NH—CO-Alk-NH—COOA;
R2 denotes phenyl, pyridin-2-yl, 2-fluoro-phenyl, 4-fluoro-phenyl, 2-fluoro-5-fluoro-phenyl, 2,4,5-trifluoro-phenyl, 2-fluoro-5-chloro-phenyl, 2-fluoro-5-bromo-phenyl, 2-fluoro-5-trifluoromethyl-phenyl, 2-fluoro-5-trifluoromethoxy-phenyl, 3-chloro-phenyl, 3-trifluoromethyl-phenyl, 6-methyl-pyridin-2-yl, pyrazol-4-yl, 1-methyl-pyrazol-3-yl, 3-methyl-pyrazol-1-yl;
Y denotes H or A;
A denotes methyl, ethyl, propyl or trifluoromethyl;
Alk denotes alkylene having 1-3 C atoms;
and
Het$^3$ denotes piperazine or morpholine, which can be mono-substituted by A;
and/or physiologically acceptable salts thereof.

In another more preferred embodiment of the present invention, hetarylaminonaphthyridine derivatives of formula (IA) are provided, $$R1'\text{-}T\text{-}R2 \qquad (IA)$$

wherein
T denotes 1,8-naphthyridine;
R1' denotes

[structures]

and
R2 denotes

[structures]

and/or physiologically acceptable salts thereof.

Most preferred embodiments are those compounds of formulae (I), (II), (III) and (IA) as listed in Table 1.

TABLE 1

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 01 | *structure* | 351 | 1.43 | +++ | |
| 02 | *structure* | 367 | 1.53 | +++ | |
| 03 | *structure* | 314 | 1.14 | +++ | |
| 04 | *structure* | 480 | 1.28 | ++ | |

TABLE 1-continued

Compounds of formulae (I), (II), (III), (IA)

| No. | Structure | LC-MS M + H+ found | LC-MS R_t [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 05 | 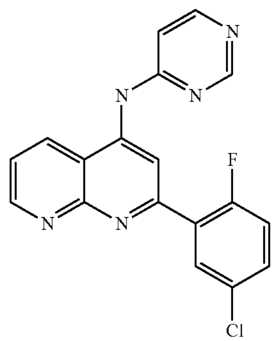 [SMILES: Fc1ccc(Cl)cc1-c1cc(Nc2ccncn2)c2cccnc2n1] | 352 | 1.66 | +++ | |
| 06 | 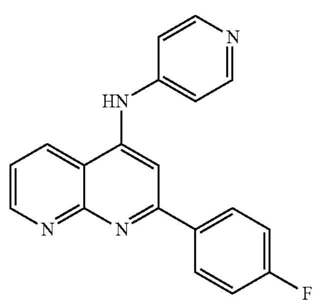 [SMILES: Fc1ccc(-c2cc(Nc3ccncc3)c3cccnc3n2)cc1] | 317 | 1.23 | +++ | |
| 07 | 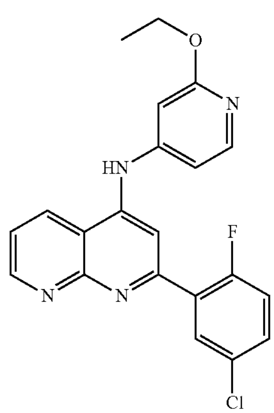 [SMILES: CCOc1cc(Nc2cc(-c3cc(Cl)ccc3F)nc3ncccc23)ccn1] | 395 | 1.73 | ++ | |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 08 | 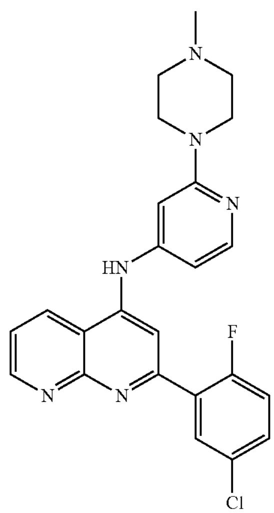 [SMILES: CN1CCN(c2cc(Nc3cc(-c4cc(Cl)ccc4F)nc4ncccc34)ccn2)CC1] | 449 | 1.24 | + | |
| 09 | 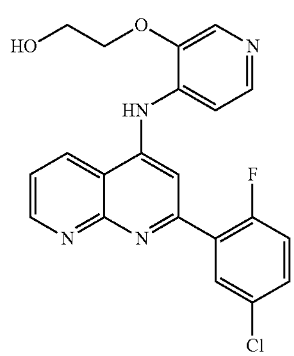 [SMILES: OCCOc1cnccc1Nc1cc(-c2cc(Cl)ccc2F)nc2ncccc12] | 411 | 1.38 | +++ | |
| 10 | 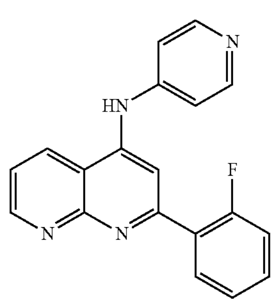 [SMILES: Fc1ccccc1-c1cc(Nc2ccncc2)c2cccnc2n1] | 317 | 1.21 | +++ | |

TABLE 1-continued
Compounds of formulae (I), (II), (III), (IA)
| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 11 | 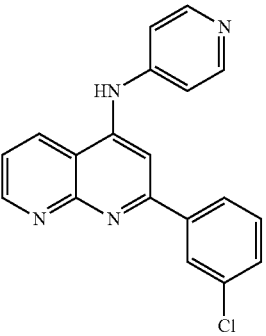 [SMILES: Clc1cccc(-c2cc(Nc3ccncc3)c3cccnc3n2)c1] | 333 | 1.36 | +++ | |
| 12 | 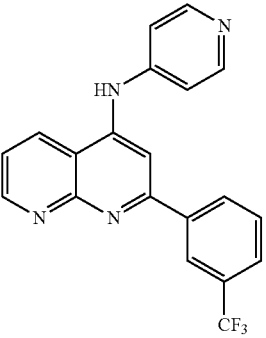 [SMILES: FC(F)(F)c1cccc(-c2cc(Nc3ccncc3)c3cccnc3n2)c1] | 367 | 1.45 | +++ | |
| 13 | 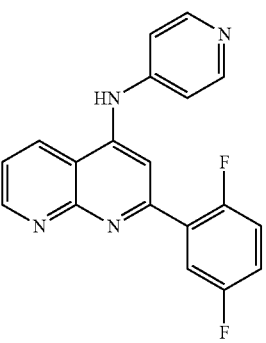 [SMILES: Fc1ccc(F)c(-c2cc(Nc3ccncc3)c3cccnc3n2)c1] | 335 | 1.25 | +++ | |
| 14 | 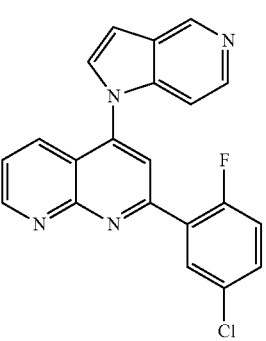 [SMILES: Fc1ccc(Cl)cc1-c1cc(-n2ccc3cnccc32)c2cccnc2n1] | 375 | 1.48 | +++ | |

TABLE 1-continued

Compounds of formulae (I), (II), (III), (IA)

| No. | Structure | LC-MS M + H+ found | LC-MS R_t [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 15 | 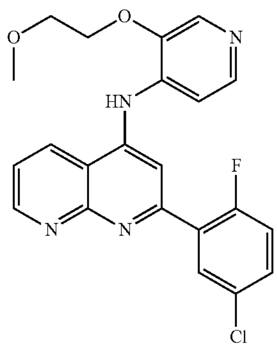 [SMILES: COCCOc1cnccc1Nc1cc(-c2cc(Cl)ccc2F)nc2ncccc12] | 425 | 1.49 | +++ | |
| 16 | 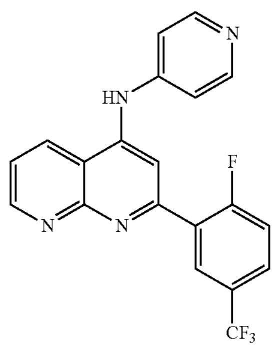 [SMILES: Fc1ccc(C(F)(F)F)cc1-c1cc(Nc2ccncc2)c2cccnc2n1] | 385 | 1.53 | +++ | |
| 17 | 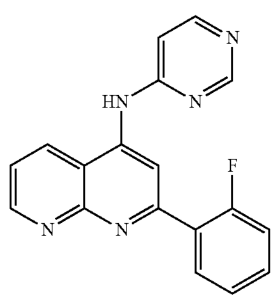 [SMILES: Fc1ccccc1-c1cc(Nc2ccncn2)c2cccnc2n1] | 318 | 1.36 | +++ | |
| 18 | 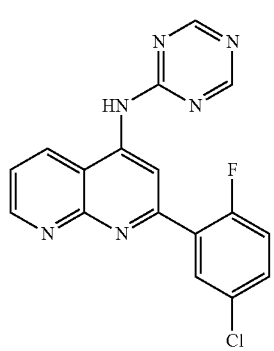 [SMILES: Fc1ccc(Cl)cc1-c1cc(Nc2ncncn2)c2cccnc2n1] | 353 | 1.86 | +++ | |

TABLE 1-continued

Compounds of formulae (I), (II), (III), (IA)

| No. | Structure | LC-MS M+H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 19 | 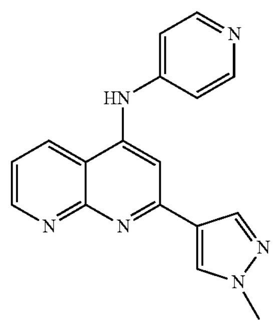 [SMILES: Cn1cc(-c2cc(Nc3ccncc3)c3cccnc3n2)cn1] | 303 | 0.94 | + | |
| 20 | 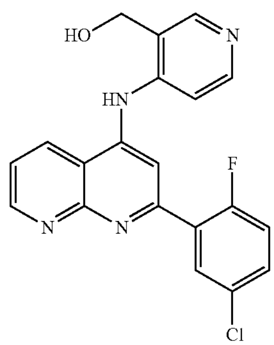 [SMILES: OCc1cnccc1Nc1cc(-c2cc(Cl)ccc2F)nc2ncccc12] | 381 | 1.37 | +++ | |
| 21 | 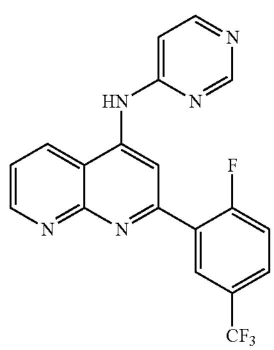 [SMILES: Fc1ccc(C(F)(F)F)cc1-c1cc(Nc2ccncn2)c2cccnc2n1] | 386 | 1.72 | +++ | |
| 22 | 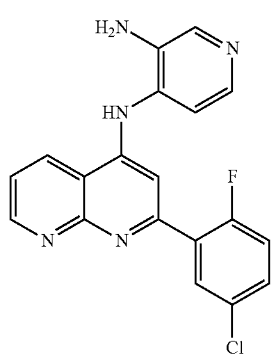 [SMILES: Nc1cnccc1Nc1cc(-c2cc(Cl)ccc2F)nc2ncccc12] | 366 | 1.33 | +++ | |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 23 | 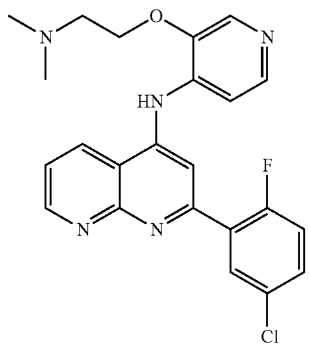 [SMILES: CN(C)CCOc1cnccc1Nc1cc(-c2cc(Cl)ccc2F)nc2ncccc12] | 438 | 1.09 | +++ | |
| 24 | 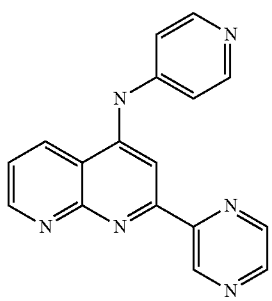 [SMILES: c1cnc2nc(-c3cnccn3)cc(Nc3ccncc3)c2c1] | 301 | 1.11 | + | |
| 25 | 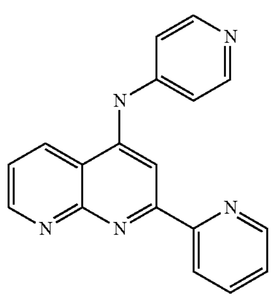 [SMILES: c1ccc(-c2cc(Nc3ccncc3)c3cccnc3n2)nc1] | 300 | 1.14 | +++ | |
| 26 | 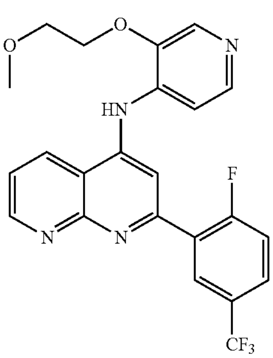 [SMILES: COCCOc1cnccc1Nc1cc(-c2cc(C(F)(F)F)ccc2F)nc2ncccc12] | 459 | 1.57 | +++ | |

TABLE 1-continued
Compounds of formulae (I), (II), (III), (IA)
| No. | Structure | LC-MS M + H+ found | LC-MS R_t [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 27 | 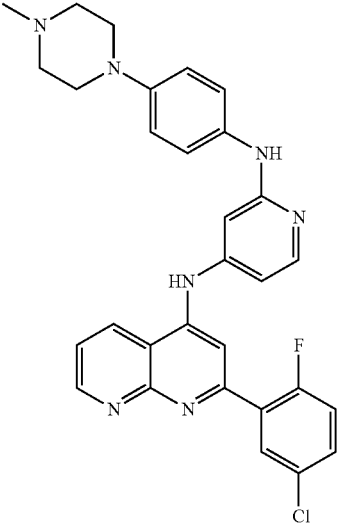 [SMILES: CN1CCN(c2ccc(Nc3cc(Nc4cc(-c5cc(Cl)ccc5F)nc5ncccc45)ccn3)cc2)CC1] | 540 | 1.35 | ++ | |
| 28 | 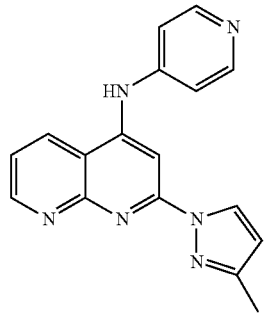 [SMILES: Cc1ccn(-c2cc(Nc3ccncc3)c3cccnc3n2)n1] | 303 | 1.18 | +++ | |
| 29 | 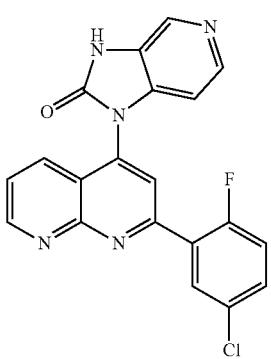 [SMILES: O=c1[nH]c2cnccc2n1-c1cc(-c2cc(Cl)ccc2F)nc2ncccc12] | 392 | 1.41 | +++ | |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 30 | 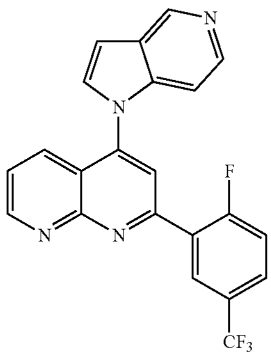 [SMILES: Fc1ccc(C(F)(F)F)cc1-c1cc(-n2ccc3cnccc32)c2cccnc2n1] | 409 | 1.58 | +++ | |
| 31 | 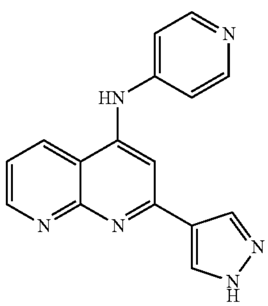 [SMILES: c1cnc2nc(-c3cn[nH]c3)cc(Nc3ccncc3)c2c1] | 289 | 0.89 | ++ | |
| 32 | 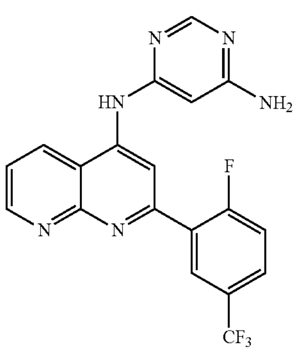 [SMILES: Nc1cc(Nc2cc(-c3cc(C(F)(F)F)ccc3F)nc3ncccc23)ncn1] | 401 | 1.59 | +++ | |
| 33 | 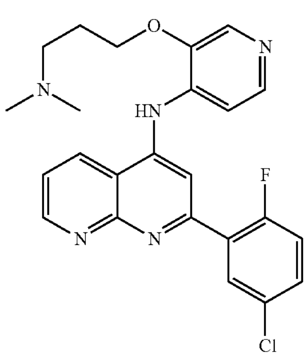 [SMILES: CN(C)CCCOc1cnccc1Nc1cc(-c2cc(Cl)ccc2F)nc2ncccc12] | 452 | 1.26 | +++ | |

TABLE 1-continued
Compounds of formulae (I), (II), (III), (IA)
| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 34 | 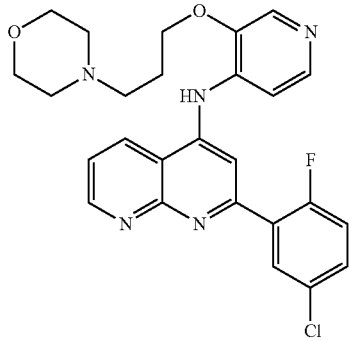 [SMILES: Fc1ccc(Cl)cc1-c1cc(Nc2ccncc2OCCCN2CCOCC2)c2cccnc2n1] | 494 | 1.20 | +++ | |
| 35 | 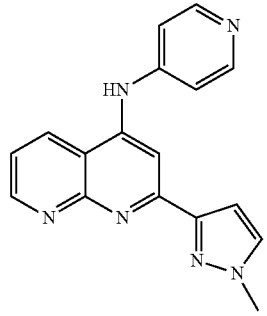 [SMILES: Cn1ccc(-c2cc(Nc3ccncc3)c3cccnc3n2)n1] | 303 | 1.02 | ++ | |
| 36 | 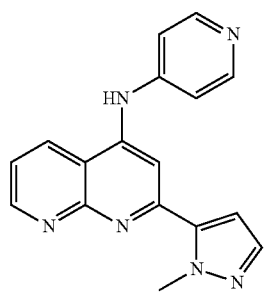 [SMILES: Cn1nccc1-c1cc(Nc2ccncc2)c2cccnc2n1] | 303 | 1.04 | + | |
| 37 | 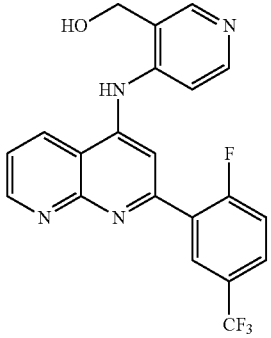 [SMILES: OCc1cnccc1Nc1cc(-c2cc(C(F)(F)F)ccc2F)nc2ncccc12] | 415 | 1.48 | +++ | |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 38 | 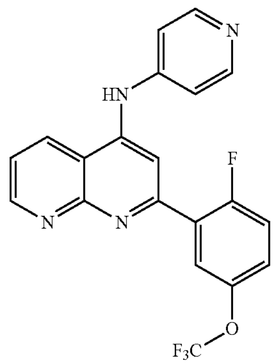 [SMILES: Fc1ccc(OC(F)(F)F)cc1-c1cc(Nc2ccncc2)c2cccnc2n1] | 401 | 1.55 | +++ | |
| 39 | 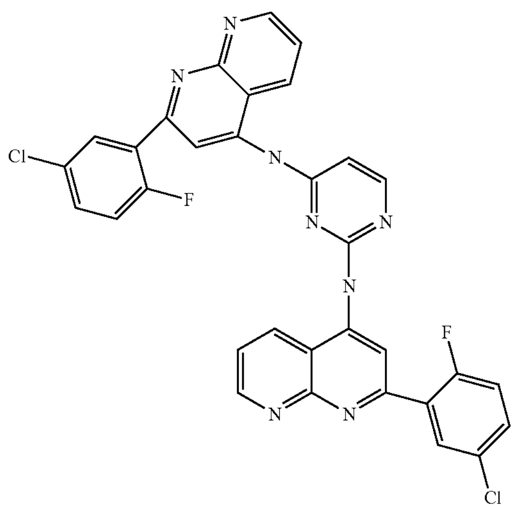 [SMILES: Fc1ccc(Cl)cc1-c1cc(Nc2ccnc(Nc3cc(-c4cc(Cl)ccc4F)nc4ncccc34)n2)c2cccnc2n1] | 623 | 1.92 | + | |
| 40 | 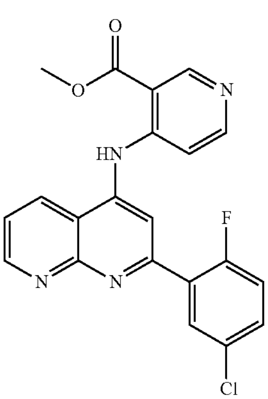 [SMILES: COC(=O)c1cnccc1Nc1cc(-c2cc(Cl)ccc2F)nc2ncccc12] | 409 | 1.60 | +++ | |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 41 | 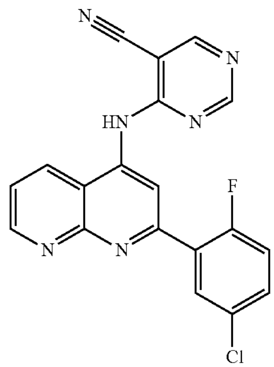 [SMILES: N#Cc1cncnc1Nc1cc(-c2cc(Cl)ccc2F)nc2ncccc12] | 377 | 1.94 | +++ | |
| 42 | 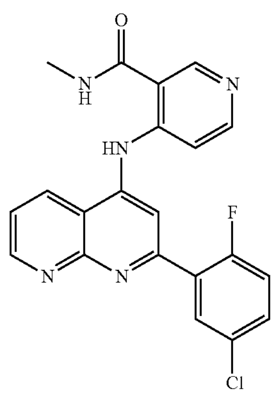 [SMILES: CNC(=O)c1cnccc1Nc1cc(-c2cc(Cl)ccc2F)nc2ncccc12] | 408 | 1.47 | +++ | |
| 43 | 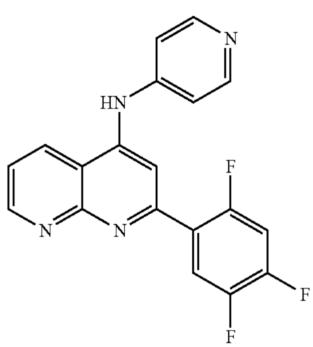 [SMILES: Fc1cc(F)c(-c2cc(Nc3ccncc3)c3cccnc3n2)cc1F] | 353 | 1.40 | +++ | |
| 44 | 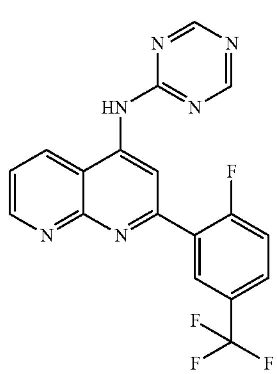 [SMILES: Fc1ccc(C(F)(F)F)cc1-c1cc(Nc2ncncn2)c2cccnc2n1] | 387 | 2.00 | +++ | |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 45 | (structure) | 538 | 1.82 | ++ | |
| 46 | (structure) | 438 | 1.11 | ++ | |
| 47 | (structure) | 478 | 1.11 | +++ | |

TABLE 1-continued

Compounds of formulae (I), (II), (III), (IA)

| No. | Structure | LC-MS M + H+ found | LC-MS R_t [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 48 | 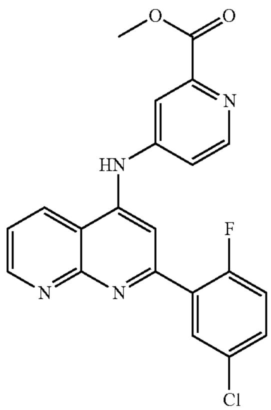 [SMILES: COC(=O)c1cc(Nc2cc(-c3cc(Cl)ccc3F)nc3ncccc23)ccn1] | 409 | 1.58 | +++ | |
| 49 | 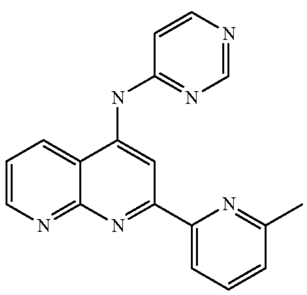 [SMILES: Cc1cccc(-c2cc(Nc3ccncn3)c3cccnc3n2)n1] | 315 | 1.18 | +++ | |
| 50 | 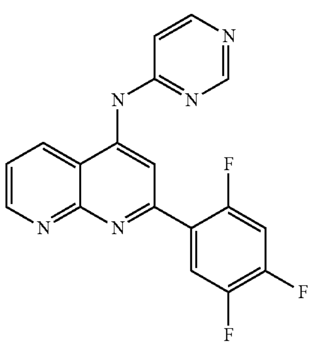 [SMILES: Fc1cc(F)c(-c2cc(Nc3ccncn3)c3cccnc3n2)cc1F] | 354 | 1.56 | +++ | |
| 51 | 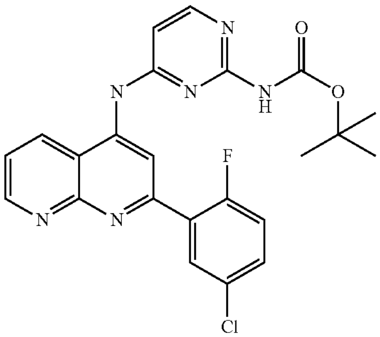 [SMILES: CC(C)(C)OC(=O)Nc1nccc(Nc2cc(-c3cc(Cl)ccc3F)nc3ncccc23)n1] | 467 | 1.80 | +++ | |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 52 | 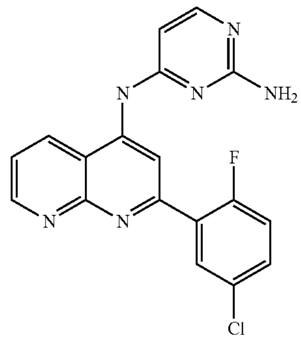 [SMILES: Nc1nccc(Nc2cc(-c3cc(Cl)ccc3F)nc3ncccc23)n1] | 367 | 1.36 | +++ | |
| 53 | 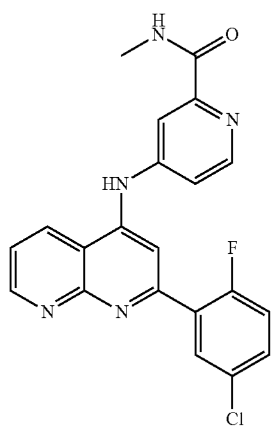 [SMILES: CNC(=O)c1cc(Nc2cc(-c3cc(Cl)ccc3F)nc3ncccc23)ccn1] | 408 | 1.63 | +++ | |
| 54 | 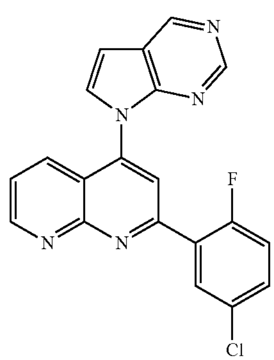 [SMILES: Fc1ccc(Cl)cc1-c1cc(-n2ccc3cncnc32)c2cccnc2n1] | 376 | 1.94 | +++ | |
| 55 | 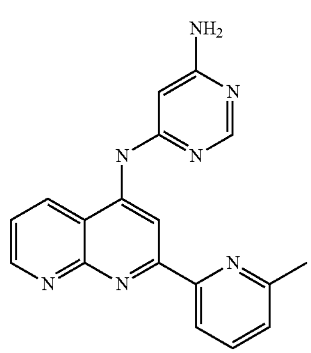 [SMILES: Cc1cccc(-c2cc(Nc3cc(N)ncn3)c3cccnc3n2)n1] | 330 | 1.18 | +++ | |

TABLE 1-continued
Compounds of formulae (I), (II), (III), (IA)
| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 56 | 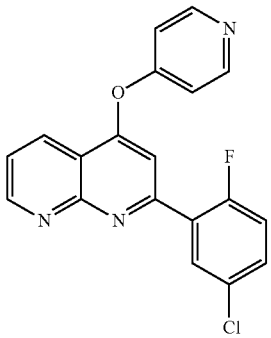 [SMILES: Fc1ccc(Cl)cc1-c1cc(Oc2ccncc2)c2cccnc2n1] | 352 | 1.63 | 0 | |
| 57 | 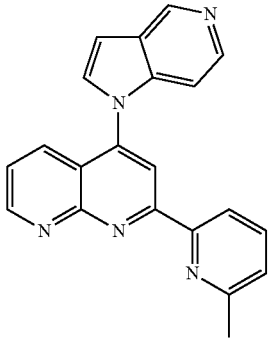 [SMILES: Cc1cccc(-c2cc(-n3ccc4cnccc43)c3cccnc3n2)n1] | 338 | 1.17 | +++ | |
| 58 | 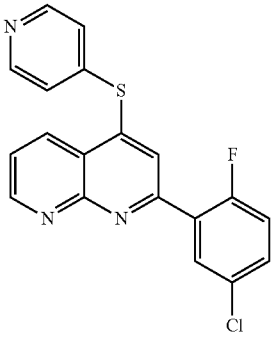 [SMILES: Fc1ccc(Cl)cc1-c1cc(Sc2ccncc2)c2cccnc2n1] | 368 | 1.92 | +++ | |
| 59 | 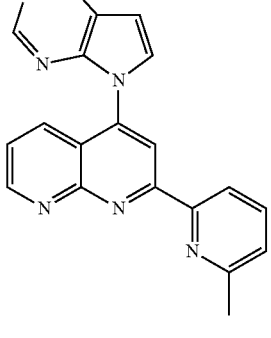 | 339 | 1.52 | ++ | |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 60 | 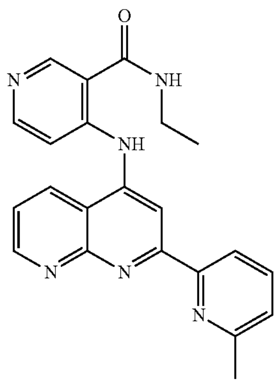 [SMILES: CCNC(=O)c1cnccc1Nc1cc(-c2cccc(C)n2)nc2ncccc12] | 385 | 1.24 | +++ | |
| 61 | 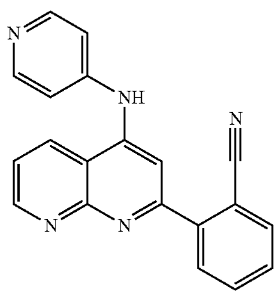 [SMILES: N#Cc1ccccc1-c1cc(Nc2ccncc2)c2cccnc2n1] | 324 | 1.15 | ++ | |
| 62 | 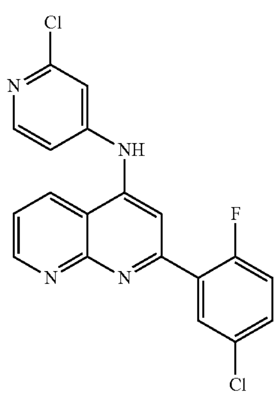 [SMILES: Fc1ccc(Cl)cc1-c1cc(Nc2ccnc(Cl)c2)c2cccnc2n1] | 385 | 1.96 | +++ | |
| 63 | 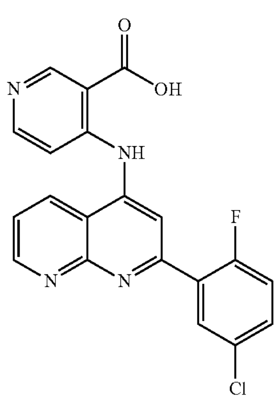 [SMILES: O=C(O)c1cnccc1Nc1cc(-c2cc(Cl)ccc2F)nc2ncccc12] | 395 | 1.39 | +++ | |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 64 | (structure) | 409 | 1.45 | | |
| 65 | (structure) | 376 | 1.68 | +++ | |
| 66 | (structure) | 350 | 1.47 | | |

TABLE 1-continued
Compounds of formulae (I), (II), (III), (IA)
| No. | Structure | LC-MS M + H+ found | LC-MS $R_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 67 | 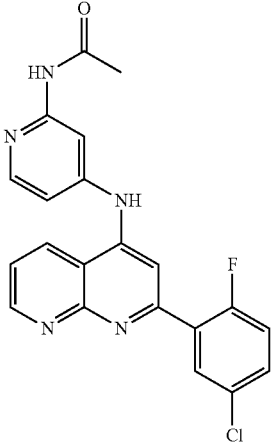 [SMILES: CC(=O)Nc1cc(Nc2cc(-c3cc(Cl)ccc3F)nc3ncccc23)ccn1] | 408 | 1.43 | +++ | |
| 68 | 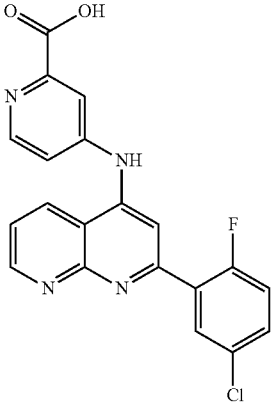 [SMILES: O=C(O)c1cc(Nc2cc(-c3cc(Cl)ccc3F)nc3ncccc23)ccn1] | 395 | 1.42 | + | |
| 69 | 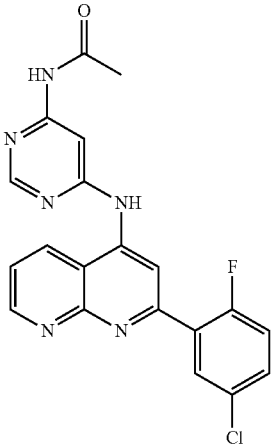 [SMILES: CC(=O)Nc1cc(Nc2cc(-c3cc(Cl)ccc3F)nc3ncccc23)ncn1] | 409 | 1.72 | | |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 70 | 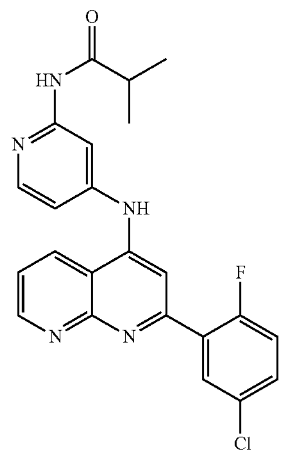 [SMILES: CC(C)C(=O)Nc1cc(Nc2cc(-c3cc(Cl)ccc3F)nc3ncccc23)ccn1] | 436 | 1.55 | +++ | |
| 71 | 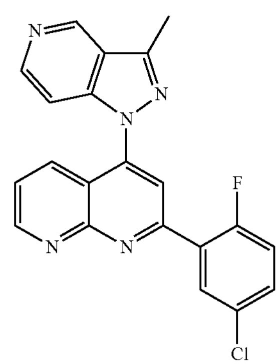 [SMILES: Cc1nn(-c2cc(-c3cc(Cl)ccc3F)nc3ncccc23)c2ccncc12] | 390 | 1.65 | +++ | |
| 72 | 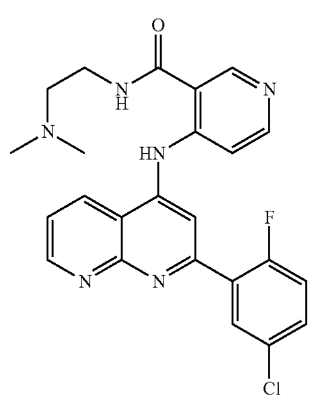 [SMILES: CN(C)CCNC(=O)c1cnccc1Nc1cc(-c2cc(Cl)ccc2F)nc2ncccc12] | 465 | 1.18 | +++ | +++ |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 73 | 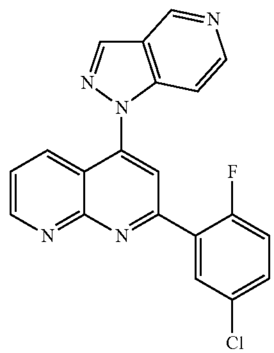 [SMILES: Fc1ccc(Cl)cc1-c1cc(-n2ncc3cnccc32)c2cccnc2n1] | 376 | 1.63 | +++ | +++ |
| 74 | 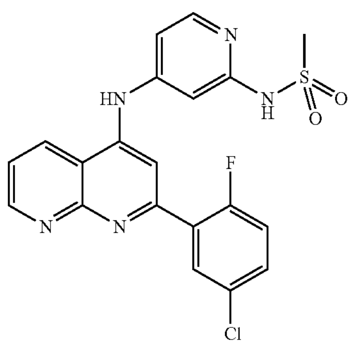 [SMILES: CS(=O)(=O)Nc1cc(Nc2cc(-c3cc(Cl)ccc3F)nc3ncccc23)ccn1] | 444 | 1.55 | ++ | + |
| 75 | 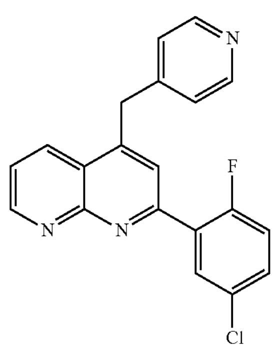 [SMILES: Fc1ccc(Cl)cc1-c1cc(Cc2ccncc2)c2cccnc2n1] | 350 | 1.47 | + | 0 |
| 76 | 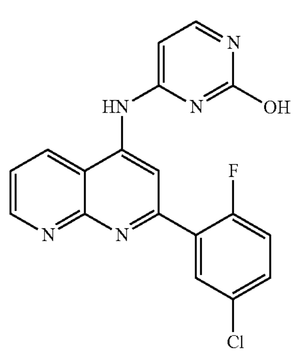 [SMILES: Oc1nccc(Nc2cc(-c3cc(Cl)ccc3F)nc3ncccc23)n1] | 368 | 1.45 | ++ | + |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 77 | 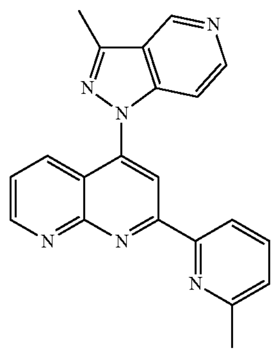 [SMILES: Cc1cccc(-c2cc(-n3nc(C)c4cnccc43)c3cccnc3n2)n1] | 1.34 | 353 | +++ | + |
| 78 | 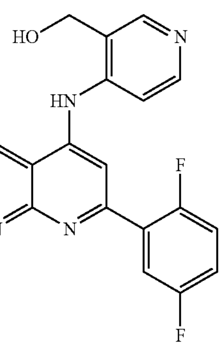 | 1.21 | 365 | +++ | +++ |
| 79 | 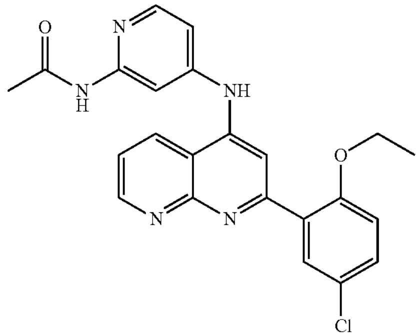 [SMILES: CCOc1ccc(Cl)cc1-c1cc(Nc2ccnc(NC(C)=O)c2)c2cccnc2n1] | 1.49 | 434 | ++ | ++ |
| 80 | 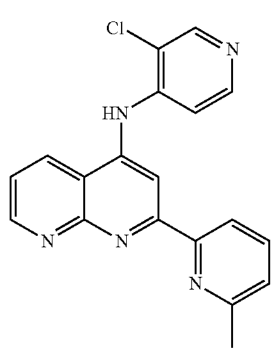 [SMILES: Cc1cccc(-c2cc(Nc3ccncc3Cl)c3cccnc3n2)n1] | 1.20 | 348 | +++ | +++ |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 81 | 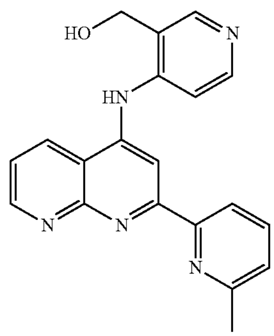 [SMILES: Cc1cccc(-c2cc(Nc3ccncc3CO)c3cccnc3n2)n1] | 344 | 1.07 | +++ | ++ |
| 82 | 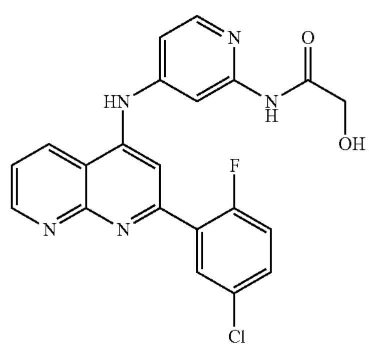 [SMILES: O=C(CO)Nc1cc(Nc2cc(-c3cc(Cl)ccc3F)nc3ncccc23)ccn1] | 424 | 1.42 | +++ | +++ |
| 83 | 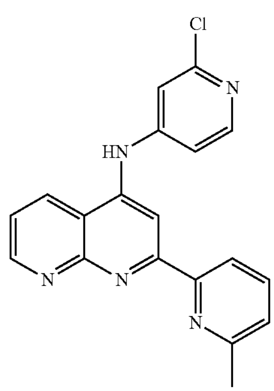 [SMILES: Cc1cccc(-c2cc(Nc3ccnc(Cl)c3)c3cccnc3n2)n1] | 348 | 1.50 | ++ | + |
| 84 | 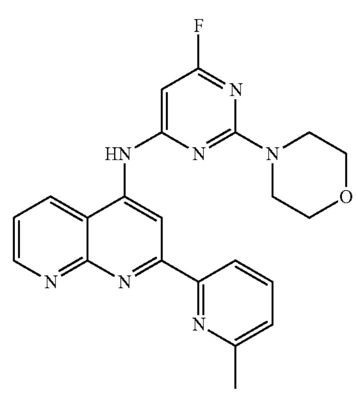 [SMILES: Cc1cccc(-c2cc(Nc3cc(F)nc(N4CCOCC4)n3)c3cccnc3n2)n1] | 418 | 1.64 | 0 | 0 |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 85 | 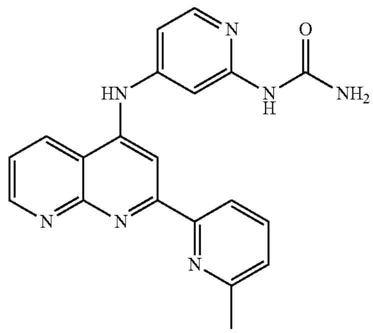 [SMILES: Cc1cccc(-c2cc(Nc3ccnc(NC(N)=O)c3)c3cccnc3n2)n1] | 1.13 | 372 | +++ | ++ |
| 86 | 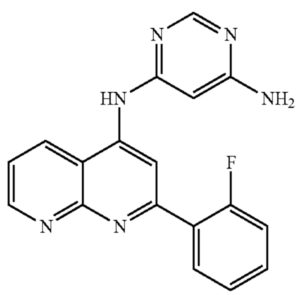 [SMILES: Nc1cc(Nc2cc(-c3ccccc3F)nc3ncccc23)ncn1] | 1.23 | 333 | +++ | ++ |
| 87 | 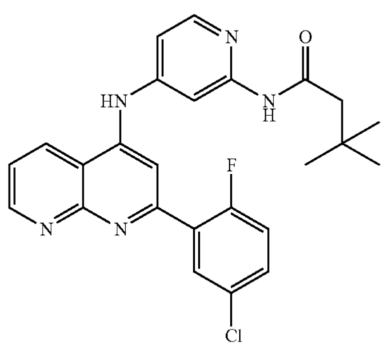 [SMILES: CC(C)(C)CC(=O)Nc1cc(Nc2cc(-c3cc(Cl)ccc3F)nc3ncccc23)ccn1] | 1.81 | 464 | +++ | +++ |
| 88 | 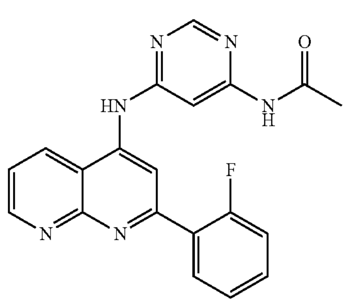 [SMILES: CC(=O)Nc1cc(Nc2cc(-c3ccccc3F)nc3ncccc23)ncn1] | 1.44 | 375 | +++ | ++ |

TABLE 1-continued

Compounds of formulae (I), (II), (III), (IA)

| No. | Structure | LC-MS M+H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 89 | 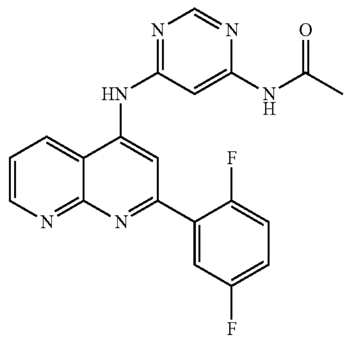 [SMILES: CC(=O)Nc1cc(Nc2cc(-c3cc(F)ccc3F)nc3ncccc23)ncn1] | 1.59 | 393 | +++ | +++ |
| 90 | 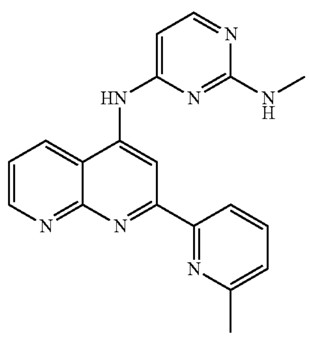 [SMILES: CNc1nccc(Nc2cc(-c3cccc(C)n3)nc3ncccc23)n1] | 1.20 | 344 | +++ | ++ |
| 91 | 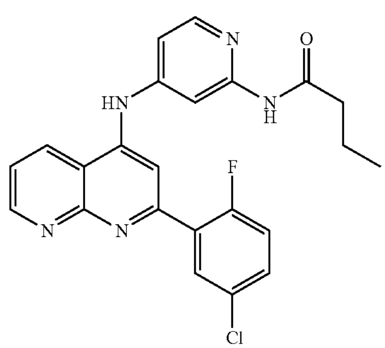 [SMILES: CCCC(=O)Nc1cc(Nc2cc(-c3cc(Cl)ccc3F)nc3ncccc23)ccn1] | 1.59 | 436 | +++ | +++ |
| 92 | 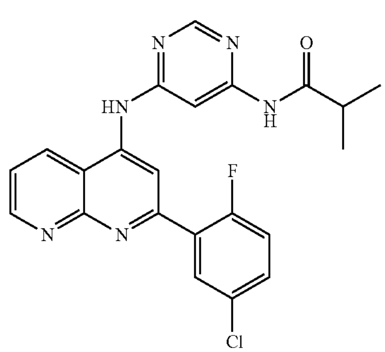 [SMILES: CC(C)C(=O)Nc1cc(Nc2cc(-c3cc(Cl)ccc3F)nc3ncccc23)ncn1] | 1.97 | 437 | +++ | +++ |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 93 | 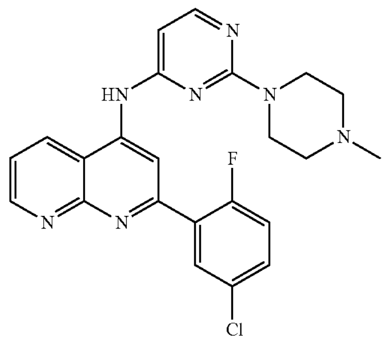 [SMILES: CN1CCN(c2nccc(Nc3cc(-c4cc(Cl)ccc4F)nc4ncccc34)n2)CC1] | 1.27 | 450 | 0 | 0 |
| 94 | 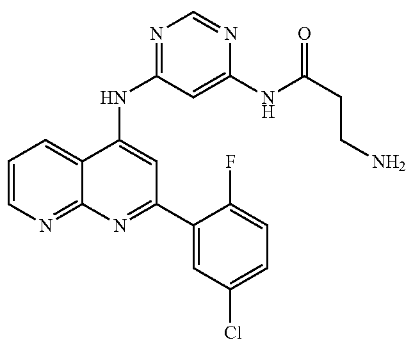 [SMILES: NCCC(=O)Nc1cc(Nc2cc(-c3cc(Cl)ccc3F)nc3ncccc23)ncn1] | 1.39 | 438 | +++ | +++ |
| 95 | 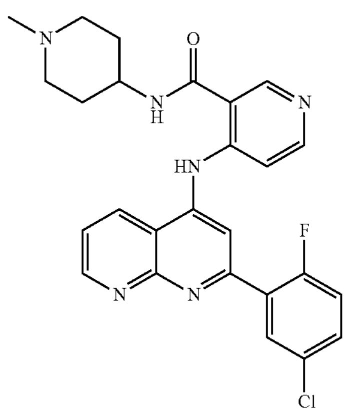 | 1.19 | 491 | +++ | +++ |
| 96 | 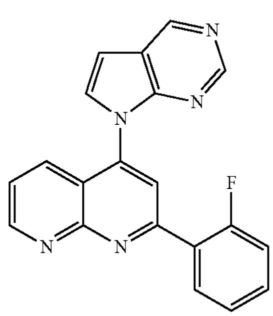 [SMILES: Fc1ccccc1-c1cc(-n2ccc3cncnc32)c2cccnc2n1] | 1.74 | 342 | ++ | + |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 97 | 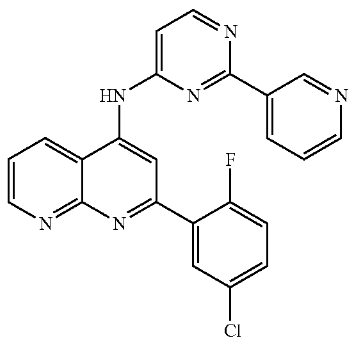 [SMILES: Fc1ccc(Cl)cc1-c1cc(Nc2ccnc(-c3cccnc3)n2)c2cccnc2n1] | 1.75 | 429 | + | 0 |
| 98 | 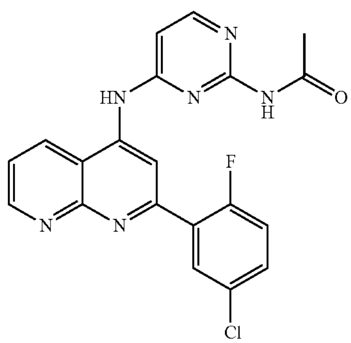 [SMILES: CC(=O)Nc1nccc(Nc2cc(-c3cc(Cl)ccc3F)nc3ncccc23)n1] | 1.42 | 409 | +++ | +++ |
| 99 | 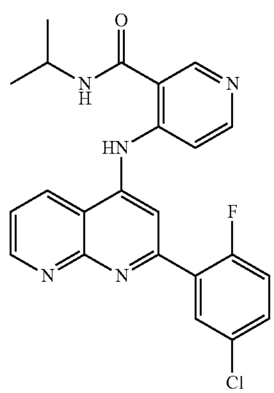 [SMILES: CC(C)NC(=O)c1cnccc1Nc1cc(-c2cc(Cl)ccc2F)nc2ncccc12] | 1.58 | 436 | +++ | +++ |
| 100 | 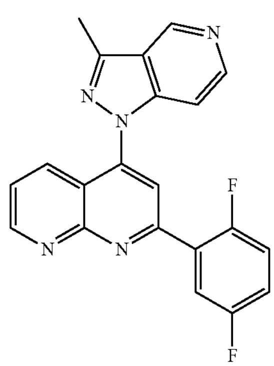 [SMILES: Cc1nn(-c2cc(-c3cc(F)ccc3F)nc3ncccc23)c2ccncc12] | 1.50 | 374 | +++ | ++ |

TABLE 1-continued

Compounds of formulae (I), (II), (III), (IA)

| No. | Structure | LC-MS M + H+ found | LC-MS R_t [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 101 | 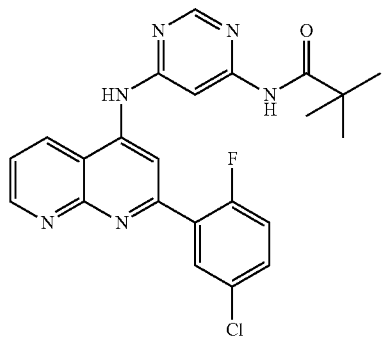 [SMILES: CC(C)(C)C(=O)Nc1cc(Nc2cc(-c3cc(Cl)ccc3F)nc3ncccc23)ncn1] | 2.14 | 451 | ++ | + |
| 102 | 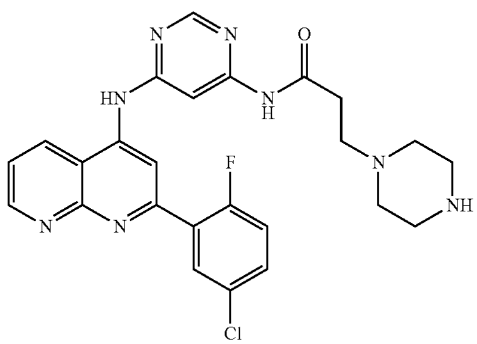 [SMILES: O=C(CCN1CCNCC1)Nc1cc(Nc2cc(-c3cc(Cl)ccc3F)nc3ncccc23)ncn1] | 1.28 | 507 | 0 | 0 |
| 103 | 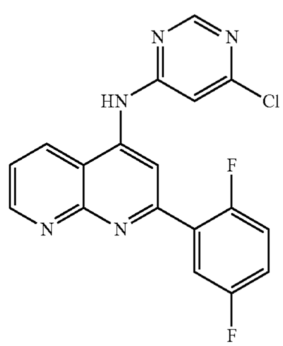 [SMILES: Fc1ccc(F)c(-c2cc(Nc3cc(Cl)ncn3)c3cccnc3n2)c1] | 1.95 | 370 | ++ | 0 |
| 104 | 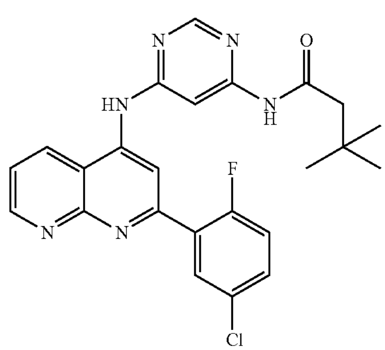 [SMILES: CC(C)(C)CC(=O)Nc1cc(Nc2cc(-c3cc(Cl)ccc3F)nc3ncccc23)ncn1] | 2.25 | 465 | +++ | +++ |

TABLE 1-continued

Compounds of formulae (I), (II), (III), (IA)

| No. | Structure | LC-MS R$_t$ [min] method B | LC-MS M + H+ found | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 105 | 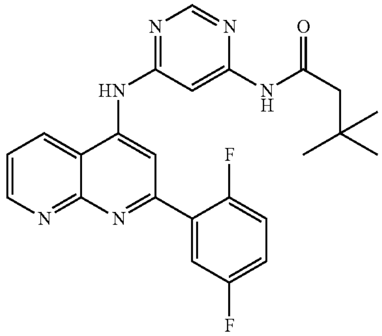 [SMILES: CC(C)(C)CC(=O)Nc1cc(Nc2cc(-c3cc(F)ccc3F)nc3ncccc23)ncn1] | 2.13 | 449 | +++ | ++ |
| 106 | 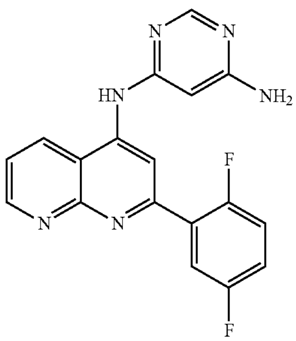 [SMILES: Nc1cc(Nc2cc(-c3cc(F)ccc3F)nc3ncccc23)ncn1] | 1.25 | 351 | +++ | ++ |
| 107 | 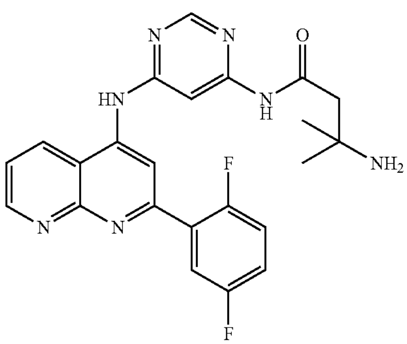 [SMILES: CC(C)(N)CC(=O)Nc1cc(Nc2cc(-c3cc(F)ccc3F)nc3ncccc23)ncn1] | 1.24 | 450 | +++ | +++ |
| 108 | 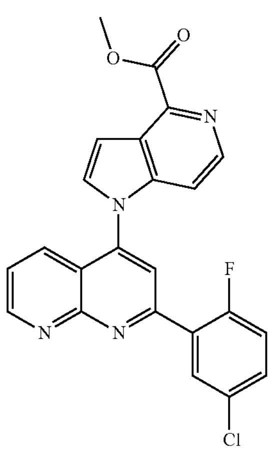 [SMILES: COC(=O)c1nccc2c1ccn2-c1cc(-c2cc(Cl)ccc2F)nc2ncccc12] | 1.87 | 433 | ++ | + |

TABLE 1-continued

Compounds of formulae (I), (II), (III), (IA)

| No. | Structure | LC-MS M+H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 109 | 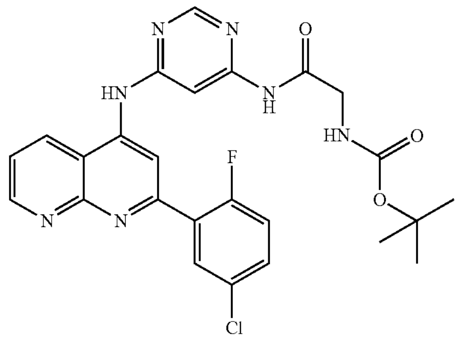 [SMILES: CC(C)(C)OC(=O)NCC(=O)Nc1cc(Nc2cc(-c3cc(Cl)ccc3F)nc3ncccc23)ncn1] | 1.99 | 524 | +++ | +++ |
| 110 | 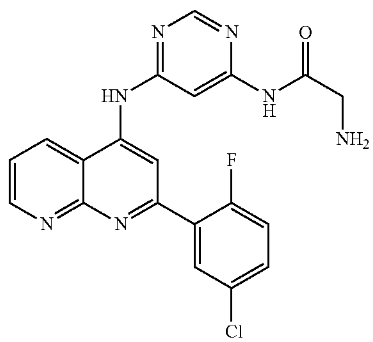 [SMILES: NCC(=O)Nc1cc(Nc2cc(-c3cc(Cl)ccc3F)nc3ncccc23)ncn1] | 1.35 | 424 | +++ | +++ |
| 111 | 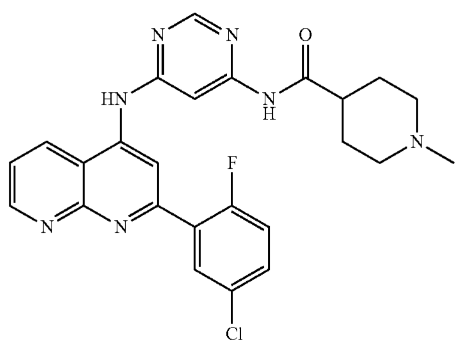 [SMILES: CN1CCC(C(=O)Nc2cc(Nc3cc(-c4cc(Cl)ccc4F)nc4ncccc34)ncn2)CC1] | 1.37 | 492 | +++ | +++ |
| 112 | 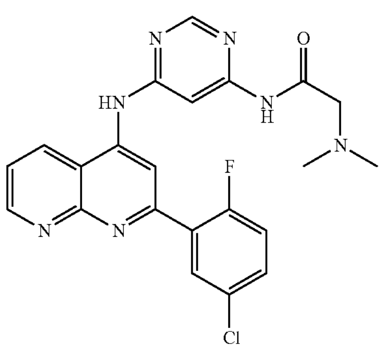 [SMILES: CN(C)CC(=O)Nc1cc(Nc2cc(-c3cc(Cl)ccc3F)nc3ncccc23)ncn1] | 1.38 | 452 | +++ | +++ |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 113 | 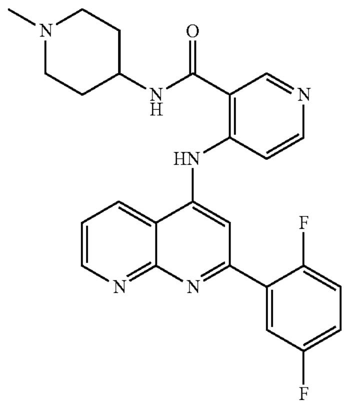 [SMILES: CN1CCC(NC(=O)c2cnccc2Nc2cc(-c3cc(F)ccc3F)nc3ncccc23)CC1] | 1.12 | 475 | +++ | +++ |
| 114 | 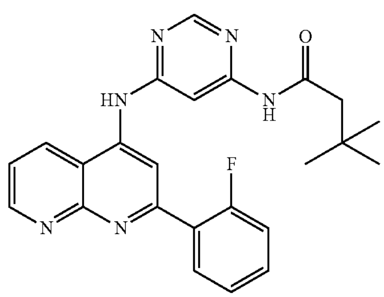 [SMILES: CC(C)(C)CC(=O)Nc1cc(Nc2cc(-c3ccccc3F)nc3ncccc23)ncn1] | 1.92 | 431 | +++ | ++ |
| 115 | 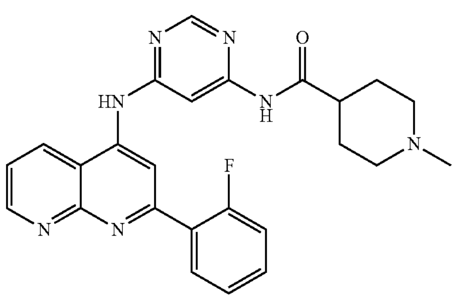 [SMILES: CN1CCC(C(=O)Nc2cc(Nc3cc(-c4ccccc4F)nc4ncccc34)ncn2)CC1] | 1.19 | 458 | +++ | ++ |
| 116 | 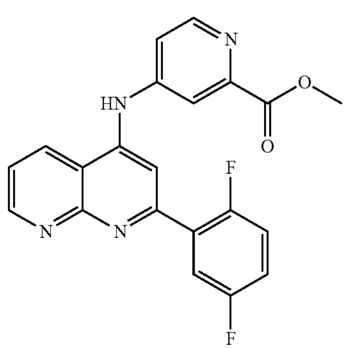 [SMILES: COC(=O)c1cc(Nc2cc(-c3cc(F)ccc3F)nc3ncccc23)ccn1] | 1.47 | 393 | + | 0 |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 117 | 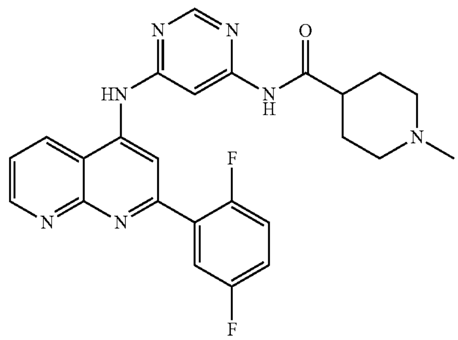 | 1.31 | 476 | +++ | +++ |
| 118 | 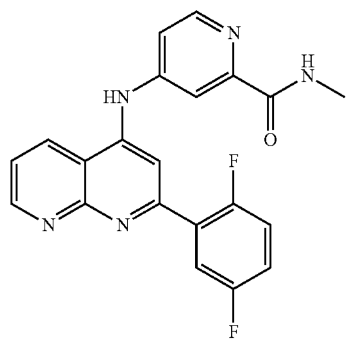 [SMILES: CNC(=O)c1cc(Nc2cc(-c3cc(F)ccc3F)nc3ncccc23)ccn1] | 1.51 | 392 | ++ | + |
| 119 | 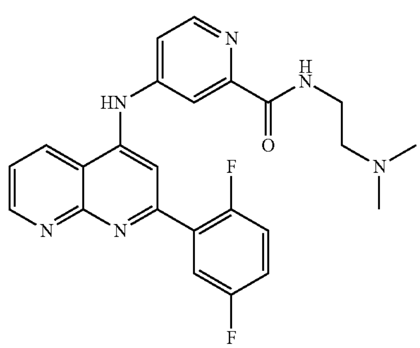 [SMILES: CN(C)CCNC(=O)c1cc(Nc2cc(-c3cc(F)ccc3F)nc3ncccc23)ccn1] | 1.23 | 449 | + | 0 |
| 120 | 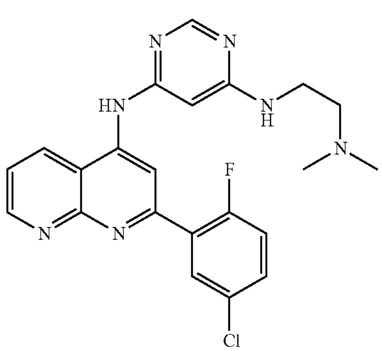 [SMILES: CN(C)CCNc1cc(Nc2cc(-c3cc(Cl)ccc3F)nc3ncccc23)ncn1] | 1.27 | 438 | ++ | ++ |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 121 | 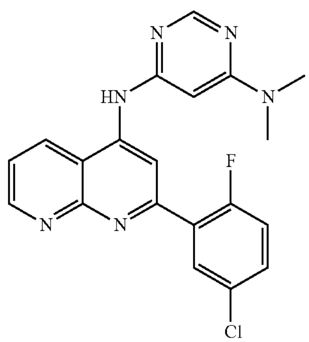 | 1.65 | 395 | +++ | +++ |
| 122 | 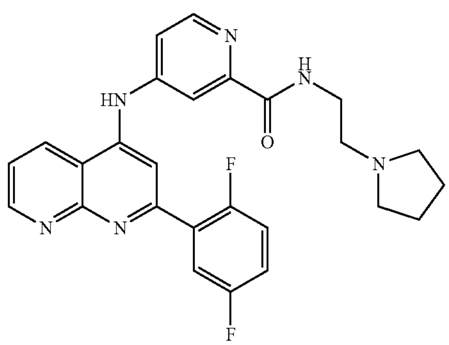 [SMILES: O=C(NCCN1CCCC1)c1cc(Nc2cc(-c3cc(F)ccc3F)nc3ncccc23)ccn1] | 1.25 | 475 | + | 0 |
| 123 | 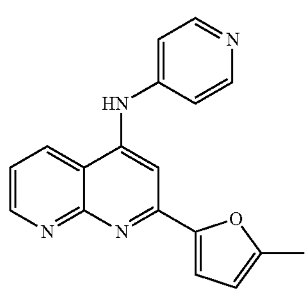 [SMILES: Cc1ccc(-c2cc(Nc3ccncc3)c3cccnc3n2)o1] | 1.33 | 303 | ++ | ++ |
| 124 | 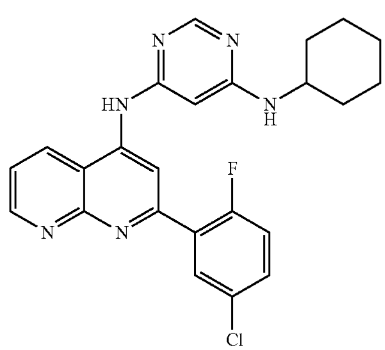 [SMILES: Fc1ccc(Cl)cc1-c1cc(Nc2cc(NC3CCCCC3)ncn2)c2cccnc2n1] | 1.93 | 449 | + | 0 |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 125 | 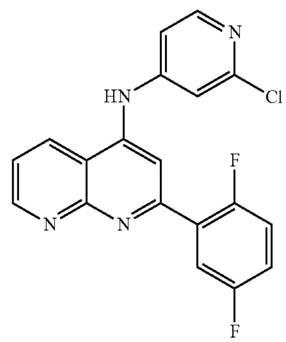 [SMILES: Fc1ccc(F)c(-c2cc(Nc3ccnc(Cl)c3)c3cccnc3n2)c1] | 1.83 | 369 | +++ | + |
| 126 | 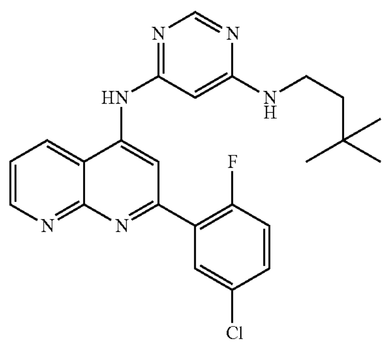 [SMILES: CC(C)(C)CCNc1cc(Nc2cc(-c3cc(Cl)ccc3F)nc3ncccc23)ncn1] | 2.02 | 451 | ++ | ++ |
| 127 | 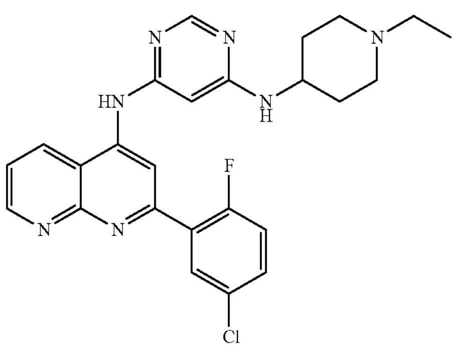 [SMILES: CCN1CCC(Nc2cc(Nc3cc(-c4cc(Cl)ccc4F)nc4ncccc34)ncn2)CC1] | 1.30 | 478 | + | + |
| 128 | 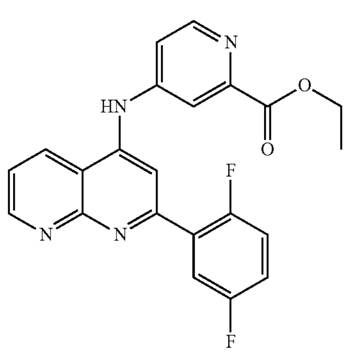 [SMILES: CCOC(=O)c1cc(Nc2cc(-c3cc(F)ccc3F)nc3ncccc23)ccn1] | 1.55 | 407 | 0 | 0 |

TABLE 1-continued

Compounds of formulae (I), (II), (III), (IA)

| No. | Structure | LC-MS M + H+ found | LC-MS R<sub>t</sub> [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 129 | 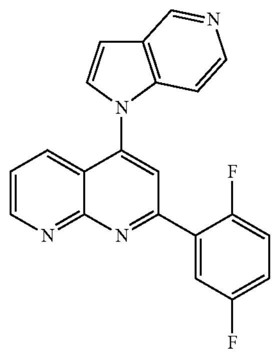 [SMILES: Fc1ccc(F)c(-c2cc(-n3ccc4cnccc43)c3cccnc3n2)c1] | 1.35 | 359 | +++ | ++ |
| 130 | 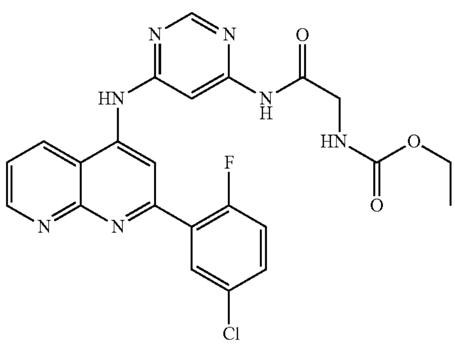 [SMILES: CCOC(=O)NCC(=O)Nc1cc(Nc2cc(-c3cc(Cl)ccc3F)nc3ncccc23)ncn1] | 1.77 | 496 | +++ | +++ |
| 131 | 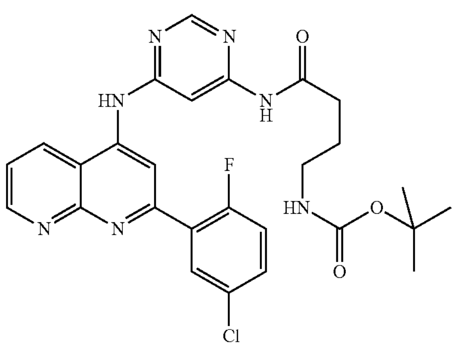 [SMILES: CC(C)(C)OC(=O)NCCCC(=O)Nc1cc(Nc2cc(-c3cc(Cl)ccc3F)nc3ncccc23)ncn1] | 2.04 | 552 | +++ | +++ |
| 132 | 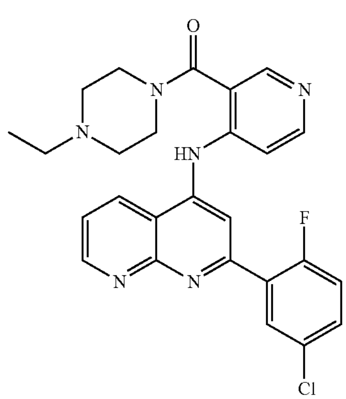 [SMILES: CCN1CCN(C(=O)c2cnccc2Nc2cc(-c3cc(Cl)ccc3F)nc3ncccc23)CC1] | 1.16 | 491 | + | + |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 133 | 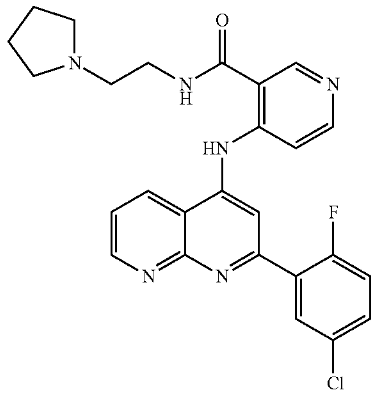 [SMILES: O=C(NCCN1CCCC1)c1cnccc1Nc1cc(-c2cc(Cl)ccc2F)nc2ncccc12] | 1.18 | 491 | +++ | +++ |
| 134 | 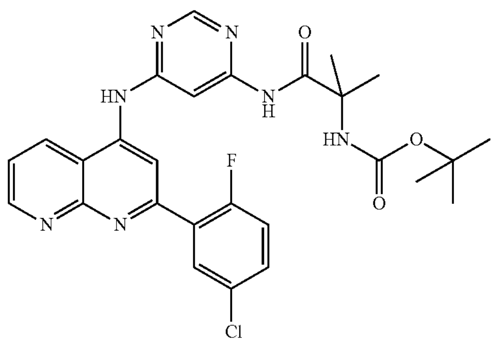 [SMILES: CC(C)(C)OC(=O)NC(C)(C)C(=O)Nc1cc(Nc2cc(-c3cc(Cl)ccc3F)nc3ncccc23)ncn1] | 2.12 | 552 | 0 | 0 |
| 135 | 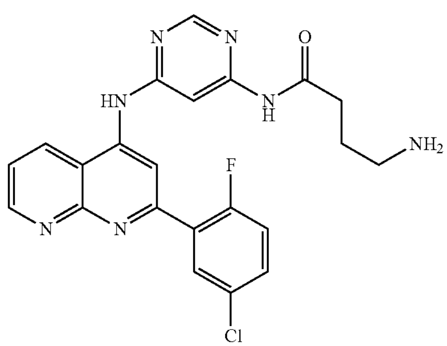 [SMILES: NCCCC(=O)Nc1cc(Nc2cc(-c3cc(Cl)ccc3F)nc3ncccc23)ncn1] | 1.40 | 452 | +++ | ++ |
| 136 | 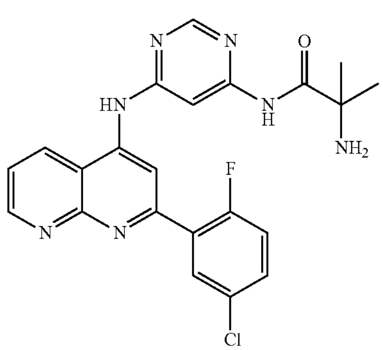 [SMILES: CC(C)(N)C(=O)Nc1cc(Nc2cc(-c3cc(Cl)ccc3F)nc3ncccc23)ncn1] | 1.40 | 452 | ++ | ++ |

TABLE 1-continued

Compounds of formulae (I), (II), (III), (IA)

| No. | Structure | LC-MS M + H+ found | LC-MS R$_t$ [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 137 | 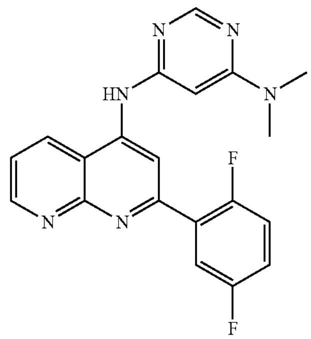 [SMILES: CN(C)c1cc(Nc2cc(-c3cc(F)ccc3F)nc3ncccc23)ncn1] | 1.56 | 379 | 0 | 0 |
| 138 | 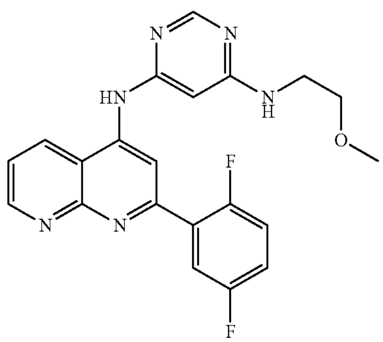 [SMILES: COCCNc1cc(Nc2cc(-c3cc(F)ccc3F)nc3ncccc23)ncn1] | 1.47 | 409 | ++ | ++ |
| 139 | 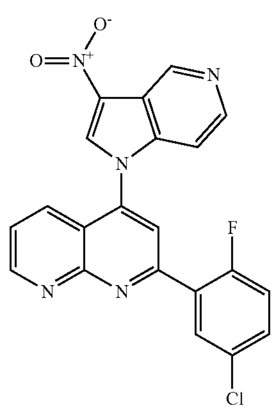 [SMILES: O=[N+]([O-])c1cn(-c2cc(-c3cc(Cl)ccc3F)nc3ncccc23)c2ccncc12] | 1.83 | 420 | +++ | + |
| 140 | 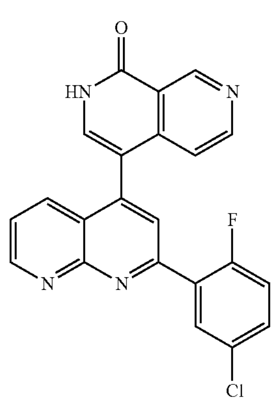 [SMILES: O=c1[nH]cc(-c2cc(-c3cc(Cl)ccc3F)nc3ncccc23)c2ccncc12] | 1.69 | 403 | +++ | +++ |

TABLE 1-continued

Compounds of formulae (I), (II), (III), (IA)

| No. | Structure | LC-MS M + H+ found | LC-MS R_t [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 141 | 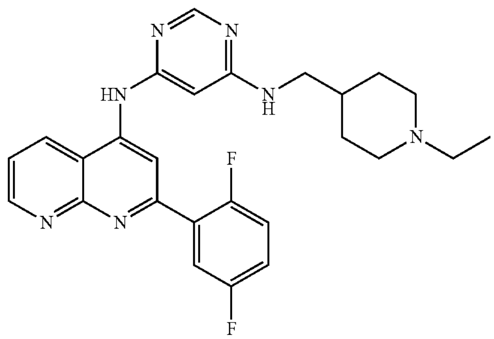 [SMILES: CCN1CCC(CNc2cc(Nc3cc(-c4cc(F)ccc4F)nc4ncccc34)ncn2)CC1] | 1.23 | 476 | +++ | ++ |
| 142 | 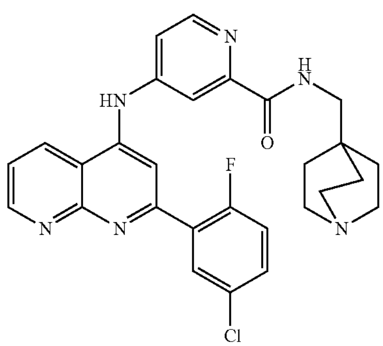 [SMILES: O=C(NCC12CCN(CC1)CC2)c1cc(Nc2cc(-c3cc(Cl)ccc3F)nc3ncccc23)ccn1] | 1.30 | 501 | | |
| 143 | 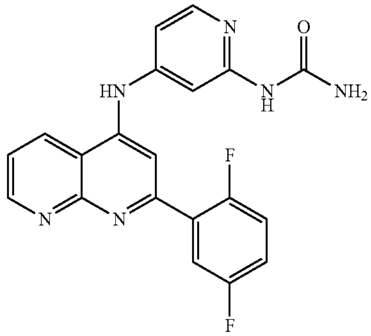 [SMILES: NC(=O)Nc1cc(Nc2cc(-c3cc(F)ccc3F)nc3ncccc23)ccn1] | 1.30 | 393 | +++ | +++ |
| 144 | 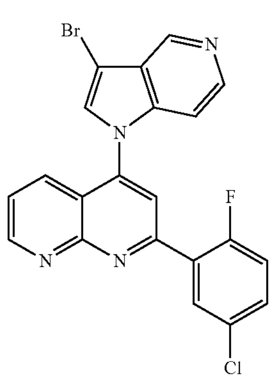 [SMILES: Fc1ccc(Cl)cc1-c1cc(-n2cc(Br)c3cnccc32)c2cccnc2n1] | 1.61 | 454 | +++ | +++ |

TABLE 1-continued

Compounds of formulae (I), (II), (III), (IA)

| No. | Structure | LC-MS M+H+ found | LC-MS R_t [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 145 | 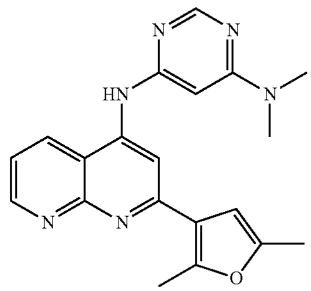 [SMILES: Cc1cc(-c2cc(Nc3cc(N(C)C)ncn3)c3cccnc3n2)c(C)o1] | 1.56 | 361 | 0 | 0 |
| 146 | 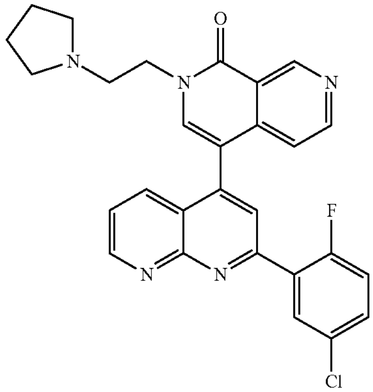 [SMILES: O=c1c2cnccc2c(-c2cc(-c3cc(Cl)ccc3F)nc3ncccc23)cn1CCN1CCCC1] | 1.43 | 500 | ++ | ++ |
| 147 | 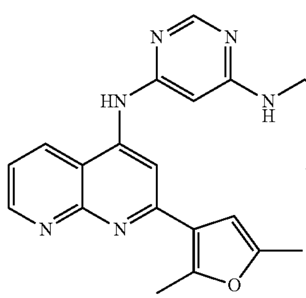 | 1.22 | 430 | + | 0 |
| 148 | 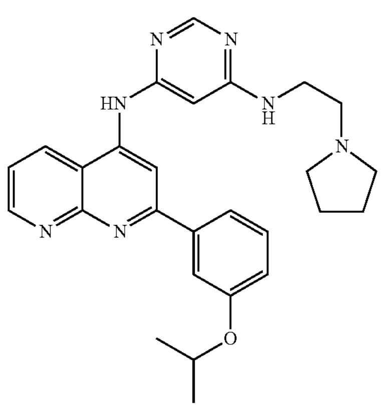 [SMILES: CC(C)Oc1cccc(-c2cc(Nc3cc(NCCN4CCCC4)ncn3)c3cccnc3n2)c1] | 1.39 | 470 | 0 | + |

TABLE 1-continued

Compounds of formulae (I), (II), (III), (IA)

| No. | Structure | LC-MS M + H+ found | LC-MS R<sub>t</sub> [min] method B | TβR activity (example 14) 0 > 10 μM + 1-10 μM ++ 0.1-1 μM +++ <0.1 μM | TβR activity (example 13) 0 > 10 μM + 1-10 μM ++ 0.1-1 μM +++ <0.1 μM |
|---|---|---|---|---|---|
| 149 | 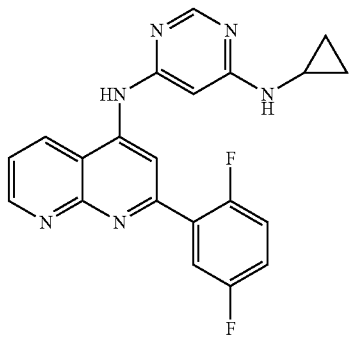 [SMILES: Fc1ccc(F)c(-c2cc(Nc3cc(NC4CC4)ncn3)c3cccnc3n2)c1] | | | | |
| 150 | 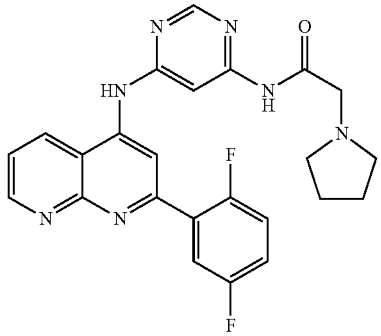 [SMILES: O=C(CN1CCCC1)Nc1cc(Nc2cc(-c3cc(F)ccc3F)nc3ncccc23)ncn1] | | | | |
| 151 | 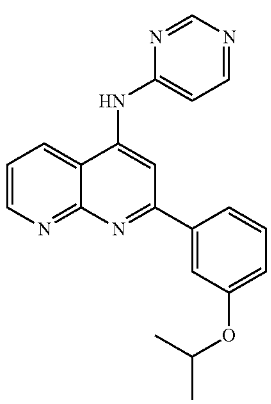 [SMILES: CC(C)Oc1cccc(-c2cc(Nc3ccncn3)c3cccnc3n2)c1] | | | | |
| 152 | 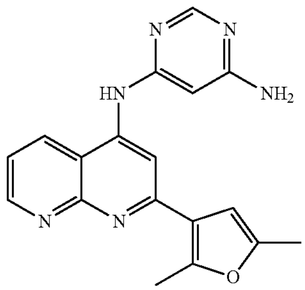 [SMILES: Cc1cc(-c2cc(Nc3cc(N)ncn3)c3cccnc3n2)c(C)o1] | | | | |

Highly preferred embodiments are those compounds of formulae (I) and/or (II) with the nos. 1, 2, 3, 5, 6, 9, 10, 11, 12, 13, 14, 15, 16, 17, 18, 20, 21, 22, 23, 25, 26, 28, 29, 30, 32, 33, 34, 37, 38, 40, 41, 42, 43, 44, 47, 48, 49, 50, 51, 52, 53, 54, 55, 57, 58, 60, 62, 63, 65, 67, 70, 71, 72, 73, 77, 78, 80, 81, 82, 85, 86, 87, 88, 89, 90, 91, 92, 94, 95, 98, 99, 100, 104, 105, 106, 107, 109, 110, 111, 112, 113, 114, 115, 117, 121, 125, 129, 130, 131, 133, 135, 139, 140, 141, 143, 144.

The naphthyridine derivatives according to formula (I) and the starting materials for its preparation, respectively, are produced by methods known per se, as described in the literature (for example in standard works, such as Houben-Weyl, Methoden der organischen Chemie [Methods of Organic Chemistry], Georg-Thieme-Verlag, Stuttgart), i.e. under reaction conditions that are known and suitable for said reactions.

Several references relate to the synthesis of [1,8]naphthyridines. 2-amino nicotinic acid was starting point for 2-alkyl/aryl-3-alkoxycarbonyl-[1,8]naphthyridin-4-one (Zografos, J. Org. Chem. 66(12): 4413-4415 (2001)). Starting material for 2,4-dihydroxy-[1,8]naphthyridine (or its tautomers) can be pyridine that is transformed by amination in position 2, like in a Chichibabin-reaction, giving 2-amino pyridine (McGill, Adv. Heterocycl. Chem. 44: 2-79 (1988)). An intermediate can also be 2-amino nicotinic acid, its esters, its amides or its nitrile or trihalo methyl derivative. Additionally, transformation of a nicotinic acid derivative in position 2, like a halogenation, giving 2-halo nicotinic acid derivatives, for example, will provide the skilled in the art with an appropriate intermediate. An intermediate will have either the amino group in position 2 modified, or the next intermediate can be a reaction product of the 3-carboxylic function equivalent. Several methods starting from 2-aminopyridine describe the synthesis of 2-alkyl[1,8]naphthyridine-4-ones (Naik, BioChemistry (India) 1(3): 126-132 (2007); Naik, Organic Chemistry (India) 3(3): 125-129 (2007); Barlin, Australian J. Chem. 37(5): 1065-1073 (1984)). The synthesis of [1,8]naphthyridines was initially described by Koller, Chem. Ber. 60B: 407-410 (1927) via methyl-2,4-dihydroxy-3-carboxylate, produced by use of 2-amino methyl nicotinate and diethyl malonate, and followed by treatment with strong alkaline base and heat. Work in parallel yielding other [1,8]naphthyridines was conducted by Seide, Chem. Ber. 59: 2465-2473 (1926)). 4-Hydroxy-[1,8]naphthyridine-2-one is described as a side-product in the reaction of 2-aminopyridine with malonic diesters yielding mainly 4-hydroxy-pyrido[1,2-a]pyrimidin-2-one (Abass, Heteroatom Chem. 18(1): 19-27 (2007)). The 4-hydroxy-pyrido pyrimidine-2-one reaction products, can be used for rearrangement to [1,8]naphthyridines or can be rearranged in situ (Schober, J. Heterocyclic Chem. 25(4): 1231-1236 (1988)). Use of 4-hydroxy-[1,8]naphthyridine-2-one (or its tautomers) for novel derivatives and its synthesis is also described (Mohamed, J. Serb. Chem. Soc. 58(12): 1003-1009 (1993)).

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The reactions are preferably performed under basic conditions. Suitable bases are metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia) and several organic bases (piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to water, THF, tert.butanol, tert.amylalcohol, NMP, triethylamine and/or dioxane.

Depending on the conditions used, the reaction time is between a few minutes and 14 days, the reaction temperature is between about −30° C. and 140° C., normally between −10° C. and 130° C., particularly preferably between 30° C. and 125° C.

The present invention also relates to a process for manufacturing compounds of formula (I) comprising the steps of:
(a) reacting a compound of formula (IV)

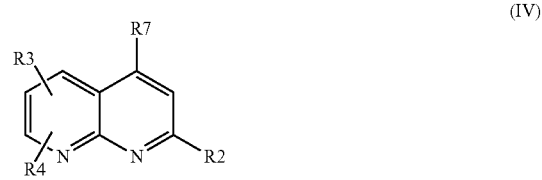

wherein R7 denotes Hal, OY or NYY; and
R2, R3, R4, Hal and Y have the meaning as defined above,
with a compound of formula (V)

wherein X, R1, W1, W2, W3, W5 and W6 have the meaning as defined above under the proviso that R1, R5 together are excluded,
to yield a compound of formula (I)

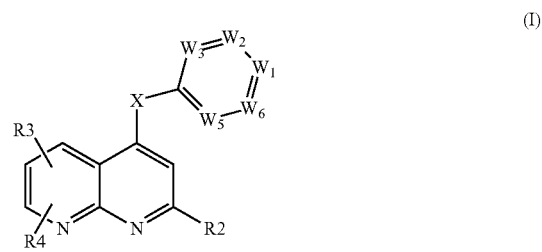

wherein X, R1, R2, R3, R4, W1, W2, W3, W5 and W6 have the meaning as defined above under the proviso that R1, R5 together are excluded,
and optionally
(b) converting a base or an acid of the compound of formula (I) into a salt thereof.

The naphthyridine derivatives of formula (I) are accessible via the route above. The starting materials, including the compounds of formulae (IV) and (V), are usually known to the skilled artisan, or they can be easily prepared by known methods.

Preferred starting materials are compounds of formula (IV-A)

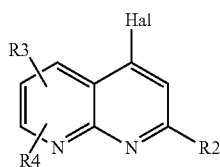

(IV-A)

wherein R2, R3, R4 and Hal have the meaning as defined above.

Another preferred starting material are compounds of formula (IV), particularly compounds of formula (IV-A), wherein R2 denotes phenyl or pyridyl, each of which can be substituted by at least one substituent selected from the group of A, Hal, CN, NYY, OY, =O; and R3, R4, R7, Hal and Y have the meaning as defined above.

In particular, the compounds of formula (IV-A) are accessible via two different routes. In a first embodiment of the synthesis routes, the compounds of formula (IV-A) can be prepared by a process (A) comprising the steps of:
(a) reacting a compound of formula (VI)

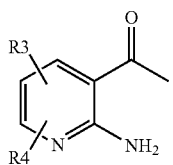

(VI)

wherein R3 and R4 have the meaning as defined above,
in an alkaline milieu with a compound of formula (VII)

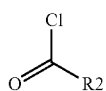

(VII)

wherein R2 has the meaning as defined above,
to yield a compound of formula (VIII)

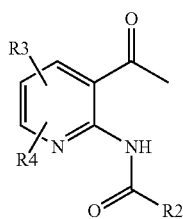

(VIII)

wherein R2, R3 and R4 have the meaning as defined above, (b) reacting the compound of formula (VIII) in an alkaline milieu to yield a compound of formula (IX)

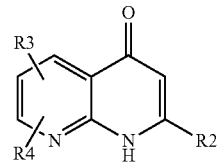

(IX)

wherein R2, R3 and R4 have the meaning as defined above,
(c) reacting the compound of formula (IX) with a halogenating agent to yield a compound of formula (IV-A)

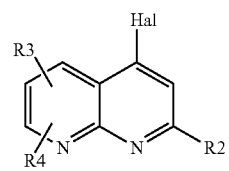

(IV-A)

wherein R2, R3, R4 and Hal have the meaning as defined above,
and optionally
(d) converting a base or an acid of the compound of formula (IV-A) into a salt thereof.

In more detail, starting from 2-amino-3-acetyl pyridine of formula (VI) by acetylating reaction with a benzoic aryl/hetaryl derivative of formula (VII), like 6-methylpyridine-2-carboxylic acid chloride, an 2-aroylamido-3-acetyl pyridine of formula (VIII), like 6-methylpyridine-2-carboxylic acid-(3-acetyl-pyridin-2-yl)-amide, is obtained, which cyclizes under treatment with a strong base, preferably KOBut, to give 2-aryl/hetaryl-[1,8]naphtyridine-4-ones of formula (IX), like 2-(6-Methyl-pyridin-2-yl)-1H-[1,8]naphthyridin-4-one. Halogenation with SOHal$_2$, SO$_2$Hal$_2$, POHal$_3$ and/or PHal$_5$, wherein Hal has the meaning as defined above, preferably Cl or Br, more preferably POCl$_3$, gives a reactive intermediate of formula (IV-A). The latter is used for strong base-catalyzed, preferably KOBut-catalyzed, and/or Pd0-catalyzed couplings of anilines or hetarylamines of formula (V), particularly amino-pyridines, amino-pyrimidines like 4,6-diamino pyrimidine, or amino-triazines, like in a Buchwald-Hartwig reaction, to give final compounds of type (I), like [2-(6-methyl-pyridin-2-yl)-[1,8]naphthyridin-4-yl]-(6-methyl-pyrimidin-4-yl)-amine.

In a second embodiment of the synthesis routes, the compound of formula (IV-A) can be prepared by another process (B) comprising the steps of:
(a) reacting a halogenating agent with a compound of formula (X)

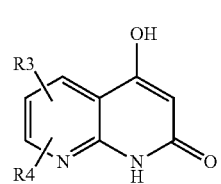

(X)

wherein R3 and R4 have the meaning as defined above, to yield a compound of formula (XI)

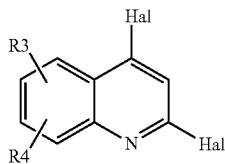
(XI)

wherein R3, R4 and Hal have the meaning as defined above, (b) reacting the compound of formula (XI) with a compound selected from the group of boronic acid, boronic ester, tin organics and boron triflates, each of which is substituted by R2 having the meaning as defined above, to yield a compound of formula (IV-A)

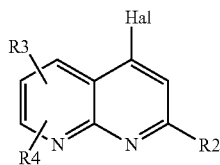
(IV-A)

wherein R2, R3, R4 and Hal have the meaning as defined above, and optionally (c) converting a base or an acid of the compound of formula (IV-A) into a salt thereof.

In more detail, 4-hydroxy-[1,8]naphthyridinone of formula (X), or its tautomers, is transferred to 2,4-halo-[1,8] naphthyridine of formula (XI) by treatment with one or more halogenating agents, preferably $POCl_3$ or $POBr_3$ and/or the corresponding $PHal_5$, wherein Hal has the meaning as defined above. Treatment of 2,4-dihalo-[1,8]naphthyridine of formula (X) using Pd0 catalysis with a boronic acid or boronic ester type (i), or similar chemistries with tin organics type (ii), or boron triflates type (iii), yields a 2-aryl/hetaryl-4-halo-[1,8]naphthyridine of formula (IV-A). The latter can be reacted with an aniline/hetaryl-amine of formula (V) to give a 2-aryl/hetaryl-4-hetarylamino-[1,8]naphthyridine, like 2-(2-fluoro, 5-chloro phenyl)-4-(3-methoxy-pyridyl)-4-amino-[1,8] naphthyridine.

The starting materials of process (B), including the compound of formula (X), are usually known to the skilled artisan, or they can be easily prepared by known methods. In particular, the compounds of formula (X) are accessible via different routes. In a first embodiment of the synthesis routes, the compounds of formula (X) can be prepared by a process (C) comprising the steps of:

(a) reacting an acetylating agent with a compound of formula (XII)

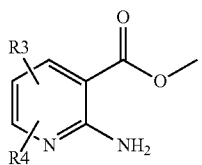
(XII)

wherein R3 and R4 have the meaning as defined above, to yield a compound of formula (XIII)

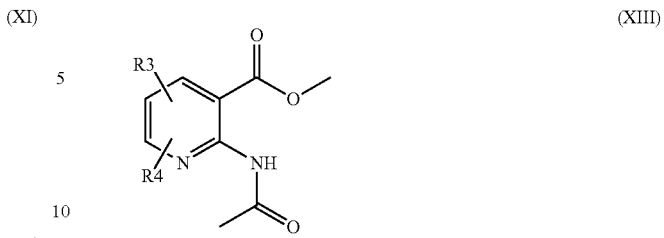
(XIII)

wherein R3 and R4 have the meaning as defined above, (b) reacting the compound of formula (XIII) under basic conditions to yield a compound of formula (X) or a tautomer of formula (X-A)

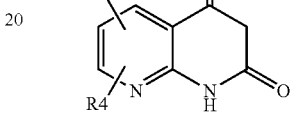
(X-A)

wherein R3 and R4 have the meaning as defined above, and optionally (c) converting a base or an acid of the compound of formula (X-A) into a salt thereof.

In more detail, starting from nicotinic esters of formula (XII), prepared from nicotinic acid by esterification, by reaction with acetylating agents, preferably AcOEt, AcCl, $Ac_2O$, Ac-imidazole, acetyl morpholine, Ac—CN or acetic acid, under coupling (dehydrating) conditions, acetamido nicotinic ester derivatives of formula (XIII) are obtained, which can be cyclized under basic conditions, e.g. by use of $KN(SiMe_3)_2$ in a solvent like THF and/or toluene, to yield tetrahydro-[1,8] naphthyridine-2,4-diones of formula (X), or tautomeric forms of formula (X-A) to be processed further like in process B.

The esters of formula (XII) can be produced via alcoholysis of a compound of formula (XXIII),

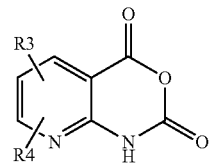
(XXIII)

wherein R3 and R4 have the meaning as defined above, which can be generated from acids by phosgenation techniques.

In a second embodiment of the synthesis routes, the compounds of formula (X) can be prepared by a process (D) comprising the steps of:

(a) reacting a compound of formula (XII)

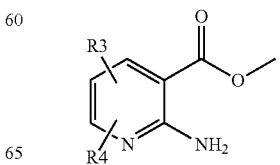
(XII)

wherein R3 and R4 have the meaning as defined above, with a compound of formula (XIV)

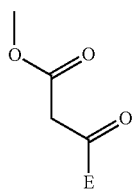
(XIV)

wherein E denotes OY or NYY; and Y has the meaning as defined above,
to yield a compound of formula (XV)

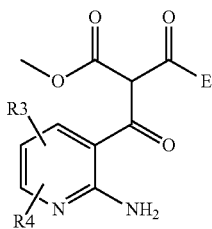
(XV)

wherein E denotes OY or NYY; and
Y, R3 and R4 have the meaning as defined above,
(b) reacting the compound of formula (XV) in a solvent and under alkaline condition to yield a compound of formula (XVI)

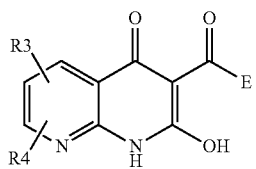
(XVI)

wherein E denotes OY or NYY; and
Y, R3 and R4 have the meaning as defined above,
(c) reacting the compound of formula (XVI) under acidic or alkaline conditions to yield the compound of formula (X) or a tautomer of formula (X-B)

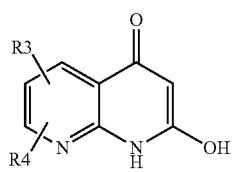
(X-B)

wherein R3 and R4 have the meaning as defined above, and optionally
(c) converting a base or an acid of the compound of formula (X-B) into a salt thereof.
In more detail, starting from nicotinic acid ester of formula (XII) and reaction with malonic acid derivatives of formula (XIV) in the presence of a solvent and a base, acyl malonic acid derivatives of formula (XV) are formed, which can be cyclized under basic conditions in a solvent to form tetrahydro-[1,8]naphthyridine-2,4-dione-3-carboxylic acid derivatives or its tautomeric forms of formula (XVI). After acidic or alkaline hydrolysis/saponification and decarboxylation, 2-hydroxy-[1,8]naphthyridine-4-one of formula (X-B), or its tautomers, is formed, which can be further processed like in method B. Alternatively, the naphthyridine-ones of formulae (X), (X-A) and (X-B) can be obtained from reaction of a corresponding pyridin-4-yl-amine with malonic acid ester chloride (i.e. MeOCOCH$_2$COCl) or diethyl malonate (i.e. CH$_2$(COOEt)$_2$), followed by saponification, e.g. with NaOH, and cyclization mediated by polyphosphoric acid (PPA).

In another aspect of manufacturing the naphthyridine derivative of formula (I), compounds under formula (V) are accessible via the following route. In a first embodiment of the synthesis route, 2-substituted 4-amino pyridines under formula (V) can be prepared by a process (E) comprising the steps of:

(a) reacting 2-bromo-4-nitro-pyridine-N-oxide with a compound of formula H—R6, wherein R6 has the meaning as defined above, to yield a compound of formula (XVII)

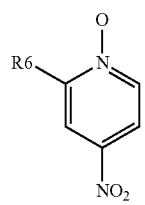
(XVII)

wherein R6 has the meaning as defined above,
(b) reacting the compound of formula (XVII) under reducing conditions to yield a compound of formula (V-A)

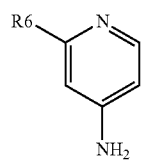
(V-A)

wherein R6 has the meaning as defined above,
and optionally
(c) converting a base or an acid of the compound of formula (V-A) into a salt thereof.

In more detail, synthesis of 2-substituted 4-amino pyridines starts, for example, from commercial 2-bromo-4-nitro-pyridine-N-oxide, which is reacted with an alcohol, phenol, amine or aniline under basic conditions to give the compound of formula (XVII), like ethers or amines, which can be reduced to the corresponding 4-amino pyridine derivatives of formula (V-A).

In a second embodiment of the synthesis route, the 3-substituted 4-amino-pyridines under formula (V) can be prepared by a process (F) comprising the steps of:
(a) reacting 3-fluoro-4-nitro-pyridine-N-oxide or the corresponding 3-bromo derivative with a compound of formula H—R5, wherein R5 has the meaning as defined above, to yield a compound of formula (XVII)

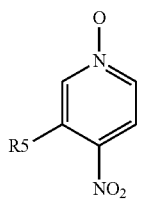

(XVIII)

wherein R5 has the meaning as defined above,
(b) reacting the compound of formula (XVIII) under reducing conditions to yield a compound of formula (V-B)

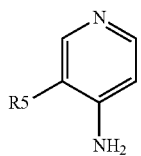

(V-B)

wherein R5 has the meaning as defined above,
and optionally
(c) converting a base or an acid of the compound of formula (V-B) into a salt thereof.

In more detail, synthesis of 3-substituted 4-amino pyridines starts, for example, from commercial 3-fluoro 4-nitro-pyridine-N-oxide or the corresponding 3-bromo derivative, which is reacted with an alcohol, phenol, amine or aniline under basic conditions to give the intermediate of formula (XVIII), like ethers or amines, which can be reduced to the corresponding 3-substituted 4-amino pyridine derivatives of formula (V-B).

Accordingly, any compound of formulae (IV) to (XVIII) can be purified, provided as intermediate product and used as starting material for the preparation of compounds of formula (I). It is preferred, however, that the compounds of formulae (IV), (V), (IX), (X) and/or (XI), or sub-formulae thereof, are provided as intermediate product and used as starting material for the preparation of compounds of formula (I), more preferably the compounds of formulae (IV), (V), (IX) and/or (XI), or sub-formulae thereof, most preferably the compounds of formulae (IV) and/or (V), or sub-formulae thereof. Highly preferred template intermediates for producing the compounds of formula (I) are selected from the group of:

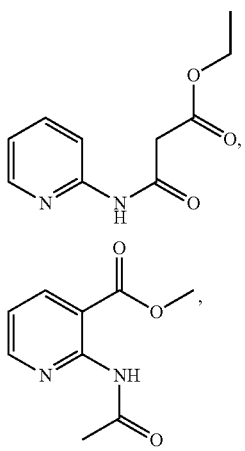

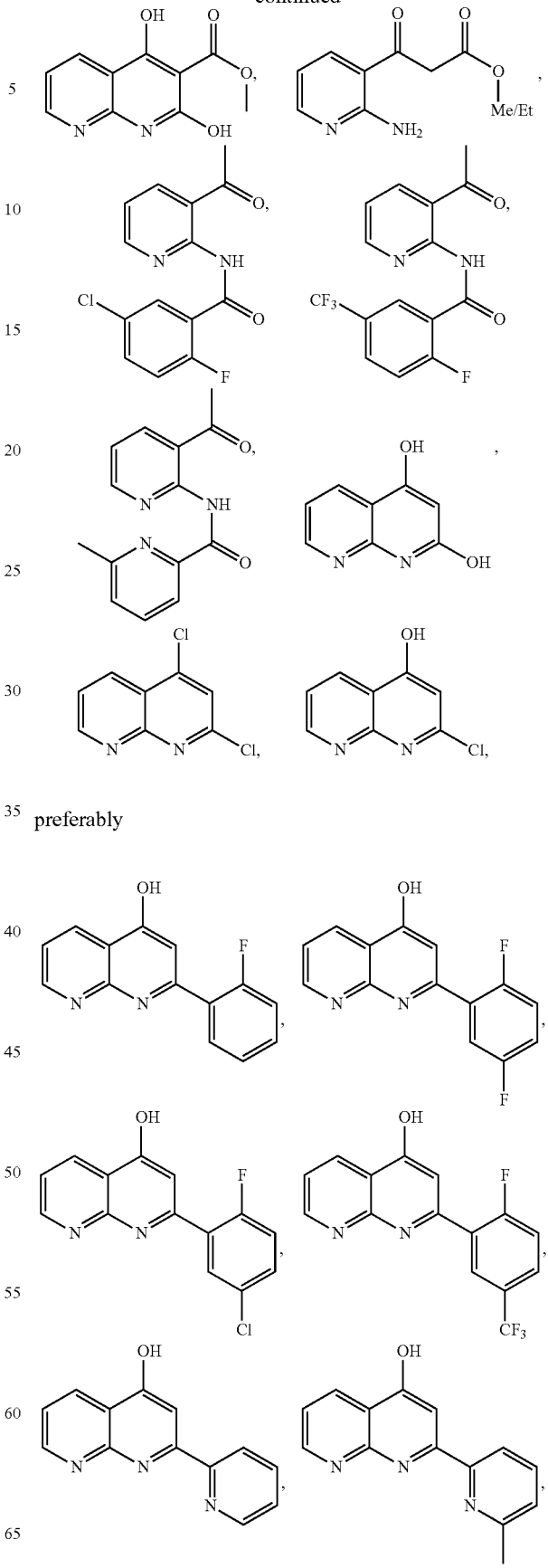

preferably

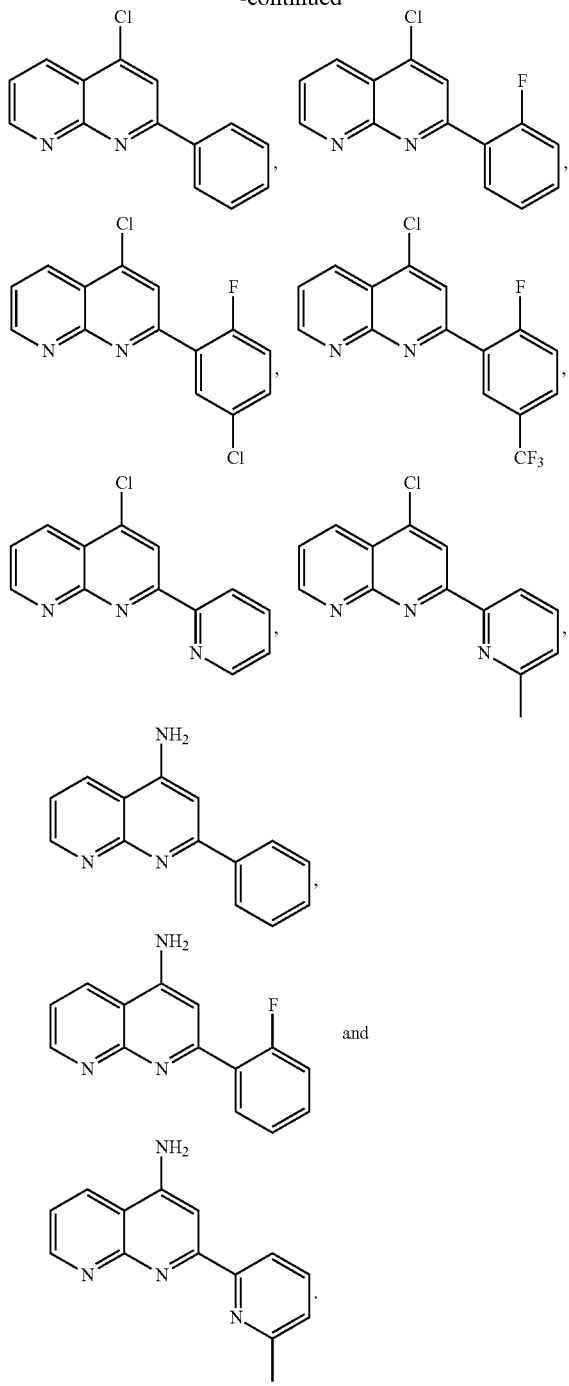

The invention also relates to intermediate compounds of formula (IV), wherein R2 denotes phenyl or pyridyl, each of which can be substituted by at least one substituent selected from the group of A, Hal, CN, NYY, OY, =O; and R3, R4, R7, Hal and Y have the meaning as defined above, under the proviso that (i) unsubstituted phenyl is disclaimed if R7 is OY and (ii) unsubstituted pyridyl is disclaimed if R7 is NYY. Said compounds of formula (IV) can be prepared by another process (B') comprising the steps of:

(a) reacting a compound selected from the group of boronic acid, boronic ester, tin organics and boron triflates, each of which is substituted by R2 having the meaning as defined above, with a compound of formula (XI-A)

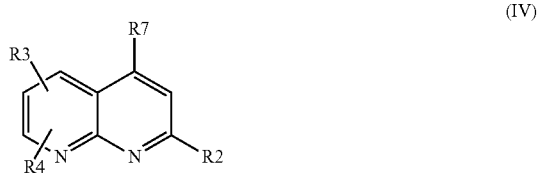

(XI-A)

wherein R3, R4; R7 and Hal have the meaning as defined above,
to yield a compound of formula (IV)

(IV)

wherein R2 denotes phenyl or pyridyl, each of which can be substituted by at least one substituent selected from the group of A, Hal, CN, NYY, OY, =O; and R3, R4, R7, Hal and Y have the meaning as defined above, under the proviso that (i) unsubstituted phenyl is disclaimed if R7 is OY and (ii) unsubstituted pyridyl is disclaimed if R7 is NYY, and optionally (c) converting a base or an acid of the compound of formula (IV) into a salt thereof.

The reaction of the compound of formula (IV) with the compound of formula (V) results in the addition to the compound of formula (I). In more detail, the compound of formula (IV) can be reacted with a compound of formula (V) using a strong base, preferably KOBut, or Pd0 chemistry, like in a Buchwald-Hartwig reaction, to produce a compound of formula (I). Preferably, aniline under formula (V) is reacted to produce final parent compound of 2-R2-4-Het-amino-[1,8] naphthyridine, wherein R2 and Het have the meaning as defined above.

The compounds of formula (I) can be modified, like hydrogenated or metal-reduced, to remove the chlorine, or put into a substitution reaction, and/or to be transformed with an acid or base into a salt, preferably with a strong acid. Numerous papers and methods are available and useful for the one skilled in the art in respect for organic chemistry, chemical strategies and tactics, synthetic routes, protection of intermediates, cleavage and purification procedure, isolation and characterization. General chemical modifications are known to the one skilled in the art. Halogenation of aryls or hydroxy substitution by halogens of acids, alcohols, phenols, and their tautomeric structures can be preferably carried out by use of POCl$_3$, or SOCl$_2$, PCl$_5$, SO$_2$Cl$_2$. In some instances oxalyl chloride is also useful. Temperatures can vary from 0° C. to reflux depending on the task to halogenate a pyridone structure or a carboxylic acid or an sulfonic acid. Time will also be adjusted from minutes to several hours or even over night. Similarly, alkylation, ether formation, ester formation, amide formation are known to the one skilled in the art. Arylation with aryl boronic acids can be performed in presence of a Pd catalyst, appropriate ligand and base, preferably a carbonate, phosphate, borate salt of sodium, potassium or cesium. Organic bases, like Et$_3$N, DIPEA or the more basic DBU can also be used. Solvents can vary too, from toluene, dioxane, THF, diglyme, monoglyme, alcohols, DMF, DMA, NMP, acetonitrile, in some cases even water, and others. Commonly used catalysts like Pd (PPh$_3$)$_4$, or Pd(OAc)$_2$, PdCl$_2$ type precursors of Pd0 catalysts have advanced to more complex ones with more efficient ligands. In C—C arylations instead of boronic acids and esters (Stille coupling), aryl-trifluoroborate potassium salts (Suzuki-Miyaura coupling), organo silanes (Hiyama coupling), Grignard reagents (Kumada), zink organyles (Negishi coupling) and tin organyles (Stille coupling) are useful. This experience can be transferred to N- and O-arylations. Numerous papers and methods are available and useful for the one skilled in the art in respect of N-arylation and even of electron deficient anilines (Biscoe et al. JACS 130: 6686 (2008)), and with aryl chlorides and anilines (Fors et al. JACS 130: 13552 (2008) as well as for O-arylation by using Cu catalysis and Pd catalysis.

In a synthetic approach to 3-substituted 4-amino N-heteroaryl-[1,8]naphthyridines, the modified compounds under formula (I) can be prepared by a process (G) comprising the steps of:
(a) reacting a compound of formula (XIX)

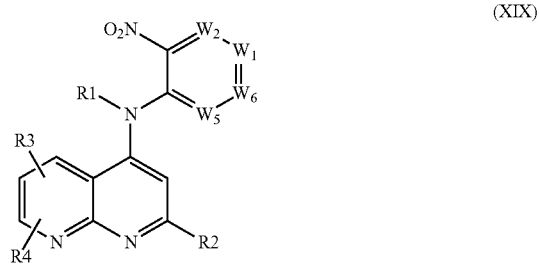

(XIX)

wherein W1, W2, W5, W6, R1, R2, R3 and R4 have the meaning as defined above, under reducing conditions to yield a compound of formula (XX)

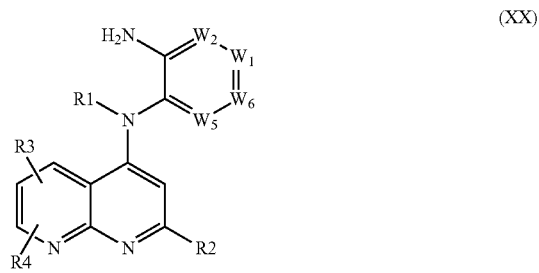

(XX)

wherein W1, W2, W5, W6, R1, R2, R3 and R4 have the meaning as defined above,
(b) reacting the compound of formula (XX) under acylating conditions to yield a compound of formula (XXI)

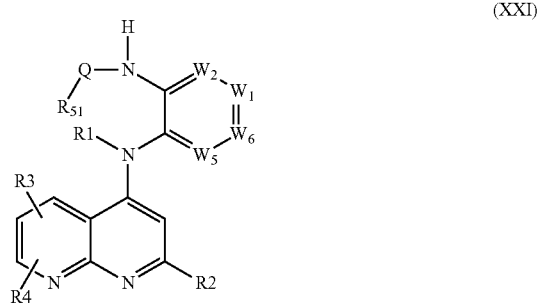

(XXI)

wherein Q denotes —CO—, —SO$_2$—, —NY—CO—, —CO—NY—, —OCO—, NY—SO$_2$ or a bond; R51 denotes Y, -Alk-NYY, -Alk-OY, Het$^3$, —CO—R2 or —CO-Het$^2$; and W1, W2, W5, W6, R1, R2, R3, R4, Y, Alk, Het$^2$ and Het$^3$ have the meaning as defined above,
(c) reacting the compound of formula (XXI) under acylating conditions, followed by acidic conditions, to yield a compound of formula (XXII)

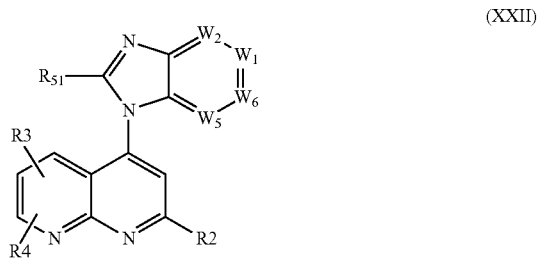

(XXII)

wherein R51 denotes Y, -Alk-NYY, -Alk-OY, Het$^3$, —CO—R2 or —CO-Het$^2$; and W1, W2, W5, W6, R2, R3, R4, Y, Alk, Het$^2$ and Het$^3$ have the meaning as defined above,
and optionally
(d) converting a base or an acid of the compound of formula (XXII) into a salt thereof.

In more detail, 3-nitro-pyridin-4-yl-amine and similar derivatives can be used to synthesize 2-R2-4-(3-nitro-pyridyl-4-amino)-naphthyridines of formula (XIX), like [2-(2-fluoro-5-trifluoro-methyl-phenyl)-[1,8]naphthyridin-4-yl]-(3-nitro-pyridin-4-yl)-amine, from an appropriate intermediate of formula (IV), like 4-chloro-2-(2-fluoro-5-trifluoromethyl-phenyl)-[1,8]naphthyridine, under basic conditions, like with aid of KOBut or under Pd0 catalysis. After reduction of the 3-nitro function, the 3-amino compound can be modified, like alkylated, carbaminated, sulfamidated, sulfamoylated, or acylated and consecutively benzimidazoylated by ring closure utilising both 3- and 4-amino groups. Particularly, the compound of formula (XX) is reacted under acylating conditions with an activated carboxylic acid derivative, particularly a chloride, anhydride, active ester, an activated sulfonic acid derivative, a carbonate or an isocyanate. Subsequently, the resulting compound of formula (XXI) is reacted under acylating conditions with an activated carboxylic acid derivative, followed by acid treatment to cyclize the initially formed amide to the corresponding imidazole.

Alternatively, a ring closure reaction with carbonic acid derivatives, preferably carbonyl diimidazole, can be used for cyclic urea synthesis, like for 1-[2-(2-fluoro-5-trifluoromethyl-phenyl)-[1,8]naphthyridin-4-yl]-1,3-dihydro-imidazo[4,5-c]pyridin-2-one, comprising the steps of:
(a) reacting the compound of formula (XX) with a carbonic acid derivative to yield a compound of formula (XXII-A)

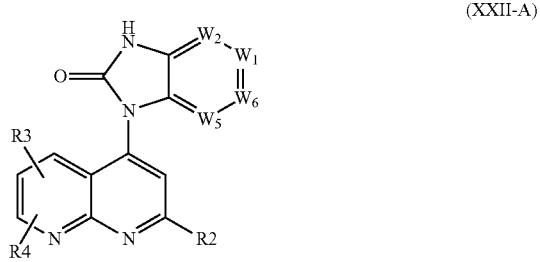

(XXII-A)

and optionally
(b) converting a base or an acid of the compound of formula (XXII-A) into a salt thereof.

In the final step of the processes above, a salt of the compound according to formulae (I) to (XXII), preferably formula (I), is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminum salts of the compounds according to the invention are likewise included. In the case of certain compounds according to the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Object of the present invention is also the use of compounds according to formula (I) and/or physiologically acceptable salts thereof for inhibiting ATP consuming proteins, particularly kinases. The term "inhibition" denotes any reduction in kinase activity, which is based on the action of the specific inventive compounds capable to interact with the target kinase in such a manner that makes recognition, binding and blocking possible. The compounds are characterized by such a high affinity to at least one kinase, which ensures a reliable binding and preferably a complete blocking of kinase activity. More preferably, the substances are mono-specific in order to guarantee an exclusive and directed recognition with the chosen single kinase target. In the context of the present invention, the term "recognition"—without being limited thereto—relates to any type of interaction between the specific substances and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

In an embodiment of the present invention, the kinases either belong to the group of tyrosine kinases and serine/threonine kinases. In a preferred embodiment of the invention, the kinases are selected form the group of TGF-beta, PDK1, Met, PKD1, MINK1, SAPK2-alpha, SAPK2-beta, MKK1, GCK, HER4, ALK1, ALK2, ALK4, ALK5 and TbR type II. It is more preferred to inhibit serine/threonine kinases. The most preferred kinase to be inhibited is TGF-beta receptor kinase.

The kinase are especially half inhibited if the concentration of the compounds amounts to less than 10 µM, preferably less than 1 µM, more preferably less than 0.1 µM. Such concentration is also referred to as IC50.

The compounds according to the invention preferably exhibit an advantageous biological activity, which is easily demonstrated in enzyme-based assays, for example assays as described herein. In such enzyme-based assays, the compounds according to the invention preferably exhibit and cause an inhibiting effect, which is usually documented by IC50 values in a suitable range, preferably in the micromolar range and more preferably in the nanomolar range.

As discussed herein, these signaling pathways are relevant for various diseases. Accordingly, the compounds according to the invention are useful in the prophylaxis and/or treatment of diseases that are dependent on the said signaling pathways by interaction with one or more of the said signaling pathways. The present invention therefore relates to compounds according to the invention as promoters or inhibitors, preferably as inhibitors, of the signaling pathways described herein, preferably of the TGF-β signaling pathway.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilized in order to modulate the signal (e.g. Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-Gonzalez, R. and Glenney, Jr., J. R. 1992, J. Biol. Chem. 267, page 14535).

For the identification of kinase inhibitors, various assay systems are available. In scintilla-tion proximity assay (Sorg et al., J. of Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214). Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody.

The use according to the previous paragraphs of the specification may be either performed in-vitro or in-vivo models. The inhibition can be monitored by the techniques described in the course of the present specification. The in-vitro use is preferably applied to samples of humans suffering from cancer, tumor growth, metastatic growth, fibrosis, restenosis, HIV infection, neurodegenartive disorders, e.g. Alzheimer's disease, atherosclerosis, inflammation and disorders of wound healing, angiogenesis, cardiovascular system, bone, CNS and/or PNS. Testing of several specific compounds and/or derivatives thereof makes the selection of that active ingredient possible that is best suited for the treatment of the human subject. The in-vivo dose rate of the chosen derivative is advantageously pre-adjusted to the kinase susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of kinase activity if expedient.

The invention furthermore relates to a medicament comprising at least one compound according to the invention and/or pharmaceutically usable derivatives, salts, solvates and stereoisomers thereof, including mixtures thereof in all ratios, and optionally excipients and/or adjuvants.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Consequently, the invention also relates to a pharmaceutical composition comprising as active ingredient an effective amount of at least one compound according to formula (I) and/or physiologically acceptable salts thereof together with pharmaceutically tolerable adjuvants.

A "medicament", "pharmaceutical composition" or "pharmaceutical formulation" in the meaning of the invention is any agent in the field of medicine, which comprises one or more compounds of formula (I) or preparations thereof and can be used in prophylaxis, therapy, follow-up or aftercare of patients who suffer from diseases, which are associated with kinase activity, in such a way that a pathogenic modification of their overall condition or of the condition of particular regions of the organism could establish at least temporarily. Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

The present compounds are suitable for combination with known anticancer agents. These known anticancer agents include the following: (1) estrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors. The present compounds are particularly suitable for administration at the same time as radiotherapy. The synergistic effects of inhibiting VEGF in combination with radiotherapy have been described in the art (see WO 00/61186).

The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, e.g. lactose or starch, magnesium stearate, talc and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is orally or parenterally administered, more preferably orally. In particular, the active ingredient is provided in a water-soluble form, such as a pharmaceutically acceptable salt, which is meant to include both acid and base addition salts. Furthermore, the compounds of formula (I) and salts thereof, may be lyophilized and the resulting lyophilizates used, for example, to produce preparations for injection. The preparations indicated may be sterilized and/or may comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases, cancer and/or fibrotic diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by kinase activity. It is particularly preferred that the diseases are selected from the group of cancer, tumor growth, metastatic growth, fibrosis, restenosis, HIV infection, neurodegenerative disorders, atherosclerosis, inflammation and disorders of wound healing, angiogenesis, cardiovascular system, bone, CNS and/or PNS. It shall be understood that the host of the compound is included in the present scope of protection according to the present invention. Particular preference is given to the treatment and/or monitoring of a tumor and/or cancer disease. The tumor is preferably selected from the group of tumors of the squamous epithelium, bladder, stomach, kidneys, head, neck, esophagus, cervix, thyroid, intestine, liver, brain, prostate, urogenital tract, lymphatic system, larynx and/or lung.

The tumor is furthermore preferably selected from the group of lung adenocarcinoma, small-cell lung carcinomas, pancreatic cancer, glioblastomas, colon carcinoma and breast carcinoma. In addition, preference is given to the treatment and/or monitoring of a tumor of the blood and immune system, more preferably for the treatment and/or monitoring of a tumor selected from the group of acute myeloid leukemia, chronic myeloid leukemia, acute lymphatic leukemia and/or chronic lymphatic leukemia. Such tumors can also be designated as cancers in the meaning of the invention.

In a more preferred embodiment of the invention, the aforementioned tumors are solid tumors.

In another preferred embodiment of the invention, the compounds of formula (I) are applied for the prophylactic or therapeutic treatment and/or monitoring of retroviral diseases or for the manufacture of a medicament for the prophylactic or therapeutic treatment and/or monitoring of retroviral diseases, respectively, preferably of retroviral immune diseases, more preferably an HIV infection. The agent can be either administered to reducing the likelihood of infection or to prevent the infection of a mammal with a retrovirus and the onset of the disease in advance, or to treat the disease caused by the infectious agent.

Particularly, later stages of virus internalization can be reduced and/or prevented. It is the intention of a prophylactic inoculation to reduce the likelihood of infection or to prevent the infection with a retrovirus after the infiltration of single viral representatives, e.g. into a wound, such that the subsequent propagation of the virus is strictly diminished, or it is even completely inactivated. If an infection of the patient is already given, a therapeutic administration is performed in order to inactivate the retrovirus being present in the body or to stop its propagation. Numerous retroviral diseases can be successfully combated by applying the inventive compounds, particularly AIDS caused by HIV.

The naphthyridine compounds according to the present invention are also useful against diseases selected from the group of cardiovascular diseases, kidney diseases, hepatic diseases, syndromes associated with pulmonary fibrosis, collagen vascular disorders, eye diseases, excessive or hypertrophic scar formation in the dermis, disorders of the gastrointestinal tract, chronic scarring of the peritoneum, neurological conditions, diseases of the joints, diseases that benefit from the improvement of lung function and diseases from a proinflammation response, fibroproliferative response or both.

The invention also relates to the use of compounds according to formula (I) and/or physiologically acceptable salts thereof for the prophylactic or therapeutic treatment and/or monitoring of diseases that are caused, mediated and/or propagated by kinase activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by kinase activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

In another embodiment of the present invention, the compounds according to formula (I) and/or physiologically acceptable salts thereof are used for the production of a combination preparation for the prophylactic or therapeutic treatment and/or monitoring of solid tumors, wherein the combination preparation comprises an effective amount of an active ingredient selected from the group of (1) estrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors.

The compounds of formula (I) according to the invention can be administered before or following an onset of disease once or several times acting as therapy. The aforementioned medical products of the inventive use are particularly used for the therapeutic treatment. A therapeutically relevant effect relieves to some extent one or more symptoms of an autoimmune disease, or returns to normality, either partially or completely, one or more physiological or biochemical parameters associated with or causative of the disease or pathological conditions. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disease or even prevent the initiation of diseases associated with increased kinase activity in advance or to treat the arising and continuing symptoms. The diseases as concerned by the invention are preferably cancer and/or fibrotic diseases. In the meaning of the invention, prophylactic treatment is advisable if the subject possesses any preconditions for the aforementioned physiological or pathological conditions, such as a familial disposition, a genetic defect, or a previously passed disease. The prior teaching of the present specification concerning the pharmaceutical composition is valid and applicable without restrictions to the use of compounds according to formula (I) and their salts for the production of a medicament and/or combination preparation for prophylaxis and therapy of said diseases.

It is another object of the invention to provide a method for treating diseases that are caused, mediated and/or propagated by kinase activity, wherein an effective amount of at least one compound according to formula (I) and/or physiologically acceptable salts thereof is administered to a mammal in need of such treatment. The preferred treatment is an oral or parenteral administration. The treatment of the patients with cancer, tumor growth, metastatic growth, fibrosis, restenosis, HIV infection, neurodegenerative disorders, atherosclerosis, inflammation and disorders of wound healing, angiogenesis, cardiovascular system, bone, CNS and/or PNS, or people bearing a risk of developing such diseases or disorders on the basis of existing preconditions by means of the compounds of formula (I) improves the whole-body state of health and ameliorates symptoms in these individuals. The inventive method is particularly suitable for treating solid tumors. In a preferred embodiment of the method, the treatment with the present compounds is combined with radiotherapy. It is even more preferred to administer a therapeutically effective amount of a compound according formula (I) in combination with radiotherapy and another compound from the groups (1) to (10) as defined above. The synergistic effects of inhibiting VEGF in combination with radiotherapy have already been described. The prior teaching of the invention and its embodiments is valid and applicable without restrictions to the method of treatment if expedient.

In the scope of the present invention, novel hetarylaminonaphthyridine compounds of formula (I) are provided for the first time. The inventive compounds strongly and/or selectively target ATP consuming proteins like kinases, particularly TGF-β receptor kinases. The compounds of formula (I) and derivatives thereof are characterized by a high specificity and stability; low manufacturing costs and convenient handling. These features form the basis for a reproducible action, wherein the lack of cross-reactivity is included, and for a reliable and safe interaction with their matching target structures. The current invention also comprises the use of present hetarylaminonaphthyridine derivatives in the inhibition, the regulation and/or modulation of the signal cascade of kinases, especially the TGF-β receptor kinases, which can be advantageously applied as research and/or diagnostic tool.

Furthermore, medicaments and pharmaceutical compositions containing said compounds and the use of said compounds to treat kinase-mediated conditions is a promising, novel approach for a broad spectrum of therapies causing a direct and immediate reduction of symptoms in man and animal. The impact is of special benefit to efficiently combat severe diseases, such as cancer, inflammation and/or fibrotic diseases, either alone or in combination with other anti-cancer, anti-inflammatory or anti-fibrotic treatments. In addition to the aforementioned clinical pictures, the compounds of formula (I), their salts, isomers, tautomers, enantiomeric forms, diastereomers, racemates, derivatives, prodrugs and/or metabolites are also useful for the diagnosis and treatment of any illnesses arising from TGF-β kinase signaling, particularly associated with cell proliferation and cell migration to be inhibited. The low molecular weight inhibitors are applied either themselves and/or in combination with physical measurements for diagnostics of effectiveness of any method of treatment, such as surgery, immune-, radio- and/or chemotherapy; the latter means a targeted therapy with any NME (i.e. NCE and/or NBE) as mono- and/or on-target/off-target combination therapy.

Due to their surprisingly strong and/or selective inhibition of enzymes, which regulate cellular processes by transferring phosphate groups from ATP to protein, the compounds of the invention can be advantageously administered at lower doses compared to other less potent or selective inhibitors of the prior art while still achieving equivalent or even superior desired biological effects. In addition, such a dose reduction may advantageously lead to less or even no medicinal adverse effects. Further, the high inhibition selectivity of the compounds of the invention may translate into a decrease of undesired side effects on its own regardless of the dose applied.

All the references cited herein are incorporated by reference in the disclosure of the invention hereby.

It is to be understood that this invention is not limited to the particular compounds, pharmaceutical compositions, uses and methods described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a compound" includes a single or several different compounds, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The example are particularly to be construed such that they are not limited to the explicitly demonstrated combinations of features, but the exemplified features may be unrestrictedly combined again if the technical problem of the invention is solved.

In the following examples, "conventional workup" means: water was added if necessary, the pH was adjusted, if necessary, to a value of between 2 and 10, depending on the constitution of the end product, the mixture was extracted with ethyl acetate or dichloro-methane, the phases were separated, the organic phase was dried over sodium sulfate and evaporated, and the product was purified by chromatography on silica gel and/or by crystallization. $R_f$-values were determined on silica gel. The eluent was ethyl acetate/methanol 9:1.

LC-MS Method A/LC-System 2

Mass spectrum: MH+; Agilent instrumentation series 1100; electrospray positive mode; scan 85-1000 m/z; fragmentation by voltage variable; gas temperature 300° C.; Solvents Lichrosolv quality Merck KGaA LC column: Chromolith Speed ROD RP-18e, 50×4.6 mm$^2$ Eluent A: 0.1% trifluoroacetic acid in water
Eluent B: 0.1% trifluoroacetic acid in acetonitrile
Gradient: 4% to 100% solvent B in 2.6 minutes
Flow: 2.4 ml/min
UV detection: 220 nm
LC-MS Method B/LC-System 1
Mass spectrum: MH+; Agilent instrumentation series 1100; electrospray positive mode; scan 85-1000 m/z; fragmentation by voltage variable; gas temperature 300° C.; Solvents Lichrosolv quality Merck KGaA
LC column: Chromolith Speed ROD RP-18e, 50×4.6 mm$^2$
Eluent A: 0.05% formic acid in water
Eluent B: 0.04% formic acid in acetonitrile
Gradient: 4% to 100% solvent B in 2.8 minutes plus 0.5 min post wash at 100% B
Flow: 2.4 ml/min
UV detection: 220 nm

EXAMPLE 1

Synthesis of 4-chloro-2-(5-chloro-2-fluoro-phenyl)-[1,8]naphthyridine

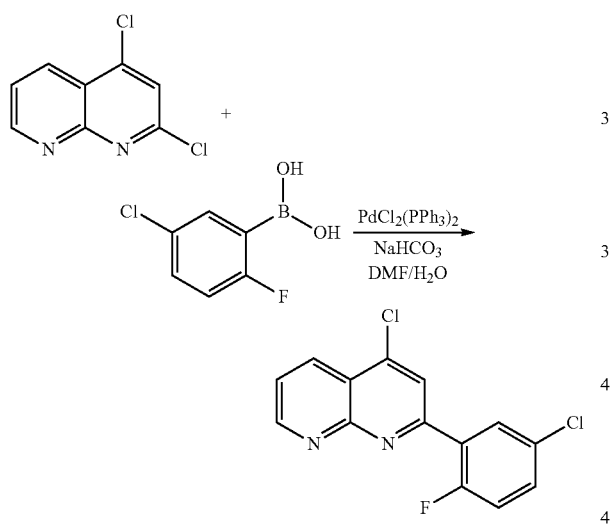

A solution of 9.95 g (50.0 mmol) 2,4-dichloro-[1,8]naphthyridine (described by Koller, Chemische Berichte 60: 407 (1927)), 8.72 g (50.0 mmol) 5-chloro-2-fluorophenylboronic acid und 5.04 g (60.0 mmol) sodium hydrogencarbonate in 100 ml DMF und 50 ml water was heated to 80° C. under nitrogen. 701 mg (1.0 mmol) bis-(triphenylphosphine)-palladium(II)-chloride were added and the mixture was stirred for 16 hrs at 80° C. Water was added to the reaction mixture and the precipitate was filtered off, dried in vacuum and re-crystallized from 2-propanole. This yielded 4-chloro-2-(5-chloro-2-fluoro-phenyl)-[1,8]naphthyridine as yellowish crystals; HPLC-MS: 2.49 min, [M+H] 293. $^1$H NMR (400 MHz, CDCl$_3$) δ [ppm]=9.14 (dd, J=4.2, 1.9, 1H), 8.56 (dd, J=8.3, 1.9, 1H), 8.37 (dd, J=6.8, 2.7, 1H), 8.10 (d, J=1.6, 1H), 7.56 (dd, J=8.4, 4.2, 1H), 7.36 (ddd, J=8.7, 4.2, 2.8, 1H), 7.10 (dd, J=10.9, 8.8, 1H).

The following compounds were similarly produced:
4-Chloro-2-(2-fluoro-phenyl)-[1,8]naphthyridine; HPLC-MS: 2.30 min, [M+H] 259;
4-Chloro-2-(4-fluoro-phenyl)-[1,8]naphthyridine; HPLC-MS: 2.29 min, [M+H] 259;
4-Chloro-2-(3-chloro-phenyl)-[1,8]naphthyridine; HPLC-MS: 2.44 min, [M+H] 275;
4-Chloro-2-(3-trifluoromethyl-phenyl)-[1,8]naphthyridine; HPLC-MS: 2.49 min, [M+H] 309;
4-Chloro-2-(2-fluoro-5-trifluoromethyl-phenyl)-[1,8]naphthyridine; HPLC-MS: 2.52 min, [M+H] 327;
4-Chloro-2-(2,4,5-trifluoro-phenyl)-[1,8]naphthyridine; HPLC-MS: 2.45 min, [M+H] 295;
4-Chloro-2-(2-fluoro-5-trifluoromethoxy-phenyl)-[1,8]naphthyridine; HPLC-MS: 2.63 min, [M+H] 343;
4-Chloro-2-(2,5-difluoro-phenyl)-[1,8]naphthyridine; HPLC-MS: 2.32 min, [M+H] 277.

EXAMPLE 2

Synthesis of 4-chloro-2-(6-methylpyridin-2-yl)-[1,8]naphthyridine

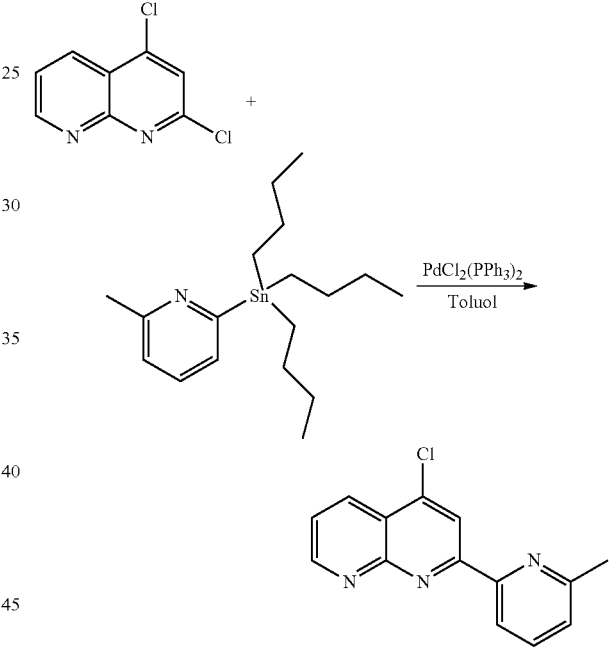

A solution of 1.69 g (8.47 mmol) 2,4-dichloro-[1,8]naphthyridine and 3.24 g (8.47 mmol) 6-methyl-2-(tributylstannyl)-pyridine in 8.5 ml toluene under nitrogen was heated to 80° C.

Then 178 mg (0.254 mmol) bis-(triphenylphosphine)-palladium(II)-chloride were added. The mixture was stirred for 16 hrs at 80° C. and then cooled to 0° C. in an ice bath. The precipitate is filtered off, washed with ice cold toluene and petrolether and dried in vacuum. This yielded 4-chloro-2-(6-methylpyridin-2-yl)-[1,8]naphthyridine as gray felted needles; HPLC-MS: 2.25 min, [M+H] 256.

$^1$H-NMR (CDC$_3$): δ [ppm]=2.71 (s, 3H), 7.29 (d, J=7.3 Hz, 1H), 7.61 (dd, J$_1$=8.3 Hz, J$_2$=4.1 Hz, 1H), 7.80 (t, J=7.7 Hz, 1H), 8.66 (dd, J$_1$=8.1 Hz, J$_2$=2.0 Hz, 1H), 8.67 (d, J=7.8 Hz, 1H), 8.9 (s, 1H), 9.2 (dd, J$_1$=4.1 Hz, J$_2$=1.9 Hz, 1H).

The following compounds were similarly produced:
4-Chloro-2-pyrazin-2-yl-[1,8]naphthyridine; HPLC-MS: 1.99 min, [M+H] 243;

4-Chloro-2-pyridin-2-yl-[1,8]naphthyridine; HPLC-MS: 2.06 min, [M+H] 242.

EXAMPLE 3

Synthesis of 2-(6-methylpyridin-2-yl)-[1,8]naphthyridin-4-yl]-pyridin-4-yl-amine (no. 03)

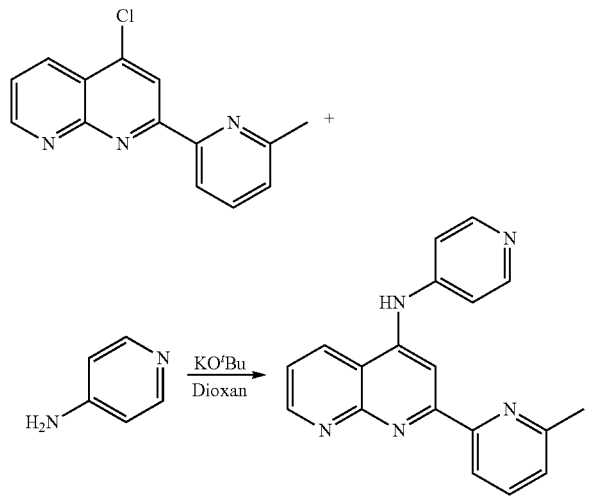

To a solution of 189 mg (0.739 mmol) 4-chloro-2-(6-methylpyridin-2-yl)-[1,8]naphthyridine and 76.5 mg (0.813 mmol) 4-aminopyridine in 2 ml dioxane kept at 80° C., 174 mg (1.55 mmol) potassium tert.-butylate were added and stirred at this temperature for 30 additional minutes. The reaction mixture was cooled down to ambient temperature and water was added. The precipitate was filtered off, washed with water and purified by prep. HPLC in water/acetonitrile. This yielded [2-(6-methylpyridin-2-yl)-[1,8]naphthyridin-4-yl]-pyridin-4-yl-amine as yellowish crystals; HPLC-MS: [M+H] 314.

$^1$H-NMR (d$^6$-DMSO): δ [ppm]=2.57 (s, 3H), 7.35 (d, J=5.6 Hz, 2H), 7.41 (d, J=7.4 Hz, 1H), 7.65 (dd, J$_1$=8.2 Hz, J$_2$=4.1 Hz, 1H), 7.93 (t, J=7.7 Hz, 1H), 8.43 (d, J=7.9 Hz, 1H), 8.46 (m, 2H), 8.59 (s, 1H), 8.74 (d, J=8.2 Hz, 1H), 9.12 (m, 1H), 9.96 (bs, 1H).

This material dissolved in 2-propanol was added dropwise to an excess of 0.1 N HCl in 2-propanol to obtain the dihydrochlorid: yellow crystals; HPLC-MS [M+H] 314.

The following compounds were similarly produced:

(2-Pyrazin-2-yl-[1,8]naphthyridin-4-yl)-pyridin-4-yl-amine (no. 24)

$^1$H NMR (500 MHz, d$^6$-DMSO): δ [ppm]=9.76 (d, J=1.0, 1H), 9.73 (s, 1H), 9.15 (dd, J=4.1, 1.8, 1H), 8.85 (dd, J=8.4, 1.8, 1H), 8.82-8.78 (m, 2H), 8.51 (m, 2H), 8.44 (s, 1H), 7.70 (dd, J=8.4, 4.2, 1H), 7.40-7.36 (m, 2H).

Pyridin-4-yl-(2-pyridin-2-yl-[1,8]naphthyridin-4-yl)-amine (no. 25)

$^1$H NMR (400 MHz, d$^6$-DMSO): δ [ppm]=9.66 (s, 1H), 9.11 (dd, J=4.2, 1.8, 1H), 8.80 (dd, J=8.4, 1.9, 1H), 8.74-8.72 (m, 1H), 8.63 (d, J=7.9, 1H), 8.56 (s, 1H), 8.50-8.48 (m, 2H), 8.04 (td, J=7.7, 1.8, 1H), 7.65 (dd, J=8.4, 4.2, 1H), 7.53 (ddd, J=7.5, 4.8, 1.2, 1H), 7.35 (m, 2H).

EXAMPLE 4

Synthesis of [2-(2-fluorophenyl)-[1,8]naphthyridin-4-yl]-pyridin-4-yl-amine (no. 10)

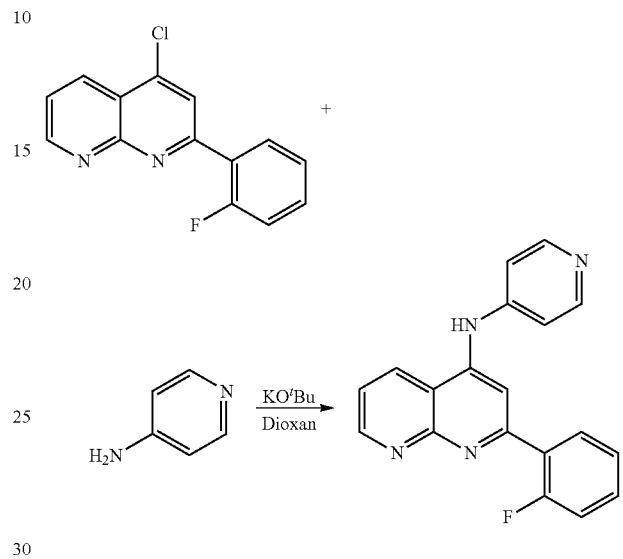

To a suspension of 259 mg (1.00 mmol) 4-chloro-2-(2-fluorophenyl)-[1,8]naphthyridine and 104 mg (1.10 mmol) 4-aminopyridine in 5 ml dioxane 236 mg (2.10 mmol) potassium tert.-butylate were added, the mixture heated to 80° C. and kept at this temperature for 1 hr. After cooling to ambient temperature water was added to the reaction mixture. The precipitate formed was filtered off, washed with water and dried in vacuum. This yielded [2-(2-fluoro-phenyl)-[1,8]naphthyridin-4-yl]-pyridin-4-yl-amine as beige crystals; HPLC-MS: [M+H] 317. $^1$H-NMR (d$^6$-DMSO): δ [ppm]= 7.34 (d, J=5.9 Hz, 2H), 7.38 (dd, J$_1$=11.8 Hz, J$_2$=8.2 Hz, 1H), 7.41 (t, J=7.4 Hz, 1H), 7.57 (m, 1H), 7.66 (dd, J$_1$=8.3 Hz, J$_2$=4.1 Hz, 1H), 7.83 (s, 1H), 8.12 (t, J=7.8 Hz, 1H), 8.46 (d, J=5.9 Hz, 2H), 8.81 (dd, J$_1$=8.4 Hz, J$_2$=1.8 Hz, 1H), 9.1 (dd, J$_1$=4.3 Hz, J$_2$=1.8 Hz, 1H), 9.67 (bs, 1H).

The following compounds were similarly produced:

[2-(5-Chloro-2-fluoro-phenyl)-[1,8]naphthyridin-4-yl]-pyrimidin-4-yl-amine (no. 05)

$^1$H NMR (500 MHz, DMSO) δ=10.19 (s, 1H), 9.14 (dd, J=4.0, 1.5, 1H), 8.97 (s, 1H), 8.94 (dd, J=8.5, 1.5, 1H), 8.83 (s, 1H), 8.55 (d, J=5.8, 1H), 8.14 (dd, J=6.6, 2.7, 1H), 7.72 (dd, J=8.4, 4.1, 1H), 7.69-7.64 (m, 1H), 7.51 (dd, J=10.7, 9.0, 1H), 7.34 (d, J=5.8, 1H).

[2-(4-Fluoro-phenyl)-[1,8]naphthyridin-4-yl]-pyridin-4-yl-amine (no. 6)

[2-(3-Chloro-phenyl)-[1,8]naphthyridin-4-yl]-pyridin-4-yl-amine (no. 11)

Pyridin-4-yl-[2-(3-trifluoromethyl-phenyl)-[1,8]naphthyridin-4-yl]-amine (no. 12)

[2-(2,5-Difluoro-phenyl)-[1,8]naphthyridin-4-yl]-pyridin-4-yl-amine (no. 13)

$^1$H NMR (400 MHz, DMSO) δ=9.71 (s, 1H), 9.11 (dd, J=4.1, 1.7, 1H), 8.82 (dd, J=8.4, 1.7, 1H), 8.46 (d, J=6.2, 2H), 7.90 (ddd, J=9.2, 5.9, 3.0, 1H), 7.85 (s, 1H), 7.67 (dd, J=8.4, 4.2, 1H), 7.52-7.38 (m, 2H), 7.35 (d, J=6.2, 2H).

[2-(2-Fluoro-5-trifluoromethyl-phenyl)-[1,8]naph-thyridin-4-yl]-pyridin-4-yl-amine (no. 16)

¹H NMR (500 MHz, DMSO) δ=9.83 (s, 1H), 9.13 (dd, J=4.1, 1.8, 1H), 8.82 (dd, J=8.4, 1.8, 1H), 8.47 (m, 3H), 7.96 (m, 1H), 7.91 (s, 1H), 7.69 (dd, J=8.4, 4.2, 1H), 7.65 (m, 1H), 7.37 (dd, J=4.9, 1.4, 2H).

[2-(2-Fluoro-phenyl)-[1,8]naphthyridin-4-yl]-pyrimidin-4-yl-amine (no. 17)

[2-(5-Chloro-2-fluoro-phenyl)-[1,8]naphthyridin-4-yl]-pyridazin-4-yl-amine

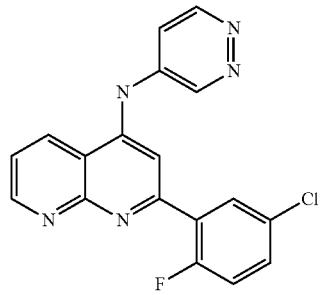 [SMILES: Fc1ccc(Cl)cc1-c1cc(Nc2ccnnc2)c2cccnc2n1]

[2-(2-Fluoro-5-trifluoromethoxy-phenyl)-[1,8]naph-thyridin-4-yl]-pyridin-4-yl-amine (no. 38)

¹H NMR (400 MHz, DMSO) δ=9.73 (s, 1H), 9.11 (dd, J=4.1, 1.8, 1H), 8.83 (dd, J=8.4, 1.8, 1H), 8.46 (d, J=6.3, 2H), 8.10 (dd, J=5.9, 2.7, 1H), 7.87 (s, 1H), 7.62 (m, 3H), 7.36 (d, J=6.3, 2H).

Pyridin-4-yl-[2-(2,4,5-trifluoro-phenyl)-[1,8]naph-thyridin-4-yl]-amine (no. 43)

¹H NMR (500 MHz, DMSO) δ=9.71 (bs, 1H), 9.11 (dd, J=4.1, 1.6, 1H), 8.81 (dd, J=8.4, 1.7, 1H), 8.46 (d, J=6.2, 2H), 8.15 (m, 2H), 7.82 (s, 1H), 7.74 (td, J=10.8, 6.7, 1H), 7.67 (dd, J=8.4, 4.2, 1H), 7.35 (d, J=6.2, 2H).

EXAMPLE 5

Synthesis of 2-(5-chloro-2-fluorophenyl)-[1,8]naph-thyridin-4-yl]-[3-(3-morpholin-4-yl-propoxy)-pyridin-4-yl]-amine (no. 34)

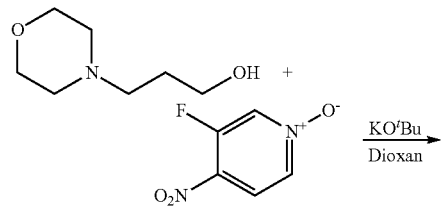

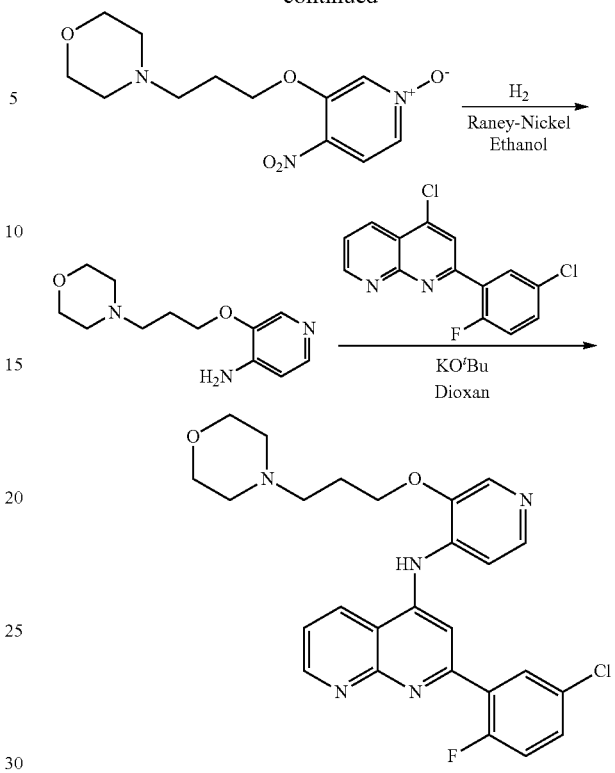

To a slurry of 790 mg (5.00 mmol) 3-fluoro-4-nitropyridine-1-oxide and 762 mg 4-(3-hydroxypropyl)-morpholine in 10 ml dioxane, 673 mg (6.00 mmol) potassium tert.-butylate were added and stirred at ambient temperature for 16 hrs. The reaction mixture was diluted with ethylacetate, filtered and the filtrate evaporated. The residue was chromatographed on a silica column with dichloromethane/methanol. This yielded 4-[3-(4-nitro-1-oxypyridin-3-yloxy)-propyl]-morpholine as a brownish oil; HPLC-MS: [M+H] 284.

A solution of 460 mg (1.63 mmol) 4-[3-(4-nitro-1-oxypyridin-3-yloxy)-propyl]-morpholine in ml ethanol was hydrogenated on Raney-Nickel catalyst at ambient temperature and normal pressure. The catalyst was filtered off, the filtrate was evaporated to dryness. This yielded 3-(3-morpholin-4-yl-propoxy)-pyridin-4-ylamine as orange oil; HPLC-MS: [M+H] 238.

A slurry of 147 mg (0.50 mmol) 4-chloro-2-(5-chloro-2-fluorophenyl)-[1,8]naphthyridine and 131 mg (0.55 mmol) 3-(3-morpholin-4-yl-propoxy)-pyridin-4-ylamine in 2.5 ml dioxane was heated to 80° C. under nitrogen. After addition of 118 mg (1.05 mmol) potassium tert.-butylate the reaction mixture was stirred at 80° C. for 1 hr. After cooling to ambient temperature water was added to the mixture. The reaction mixture was filtered and the filtrate evaporated. The residue was chromatographed on a silica column with dichloromethane/methanol. This yielded 2-(5-chloro-2-fluorophenyl)-[1,8]naphthyridin-4-yl]-[3-(3-morpholin-4-yl-propoxy)-pyridin-4-yl]-amine; HPLC-MS: 1.20 min, [M+H] 494.

¹H NMR (500 MHz, d⁶-DMSO): δ [ppm]=9.21 (s, 1H), 9.07 (m, 1H), 8.79 (dd, J=8.4, 1.5, 1H), 8.41 (s, 1H), 8.19 (d, J=5.0, 1H), 8.13 (dd, J=6.6, 2.7, 1H), 7.62 (dd, J=8.3, 4.2, 1H), 7.59 (m, 1H), 7.39 (dd, J=10.9, 8.9, 1H), 7.31 (d, J=5.1, 1H), 7.10 (s, 1H), 4.11 (t, J=6.1, 2H), 3.39 (m, 5H), 2.00 (m, 6H), 1.64 (m, 2H).

The following compound was similarly produced:

[2-(5-Chloro-2-fluoro-phenyl)-[1,8]naphthyridin-4-yl]-[3-(2-morpholin-4-yl-ethoxy)-pyridin-4-yl]-amine (no. 4)

$^1$H NMR (400 MHz, d$^6$-DMSO): δ [ppm]=9.22 (bs, 1H), 9.09 (d, J=2.4, 1H), 8.79 (dd, J=8.4, 1.6, 1H), 8.45 (s, 1H), 8.21 (d, J=5.1, 1H), 8.17-8.03 (m, 1H), 7.63 (m, 2H), 7.42 (dd, J=10.9, 8.9, 1H), 7.33 (d, J=5.0, 1H), 7.15 (s, 1H), 4.23 (t, J=5.5, 2H), 3.3 (m, 4H), 3.28 (t, J=5.5, 2H), 2.17 (m, 4H).

EXAMPLE 6

Synthesis of [2-(2-fluoro-5-trifluoromethyl-phenyl)-[1,8]naphthyridin-4-yl]-pyrimidin-4-yl-amine (no. 21)

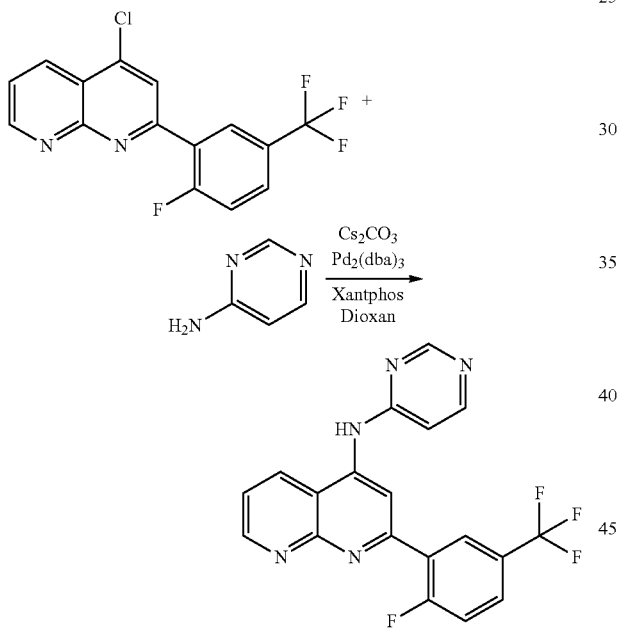

To a solution of 307 mg (0.94 mmol) 4-chloro-2-(2-fluoro-5-trifluoromethyl-phenyl)-[1,8]naphthyridine in 10 ml dioxane under nitrogen, 89 mg (0.94 mmol) 4-aminopyrimidine, 612 mg (1.88 mmol) cesium carbonate, 54 mg (0.093 mmol) 9,9-dimethyl-4,5-bis(diphenylphosphino)xanthene and 34 mg (0.038 mmol) tris(dibenzylideneaceton)-dipalladium(0) were added and heated in a microwave apparatus to 140° C. for 30 minutes. The reaction mixture was partitioned between dichloromethane and water. The organic phase was dried and the product chromatographed on a silica gel column with dichloro-methane/methanol. This yielded [2-(2-fluoro-5-trifluoromethyl-phenyl)-[1,8]naphthyridin-4-yl]-pyrimidin-4-yl-amine as beige crystals; HPLC-MS: 1.72 min, [M+H] 386.

$^1$H NMR (500 MHz d$^6$-DMSO): δ [ppm]=10.19 (s, 1H), 9.13 (dd, J=4.1, 1.7, 1H), 9.03 (d, J=1.3, 1H), 8.94 (dd, J=8.5, 1.7, 1H), 8.82 (s, 1H), 8.54 (d, J=5.8, 1H), 8.48 (dd, J=6.9, 2.2, 1H), 7.98 (m, 1H), 7.73-7.66 (m, 2H), 7.34 (dd, J=5.8, 1.0, 1H).

The following compounds were similarly produced:

[2-(5-Chloro-2-fluoro-phenyl)-[1,8]naphthyridin-4-yl]-[1,3,5]triazin-2-yl-amine (no. 18)

$^1$H NMR (500 MHz, d$^6$-DMSO): δ [ppm]=11.02 (s, 1H), 9.12 (dd, J=3.9, 1.6, 1H), 8.86 (s, 2H), 8.83 (dd, J=8.4, 1.5, 1H), 8.58 (s, 1H), 8.12 (dd, J=6.6, 2.7, 1H), 7.65 (m, 2H), 7.49 (dd, J=10.5, 9.0, 1H).

[2-(2-Fluoro-5-trifluoromethyl-phenyl)-[1,8]naphthyridin-4-yl]-[1,3,5]triazin-2-yl-amine (no. 44)

$^1$H NMR (400 MHz, d$^6$-DMSO): δ [ppm]=11.04 (s, 1H), 9.15 (dd, J=4.2, 1.8, 1H), 8.92 (s, 2H), 8.85 (dd, J=8.5, 1.9, 1H), 8.68 (d, J=1.7, 1H), 8.48 (dd, J=6.9, 2.3, 1H), 8.01 (ddd, J=7.0, 3.8, 2.7, 1H), 7.70 (m, 2H).

[2-(6-Methyl-pyridin-2-yl)-[1,8]naphthyridin-4-yl]-pyrimidin-4-yl-amine (no. 49); HPLC-MS: 1.18 min, [M+H] 315;

Pyrimidin-4-yl-[2-(2,4,5-trifluoro-phenyl)-[1,8]naphthyridin-4-yl]-amine (no. 50); HPLC-MS: 1.56 min, [M+H] 354

EXAMPLE 7

Synthesis of obtained [2-(1-methyl-1H-pyrazol-3-yl)-[1,8]naphthyridin-4-yl]-pyridin-4-yl-amine (no. 35) and [2-(2-Methyl-2H-pyrazol-3-yl)-[1,8]naphthyridin-4-yl]-pyridin-4-yl-amine (no. 36)

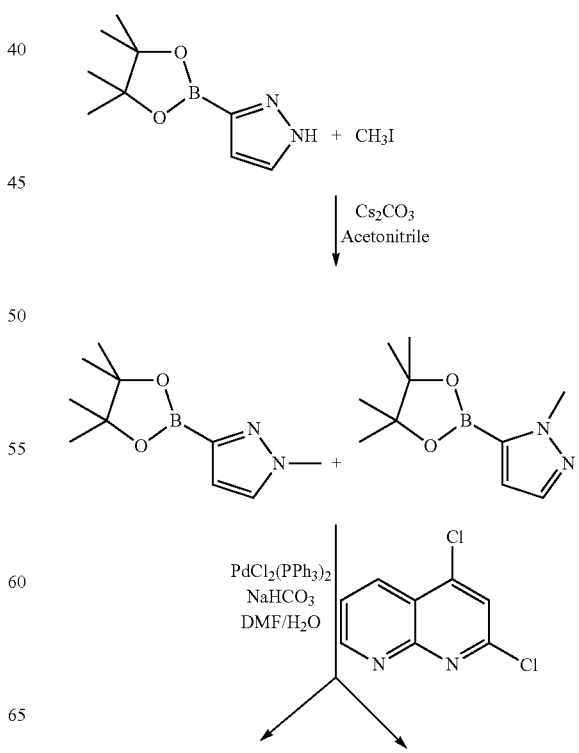

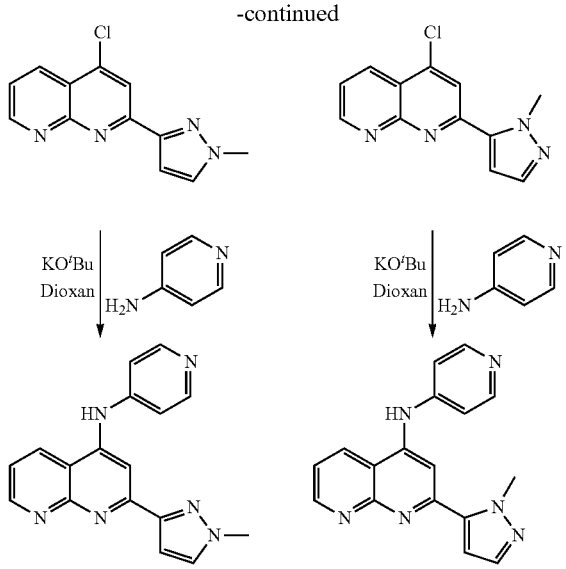

To a solution of 10.6 g (54.7 mmol) 3-(4,4,5,5-tetramethyl-[1,3,2]dioxaborolan-2-yl)-1H-pyrazole in 100 ml acetonitrile, 17.8 g (54.7 mmol) caesium carbonate were added and the mixture stirred at ambient temperature for 70 hrs. The reaction mixture was filtered and the residue washed with acetonitrile. The combined filtrates were evaporated and taken into tert.butylmethylether. Undissolved material was filtered off; the filtrate was dried over sodium sulfate and evaporated. One got a mixture of 1-methyl-3-(4,4,5,5-tetramethyl-[1,3,2]dioxaborolan-2-yl)-1H-pyrazole und 1-methyl-5-(4,4,5,5-tetramethyl-[1,3,2]dioxaborolan-2-yl)-1H-pyrazole as colorless, slowly crystallizing oil.

A solution of 2.99 g (15.0 mmol) 2,4-dichloro-[1,8]naphthyridine, 3.12 g (15.0 mmol) of the product mixture from step 1 and 1.51 g (18.0 mmol) sodium hydrogen carbonate in ml DMF and 15 ml water were heated to 80° C. under nitrogen. Then 526 mg (0.75 mmol) bis-(triphenylphosphine)-palladium(II)-chloride were added and the mixture stirred at 80° C. for 16 hrs. The reaction mixture was distributed between dichloromethane and water. The organic phase was dried over sodium sulfate and the product chromatographed on a silica column in dichloromethane/methanol. One obtained the two isomers:

4-chloro-2-(1-methyl-1H-pyrazol-3-yl)-[1,8]naphthyridine as pale yellow powder (HPLC-MS: [M+H] 245)

$^1$H NMR (400 MHz, d$^6$-DMSO): δ [ppm]=9.15 (dd, J=4.2, 1.9, 1H), 8.62 (dd, J=8.3, 1.9, 1H), 8.28 (s, 1H), 7.91 (d, J=2.2, 1H), 7.73 (dd, J=8.3, 4.2, 1H), 7.05 (d, J=2.3, 1H), 4.00 (s, 3H)

4-chloro-2-(2-methyl-2H-pyrazol-3-yl)-[1,8]naphthyridine as pale yellow powder (HPLC-MS: [M+H] 245).

$^1$H NMR (400 MHz, d$^6$-DMSO): δ [ppm]=9.19 (dd, J=4.2, 1.8, 1H), 8.65 (dd, J=8.3, 1.8, 1H), 8.37 (s, 1H), 7.79 (dd, J=8.3, 4.2, 1H), 7.61 (d, J=2.0, 1H), 7.27 (d, J=2.0, 1H), 4.38 (s, 3H).

A slurry of 122 mg (0.50 mmol) 4-chloro-2-(1-methyl-1H-pyrazol-3-yl)-[1,8]naphthyridine and 52 mg (0.55 mmol) 4-aminopyridine in 2.5 ml dioxane was heated under nitrogen to 80° C. Then 118 mg (1.05 mmol) potassium tert.-butylate were added and the mixture stirred at 80° C. for 18 hrs. The reaction mixture was partitioned between dichloromethane and water. The organic phase was dried over sodium sulfate, evaporated and the product crystallized from tert.butylmethylether. One obtained [2-(1-methyl-1H-pyrazol-3-yl)-[1,8]naphthyridin-4-yl]-pyridin-4-yl-amine as colorless crystals; HPLC-MS: [M+H] 303.

$^1$H NMR (500 MHz, d$^6$-DMSO): δ [ppm]=9.51 (s, 1H), 9.03 (dd, J=4.1, 1.7, 1H), 8.71 (dd, J=8.3, 1.7, 1H), 8.46 (d, J=6.1, 2H), 8.03 (s, 1H), 7.83 (d, J=2.2, 1H), 7.57 (dd, J=8.3, 4.2, 1H), 7.29 (d, J=6.2, 2H), 6.99 (d, J=2.2, 1H), 3.94 (s, 3H).

The following compound was similarly produced:
[2-(2-Methyl-2H-pyrazol-3-yl)-[1,8]naphthyridin-4-yl]-pyridin-4-yl-amine as colorless crystals; HPLC-MS: [M+H] 303.

$^1$H NMR (500 MHz, d$^6$-DMSO): δ [ppm]=9.62 (s, 1H), 9.07 (dd, J=4.1, 1.7, 1H), 8.78 (dd, J=8.4, 1.8, 1H), 8.43 (d, J=6.2, 2H), 7.73 (s, 1H), 7.63 (dd, J=8.3, 4.2, 1H), 7.52 (d, J=1.9, 1H), 7.33 (d, J=6.3, 2H), 7.33 (d, J=6.3, 2H), 6.93 (d, J=2.0, 1H), 4.32 (s, 3H).

EXAMPLE 8a

Synthesis of {4-[2-(5-chloro-2-fluoro-phenyl)-[1,8]naphthyridin-4-ylamino]-pyrimidin-2-yl}-carbamic acid tert-butyl ester (no. 51)

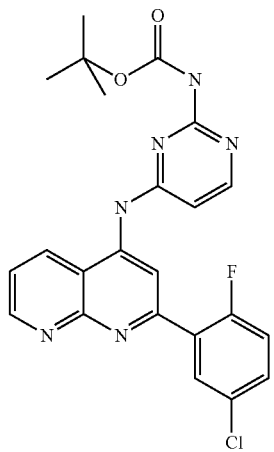 [SMILES: CC(C)(C)OC(=O)Nc1nccc(Nc2cc(-c3cc(Cl)ccc3F)nc3ncccc23)n1]

1 g of commercial 2,4-diamino pyrimidine was treated in 40 ml tert.-butanol with 1.5 g BOC2O in the presence of 3.48 ml DIPEA at ambient temperature for 6 hrs. After evaporation, the product was extracted with ethyl acetate from water, dried with Na$_2$SO$_4$, filtered and evaporated to dryness. After digestion with petrolether:ether 3:1 (vol) and drying 849 mg (4-amino-pyrimidin-2-yl)-carbamic acid tert-butyl ester was obtained as a white powder with R$_t$~1.08 min and correct mass of M+H~211

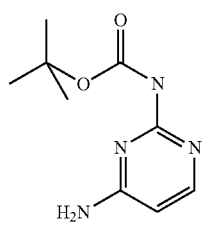

200 mg 4-chloro-2-(5-chloro-2-fluoro-phenyl)-[1,8]naphthyridine (cf. EXAMPLE 1) and 143 mg (4-amino-pyrimidin-2-yl)-carbamic acid tert-butyl ester in 8 ml dioxane containing 444 mg Cs$_2$CO$_3$, 13 mg Pd$_2$(dba)$_3$ and 16 mg xantphos were incubated under argon gas at 80° C. for 16 hrs. After evaporation to dryness the crude sample was flashed on SiO$_2$ with a MeOH gradient in DCM. A pooled fraction was dried down and digested with ether to give 88 mg product {4-[2-(5-chloro-2-fluoro-phenyl)-[1,8]naphthyridin-4-ylamino]-pyrimidin-2-yl}-carbamic acid tert-butyl ester as a white powder with Rt~1.80 min and correct mass found M+H~467.

EXAMPLE 8b

Synthesis of N4-[2-(5-chloro-2-fluoro-phenyl)-[1,8] naphthyridin-4-yl]-pyrimidine-2,4-diamine (no. 52)

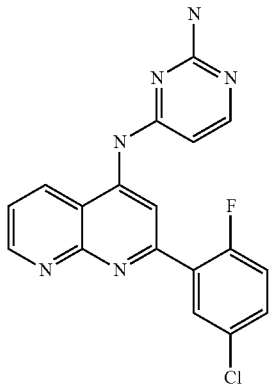 [SMILES: Nc1nccc(Nc2cc(-c3cc(Cl)ccc3F)nc3ncccc23)n1]

88 mg of {4-[2-(5-chloro-2-fluoro-phenyl)-[1,8]naphthyridin-4-ylamino]-pyrimidin-2-yl}-carbamic acid tert-butyl ester (cf. EXAMPLE 8a) were treated with 6 ml 4 m HCl in dioxane at ambient temperature for 4 hrs. After evaporation the product was digerated with ether and isolated by filtration to give 57 mg of N4-[2-(5-chloro-2-fluoro-phenyl)-[1,8] naphthyridin-4-yl]-pyrimidine-2,4-diamine as hydrochloride salt with R$_t$~1.36 min and correct mass found M+H~367.

EXAMPLE 9

Synthesis of N-[2-(6-methyl-pyridin-2-yl)-[1,8] naphthyridin-4-yl]-pyrimidine-4,6-diamine (no. 55)

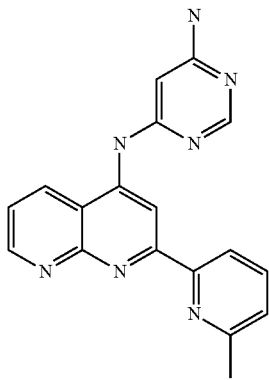 [SMILES: Cc1cccc(-c2cc(Nc3cc(N)ncn3)c3cccnc3n2)n1]

Similar as in EXAMPLE 8, the target compound was synthesized from 174 mg 4-chloro-2-(6-methyl-pyridin-2-yl)-[1, 8]naphthyridine and 143 mg (6-amino-pyrimidin-4-yl)-carbamic acid tert.-butyl ester to yield a crude product that was treated with aqueous TFA to de-protect BOC and obtain—after reversed phase chromatography on a Gemini RP18 column in 0.3% TFA with an acetonitrile gradient—the isolated product N-[2-(6-methyl-pyridin-2-yl)-[1,8]naphthyridin-4-yl]-pyrimidine-4,6-diamine with R$_t$~1.18 min and correct mass found M+H~330.

The same compound can be obtained without protection strategy by use of 4,6-diamino pyrimidine instead of (6-amino-pyrimidin-4-yl)-carbamic acid tert.-butyl ester.

EXAMPLE 10

Synthesis of 4-[2-(5-chloro-2-fluoro-phenyl)-[1,8] naphthyridin-4-ylamino]-N-methyl-nicotinamide 200 mg 4-chloro-2-(5-chloro-2-fluoro-phenyl)-[1,8]naphthyridine and 104 mg methyl 4-aminonicotinate in 8 ml dioxane containing 444 mg Cs$_2$CO$_3$, 13 mg Pd$_2$ (dba)$_3$ and 16 mg xantphos were incubated under argon gas at 90° C. for 18 hrs. After evaporation to dryness the crude sample was flashed on SiO$_2$ with a MeOH gradient in DCM. A pooled fraction was evaporated to give 28 mg product 4-[2-(5-chloro-2-fluoro-phenyl)-[1,8]naphthyridin-4-ylamino]-nicotinic acid methyl ester with R$_t$~1.60 min and correct mass found M+H~409.

14.4 mg 4-[2-(5-chloro-2-fluoro-phenyl)-[1,8]naphthyridin-4-ylamino]-nicotinic acid methyl ester were treated with 250 μl of 33% methylamine in ethanol at 40° C. for 5 min and then at ambient temperature for 16 hrs. After evaporation the product was digerated with ether and dried to give 15.7 mg 4-[2-(5-chloro-2-fluoro-phenyl)-[1,8]naphthyridin-4-ylamino]-N-methyl-nicotinamide as a yellowish powder with R$_t$~1.47 min and correct mass M+H~408.

EXAMPLE 11

Synthesis of {4-[2-(2-fluoro-5-trifluoromethyl-phenyl)-[1,8]naphthyridin-4-ylamino]-pyridin-3-yl}-methanol 150 mg 4-chloro-2-(2-fluoro-5-trifluoromethyl-phenyl)-[1,8]naphthyridine and 57 mg 4-amino-3-hydroxymethylpyridine in 6 ml dioxane containing 299 mg Cs$_2$CO$_3$, 8 mg Pd$_2$ (dba)$_3$ and 10 mg xantphos were incubated under argon gas at 90° C. for 18 hrs. After evaporation to dryness the crude sample was flashed on SiO$_2$ with a MeOH gradient in DCM. A pooled fraction was evaporated to give 59 mg product {4-[2-(2-fluoro-5-trifluoromethyl-phenyl)-[1,8]naphthyridin-4-ylamino]-pyridin-3-yl}-methanol with R$_t$~1.48 min and correct mass found M+H~415.

EXAMPLE 12

Synthesis of 1-[2-(2-fluoro-5-chloro-phenyl)-[1,8] naphthyridin-4-yl]-1,3-dihydro-imidazo[4,5-c]pyridin-2-one and/or [2-(2-fluoro-phenyl)-[1,8]naphthyridin-4-yl]-pyridin-4-yl-amine (no. 10)

Referring to the previous examples, said compounds were analogously obtained in accordance with the following scheme:

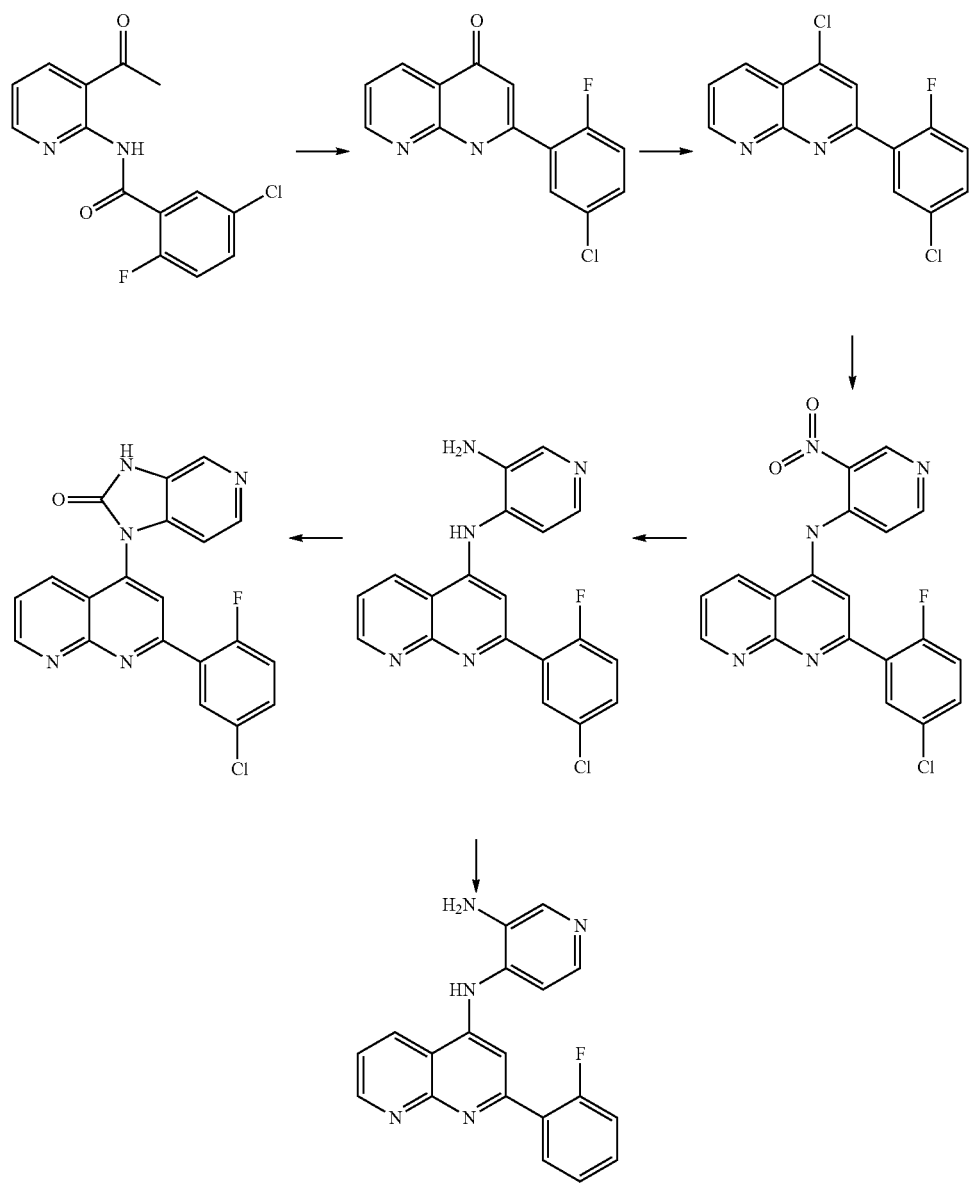

Further compounds, which can be analogously obtained according to any Example 1 to 12, are given in Table 1 above.

EXAMPLE 13

Cellular Assay for Testing TGF-Beta Receptor I Kinase Inhibitors

As an example, the ability of the inhibitors to eliminate TGF-beta-mediated growth inhibition was tested. Cells of the lung epithelial cell line Mv1Lu were sown in a defined cell density in a 96-well microtiter plate and cultivated overnight under standard conditions. Next day, the medium was replaced by medium which comprises 0.5% of FCS and 1 ng/ml of TGF-beta, and the test substances were added in defined concentrations, generally in the form of dilution series with 5 fold steps. The concentration of the solvent DMSO was constant at 0.5%. After a further two days, Crystal Violet staining of the cells was carried out. After extraction of the Crystal Violet from the fixed cells, the absorption was measured spectrophotometrically at 550 nm. It could be used as a quantitative measure of the adherent cells present and thus of the cell proliferation during the culture.

EXAMPLE 14

In-Vitro (Enzyme) Assay for Determination of the Efficacy of Inhibitors of the Inhibition of TGF-Beta-Mediated Effects The kinase assay was carried out as 384-well flashplate assay. 31.2 nM of GST-ALK5, 439 nM of GST-SMAD2 and 3 mM of ATP (with 0.3 µCi of $^{33}$P-ATP/well) were incubated in a total volume of 35 µl (20 mM of HEPES, 10 mM of MgCl$_2$, 5 mM of MnCl$_2$, 1 mM of DTT, 0.1% of BSA, pH 7.4) without or with test substance (5-10 concentrations) at 30° C.

for 45 min. The reaction was stopped using 25 μl of 200 mM EDTA solution, filtered with suction at room temperature after 30 min, and the wells were washed with 3 times 100 μl of 0.9% NaCl solution. Radioactivity was measured in the TopCount. The $IC_{50}$ values were calculated using RS1. The results are given in Table 1. Above and below, all temperatures were indicated in ° C.

EXAMPLE 15

Pharmaceutical Preparations (A) Injection Vials:
A solution of 100 g of an active ingredient according to the invention and 5 g of disodium hydrogen phosphate in 3 l of bidistilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

(B) Suppositories:
A mixture of 20 g of an active ingredient according to the invention was melted with 100 g of soy lecithin and 1400 g of cocoa butter, poured into moulds and allowed to cool. Each suppository contained 20 mg of active ingredient.

(C) Solution:
A solution was prepared from 1 g of an active ingredient according to the invention, 9.38 g of $NaH_2PO_4 \cdot 2 H_2O$, 28.48 g of $Na_2HPO_4 \cdot 12 H_2O$ and 0.1 g of benzalkonium chloride in 940 ml of bidistilled water. The pH was adjusted to 6.8, and the solution was made up to 1 l and sterilized by irradiation. This solution could be used in the form of eye drops.

(D) Ointment:
500 mg of an active ingredient according to the invention were mixed with 99.5 g of Vaseline under aseptic conditions.

(E) Tablets:
A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained mg of active ingredient.

(F) Coated Tablets:
Tablets were pressed analogously to Example E and subsequently coated in a conventional manner with a coating of sucrose, potato starch, talc, tragacanth and dye.

(G) Capsules:
2 kg of an active ingredient according to the invention were introduced into hard gelatin capsules in a conventional manner in such a way that each capsule contained mg of the active ingredient.

(H) Ampoules:
A solution of 1 kg of an active ingredient according to the invention in 60 l of bidistilled water was sterile filtered, transferred into ampoules, lyophilized under sterile conditions and sealed under sterile conditions. Each ampoule contained 10 mg of active ingredient.

(I) Inhalation Spray:
14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

The invention claimed is:
1. A compound of formula (I)

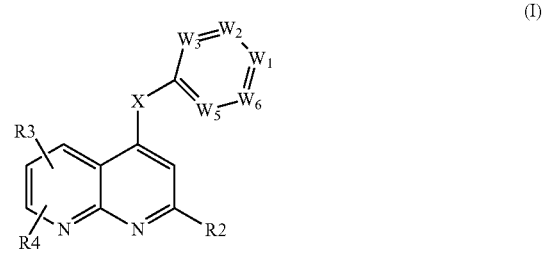

wherein
$W_1$, $W_5$, $W_6$ each denote, independently from one another, N or CH;
$W_2$ denotes N or CR6;
$W_3$ denotes N or CR5;
under the proviso that at least one of $W_1$, $W_2$, $W_3$, $W_5$ or $W_6$ denotes N;
X denotes NR1, Alk, O, or S;
R1 denotes H, A or Cyc;
R5 denotes H, A, Hal, OY, CN, -Alk-OY, COOY, —CO—NYY, SA, $SO_2A$, NYY, —OAlk-OY, —OAlk-NYY, —OAlk-NY—COOY, —OAlk-Het³, $NO_2$, —NH-Alk-COOY, —NH—CO-Alk-OY, —NH—CO-Alk-OCOY, —NH—CO-Alk-NYY, —NH—CO—NYY, —NH—CO-Het³, —NY—COOY, —NY—$SO_2Y$, —NH—$SO_2$—NYY, —NH-Het², —NH—R2, —NY—CO—R2, —NY—CO—NY—R2, —NY—COO—R2, —NY—$SO_2$—R2, —NY—$SO_2$—NY—R2, —OAr, —NY—Ar, —OHet¹, NY-Het¹, —CO—NYY—NYY, —CO-Het³ or —CO—NH-Alk-Het³;
or
R1, R5 together denote —CH=CH—, —C(Y)=N—, —N=C(Y)—, —C(COY)=N—, —C(CO—R2)=N—, —CO—NH—, —NH—CO—, —$SO_2$—NH—, —NH—$SO_2$—, =CH—NH—CO—, —CH—N(Alk-Het³)—CO—, —CH=C($NO_2$)— or —CH=C(Hal)-;
R6 denotes H, A, Hal, OY, CN, -Alk-OY, COOY, —CO—NYY, NYY, —NY—COOY, —NH-Alk-NYY, —NH—COA, —NH—CO-Alk-NYY, —NH-Het², Het³, —OAr, —NY—Ar, —OHet¹, NY-Het¹, Het¹, —NH—$SO_2Y$, —NH-Cyc, —NH-Het³, —NH-Alk-Het³, —NH-Alk-OY, —NH—CO—NYY, —NH—CO-Het³, —CO—NH-Het³, —NH—CO-Alk-OY, —NH—CO-Alk-Het³, —CO—NH-Alk-Het³, NH—CO-Alk-NH—COOY or —CO—NH-Alk-NYY;
R2 denotes a monocyclic carboaryl having 5-8 C atoms or a monocyclic heteroaryl having 2-7 C atoms and 1-4 N, O and/or S atoms, each of which is unsubstituted or substituted by at least one substituent selected from A, Hal, CN, NYY, OY, and =O;
R3, R4 each denote, independently from one another, H, A, Hal, CN, NYY, OY, —OAlk-NYY, or —OAlk-OY;
Y denotes H or A;
A denotes unbranched or branched alkyl having 1-10 C atoms, in which 1-7 H atoms are each optionally replaced by Hal;
Cyc denotes cycloalkyl having 3-7 C atoms, in which 1-4 H atoms are each optionally replaced independently from one another by A, Hal or OY;

Alk denotes alkylene having 1-6 C atoms, in which 1-4 H atoms are each optionally replaced independently of one another by Hal or CN;

Ar denotes a saturated, unsaturated or aromatic, mono- or bicyclic carbocycle having 6-10 C atoms, which is unsubstituted or substituted by at least one substituent selected from $Het^3$, A, Hal, OY, COOY, -Alk-OY, -Alk-SO$_2$, -Alk-Het$^1$, —OAlk-Het$^1$, NYY, —CO—NYY, —SO$_2$NYY, and CN;

$Het^1$ denotes a monocyclic heteroaryl having 2-7 C atoms and 1-4 N, O and/or S atoms, which is unsubstituted or substituted by at least one substituent selected from A, Hal, OY, COOY, -Alk-OY, -Alk-SO$_2$, NYY, —CO—NYY, —SO$_2$NYY, and CN;

$Het^2$ denotes a bicyclic heteroaryl having 2-9 C atoms and 1-4 N atoms, which is unsubstituted or substituted by at least one substituent selected from R2, A, Hal, OY, COOY, -Alk-OY, -Alk-SO$_2$, NYY, —CO—NYY, —SO$_2$NYY, and CN;

$Het^3$ denotes a saturated monocyclic heterocycle having 2-7 C atoms and 1-4 N, O and/or S atoms, which is unsubstituted or substituted by at least one substituent selected from A, Hal, OY, COOY, -Alk-OY, -Alk-SO$_2$, NYY, —CO—NYY, —SO$_2$NYY, and CN; and Hal denotes F, Cl, Br or I;

or a physiologically acceptable salt thereof.

2. A compound according to claim 1, wherein
$W_1$ denotes N or CH,
$W_2$ denotes CR6,
$W_3$ denotes N or CR5,
$W_5$ denotes N or CH, and
$W_6$ denotes CH.

3. A compound according to claim 1, wherein
R5 denotes H, A, OA, CN, -Alk-OY, COOY, —CO—NYY, NYY, —OAlk-OY, —OAlk-NYY, —OAlk-Het$^3$, —NH—CO-Alk-NYY, Hal, —CO—NYY—NYY or —CO—NH-Alk-Het$^3$; or R1, R5 together denote —CH=CH—, —CO—NH—, —SO2-NH—, —N=C(Y)—, —CH=C(NO2)- or —CH=C(Hal)-.

4. A compound according to claim 1, wherein R6 denotes H, A, OA, NH$_2$, —NH—COA, —CO—NHA, Hal, NAA, —NH—CO-Alk-NYY, —NH-Alk-Het$^3$, —NH—CO—NH$_2$, —NH—CO-Het$^3$, —CO—NH-Het$^3$, NH—CO-Alk-OH or NH—CO-Alk-NH—COOA.

5. A compound according to claim 1, wherein R2 denotes phenyl, pyridyl, pyrazolyl or pyrazinyl, each of which is unsubstituted or mono-, di- or trisubstituted by at least one substituent selected from F, Cl, Br, CH$_3$, CF$_3$, CN, OCH$_3$, and OCF$_3$.

6. A compound according to claim 1, wherein said compound is of formula (II)

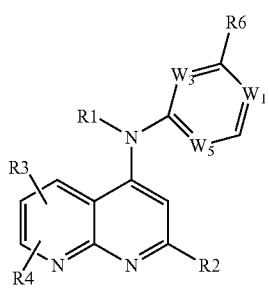

(II)

wherein
$W_1$, $W_5$ each denotes, independently from one another, N or CH;
$W_3$ denotes N or CR5;

under the proviso that at least one of $W_1$, $W_3$ or $W_5$ denotes N;

R1, R3, R4 each denotes, independently from one another, H or A;

R5 denotes H, A, OA, CN, -Alk-OY, COOY, —CO—NYY, NYY, —OAlk-OY, —OAlk-NYY, —OAlk-Het$^3$, —NH—CO-Alk-NYY, Hal, —CO—NYY—NYY or —CO—NH-Alk-Het$^3$;

R1, R5 together also denote —CH=CH—, —CO—NH—, —SO$_2$—NH—, —N=C(Y)—, —CH=C(NO$_2$)— or —CH=C(Hal)-;

R6 denotes H, A, OA, NH$_2$, —NH—COA, —CO—NHA, Hal, NAA, —NH—CO-Alk-NYY, —NH-Alk-Het$^3$, —NH—CO—NH$_2$, —NH—CO-Het$^3$, —CO—NH-Het$^3$, NH—CO-Alk-OH or NH—CO-Alk-NH—COOA;

R2 denotes phenyl, pyridyl, pyrazolyl or pyrazinyl, each of which is unsubstituted or mono-, di- or trisubstituted by at least one substituent selected from F, Cl, Br, CH$_3$, CF$_3$, CN, OCH$_3$, and OCF$_3$;

Y denotes H or A;

A denotes unbranched or branched alkyl having 1-4 C atoms, in which 1-5 H atoms are each optionally replaced by F or Cl;

Alk denotes alkylene having 1-3 C atoms;

$Het^3$ denotes piperazine, piperidine, morpholine, pyrrolidine, piperidone, morpholinone or pyrrolidone, which in each case is unsubstituted or monosubstituted by A, Hal, COOY or NYY; and Hal denotes F, Cl or Br;

or physiologically acceptable salt thereof.

7. A compound which is selected from:

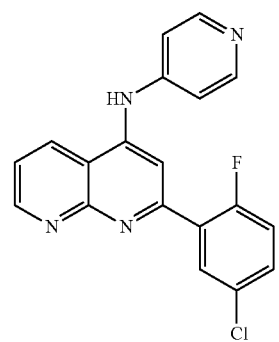

1

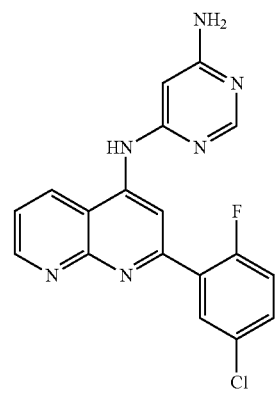

2

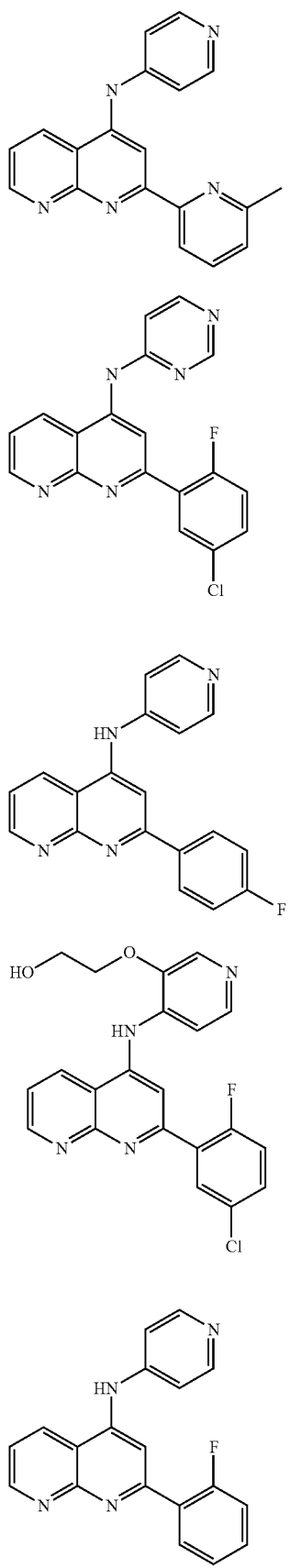
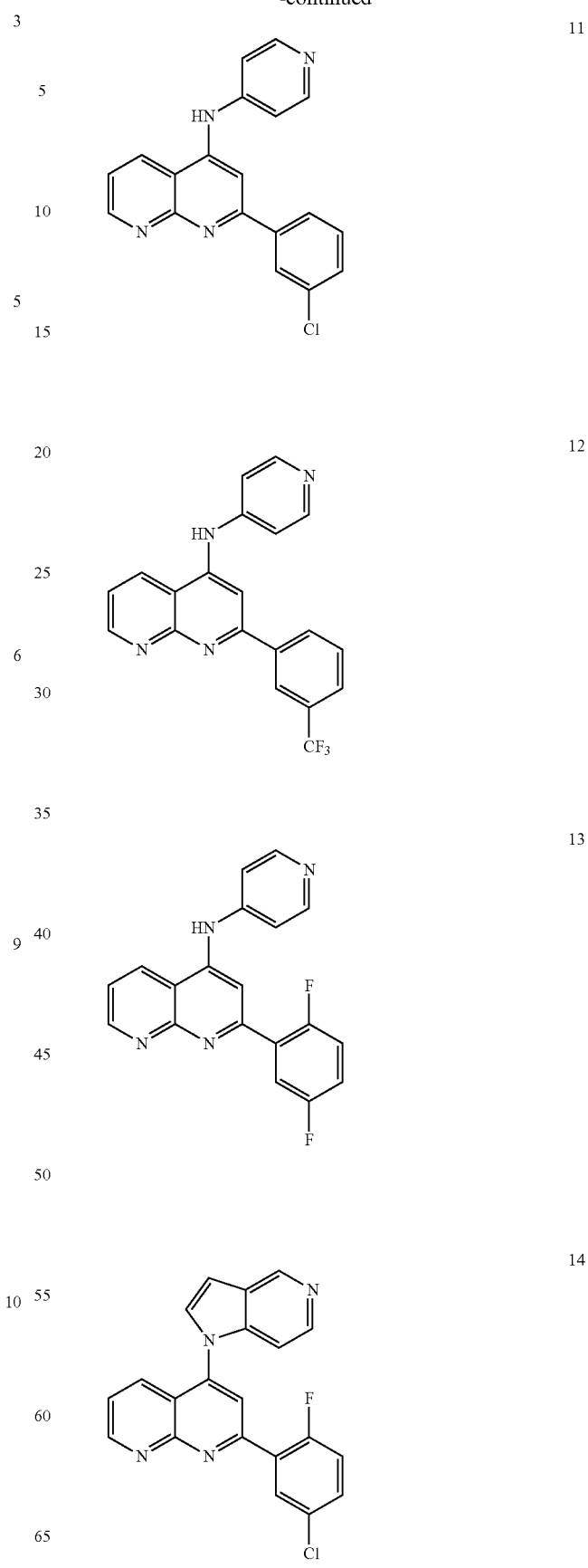

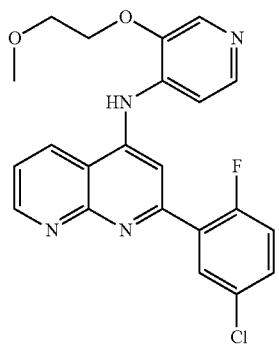
15
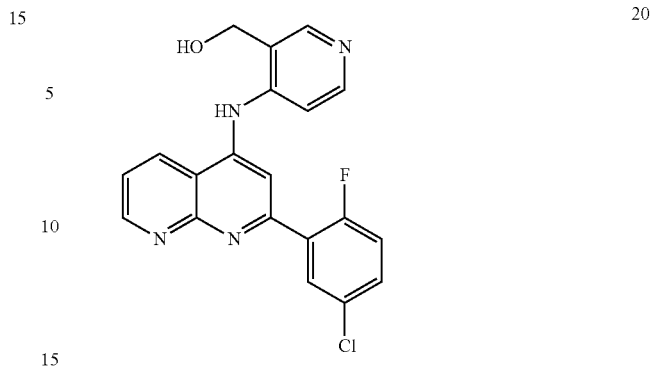
16
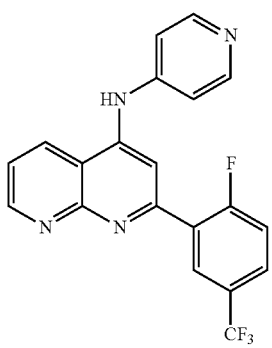
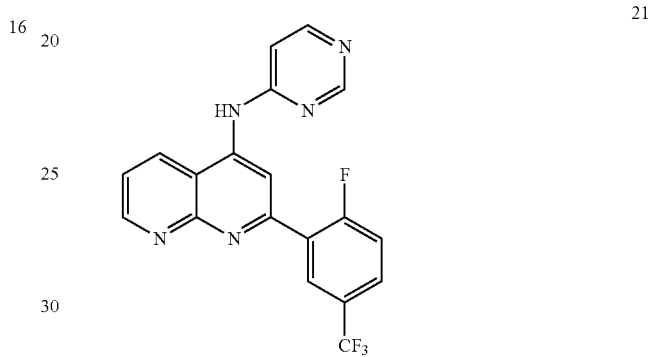
17
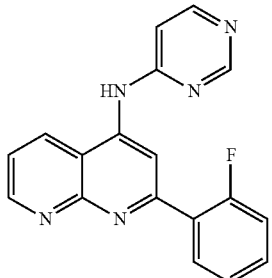
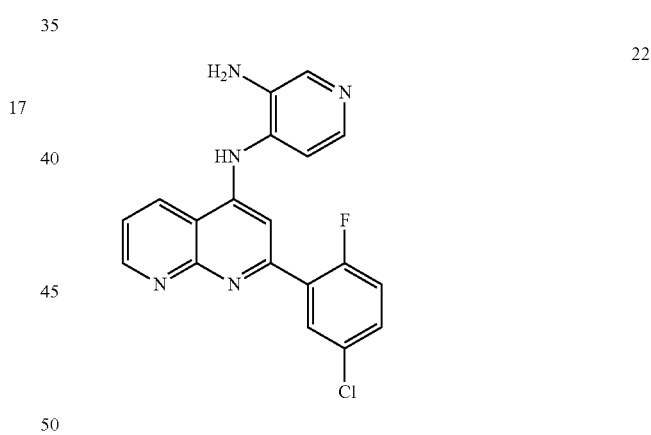
18
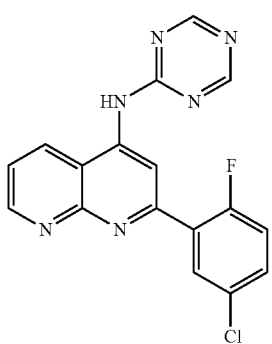
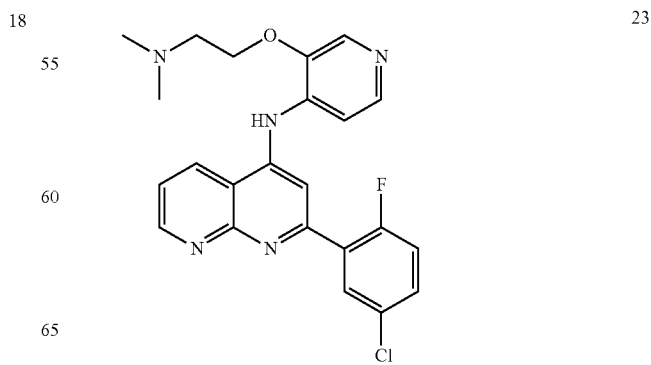

| 25 | 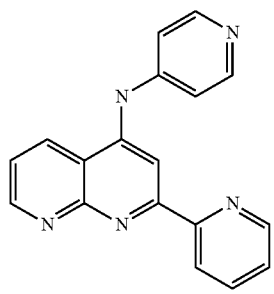 | 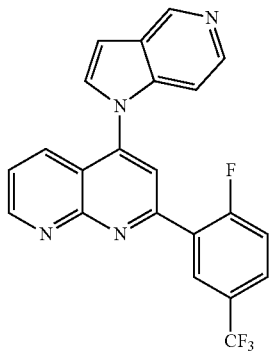 | 30 |
| 26 | 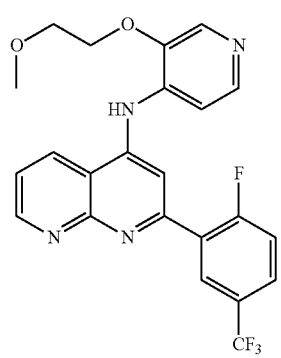 | 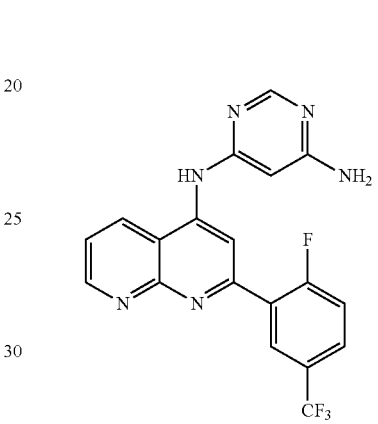 | 32 |
| 28 | 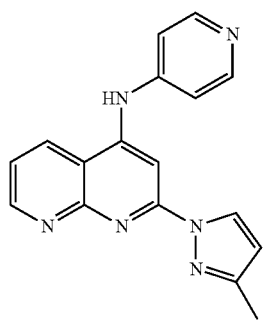 | 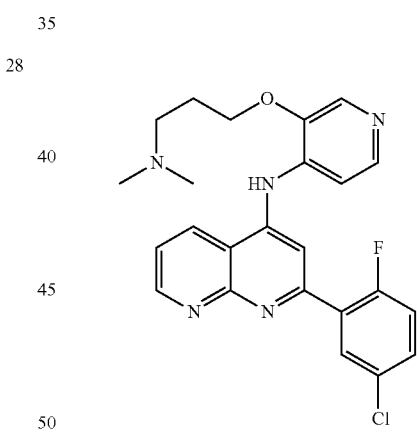 | 33 |
| 29 | 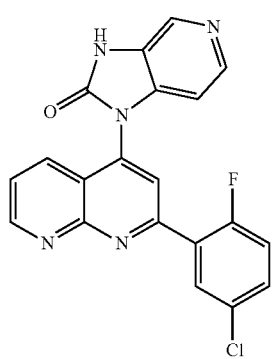 | 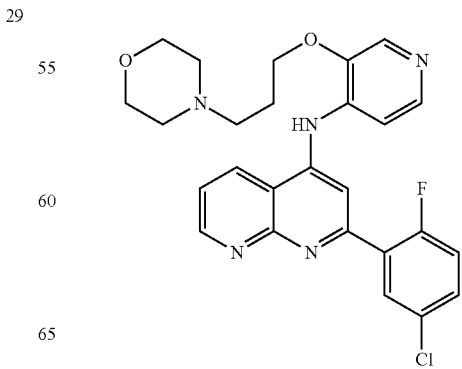 | 34 |

37
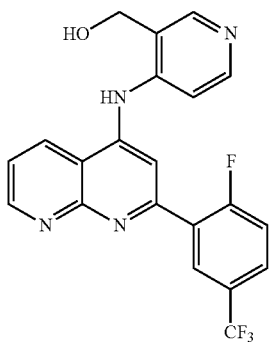
38
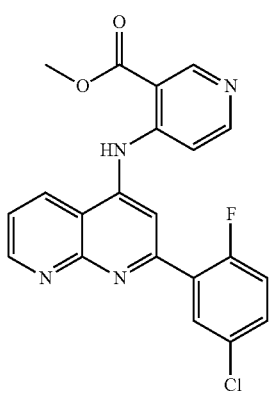
40
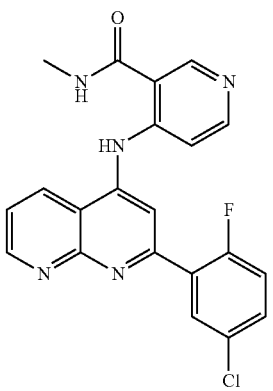
41
42
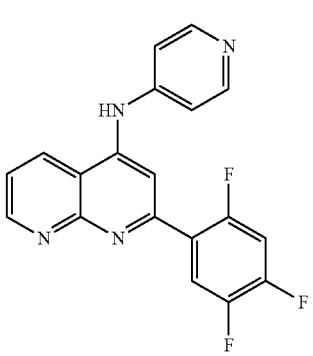
43
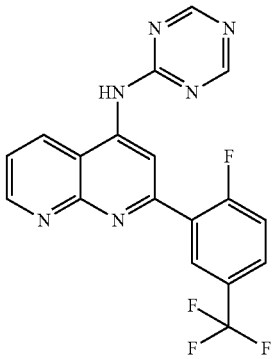
44
47
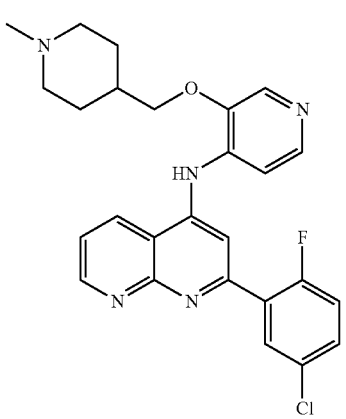

48
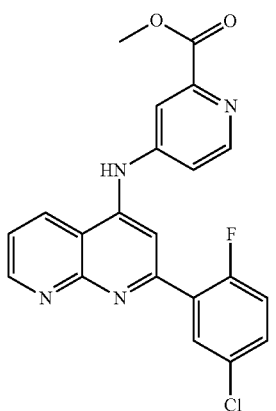
49
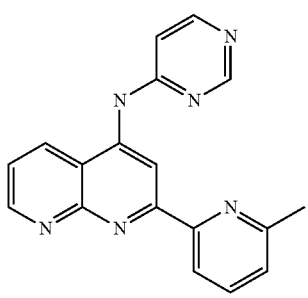
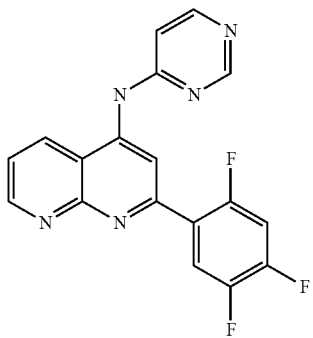
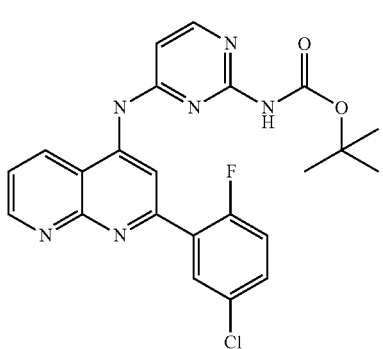
52
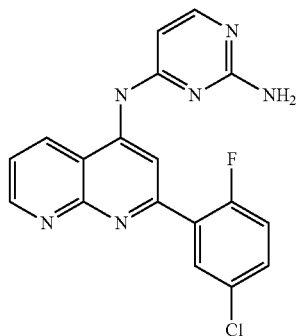
53
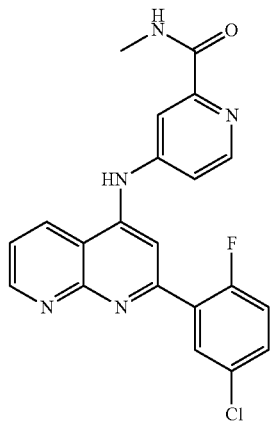
54
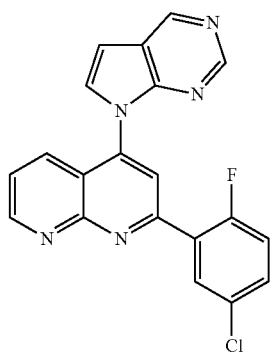
55
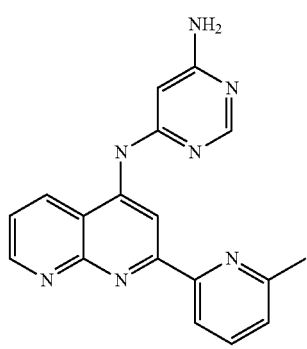

57
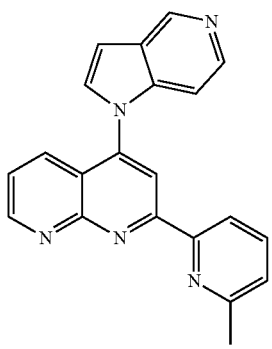
58
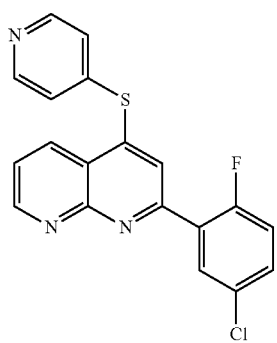
60
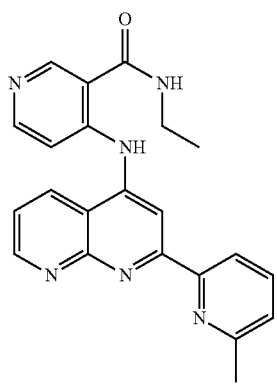
62
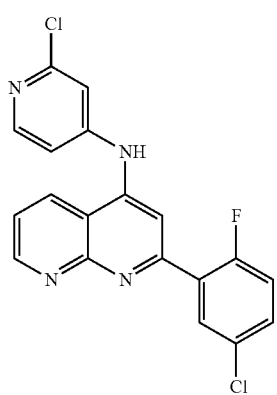
63
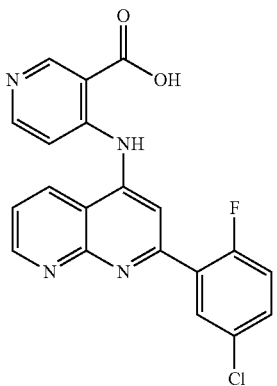
65
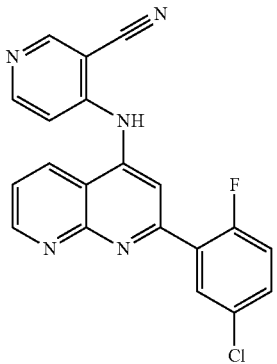
67
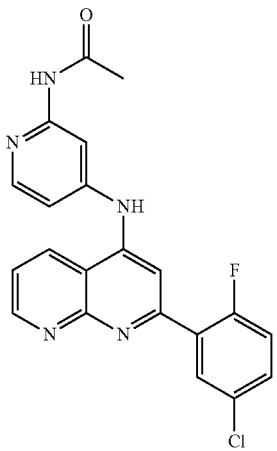
70
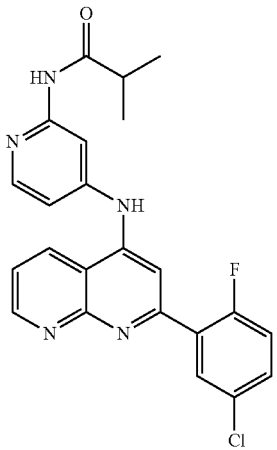

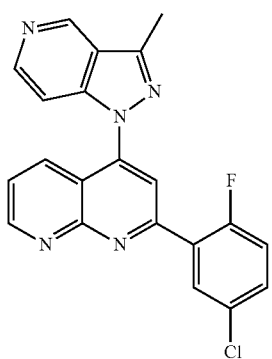
71
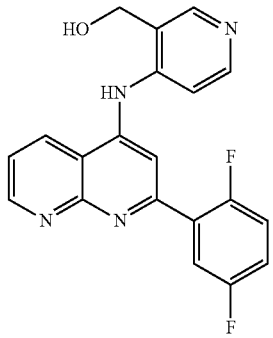
78
72
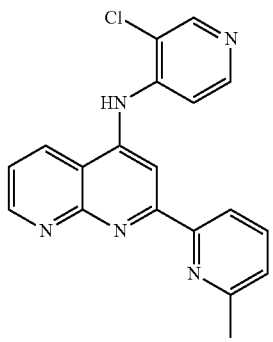
80
73
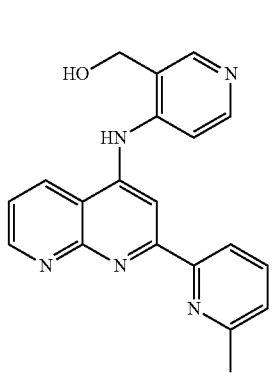
81
77
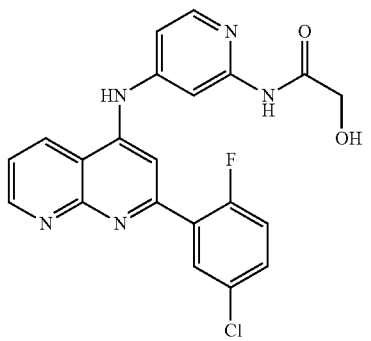
82

| | |
|---|---|
| 85 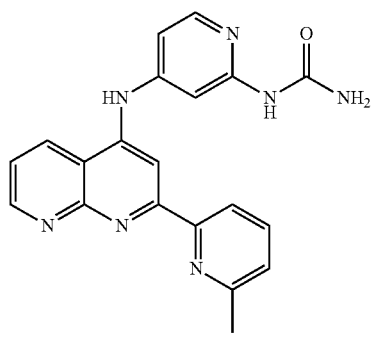 | 90 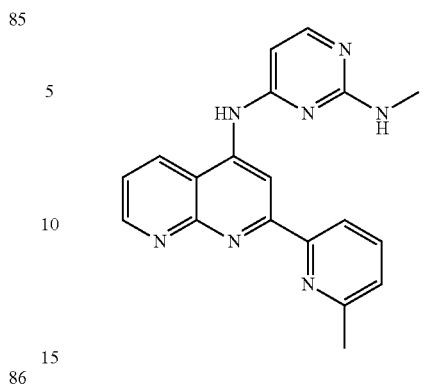 |
| 86 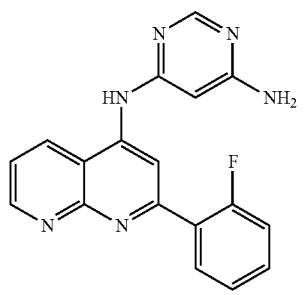 | 91 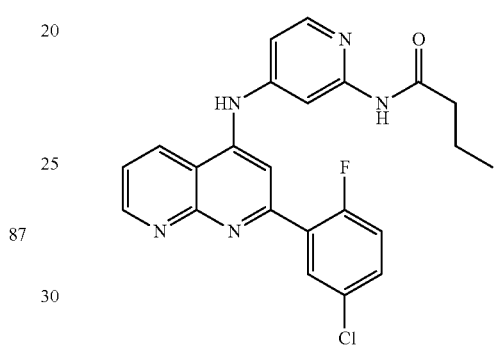 |
| 87 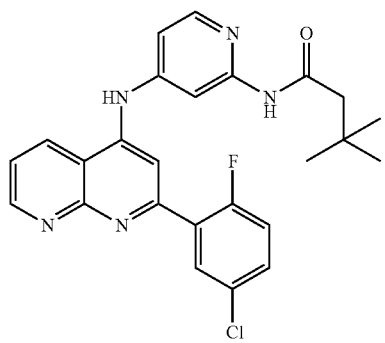 | 92 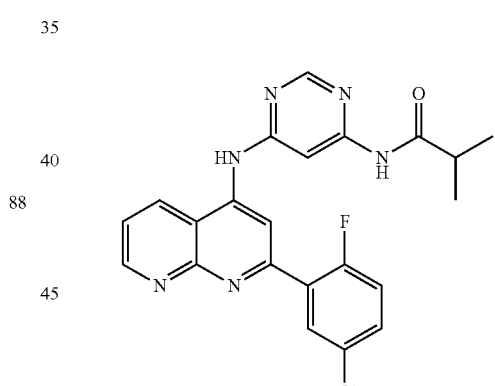 |
| 88 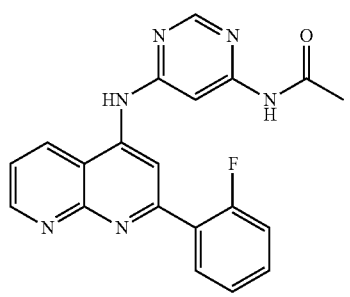 | |
| 89 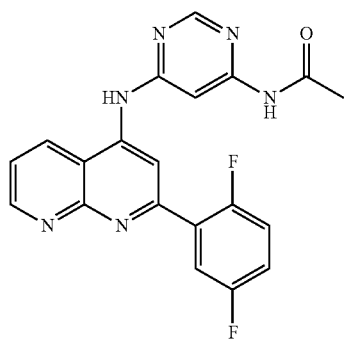 | 94 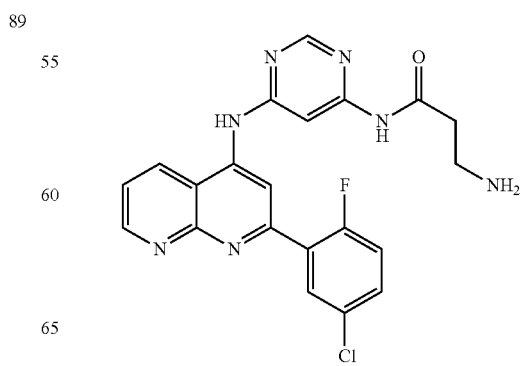 |

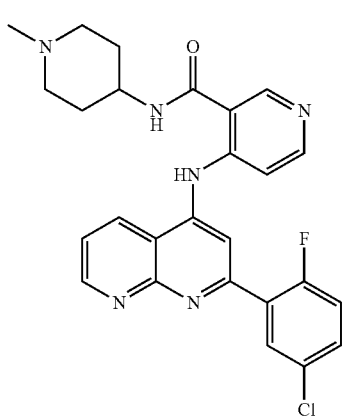
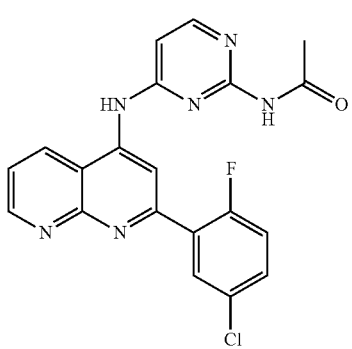
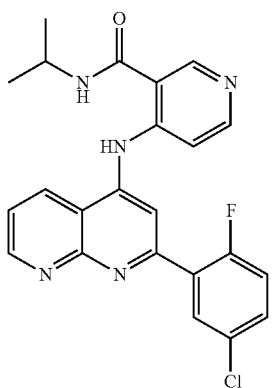
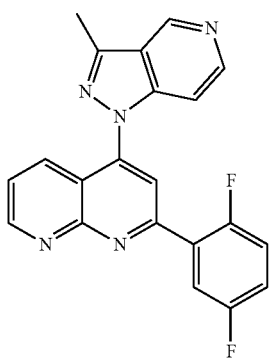
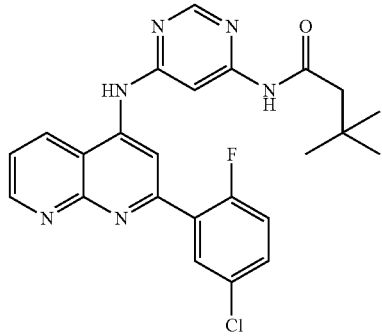
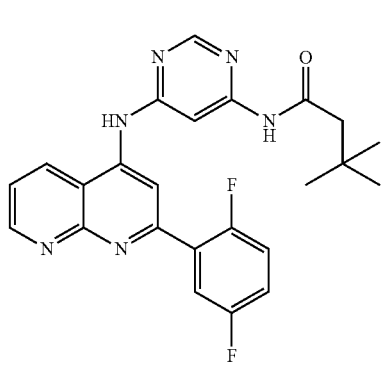
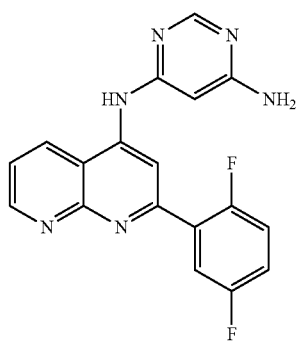
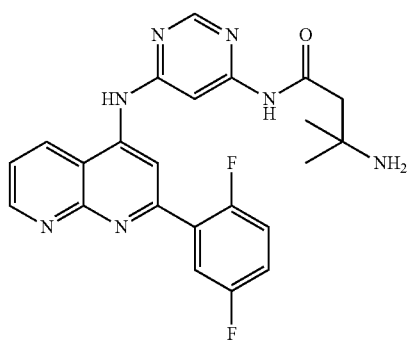

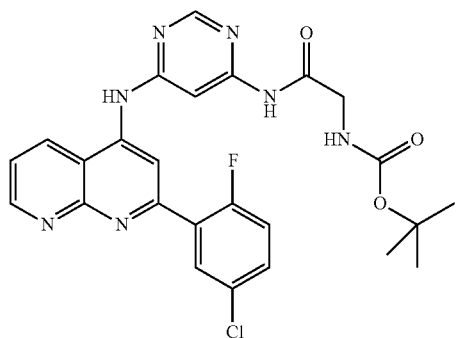
109
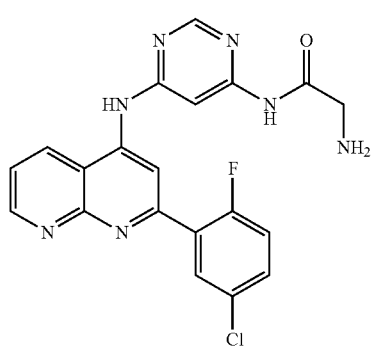
110
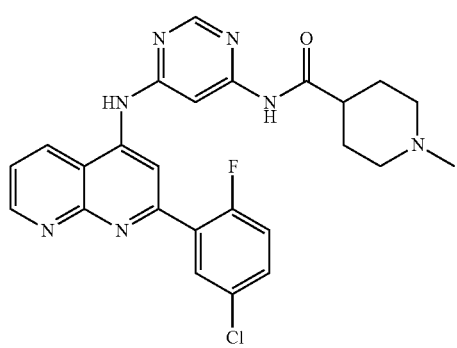
111
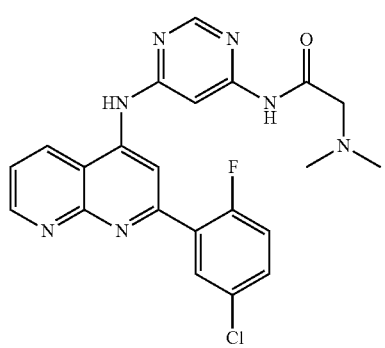
112
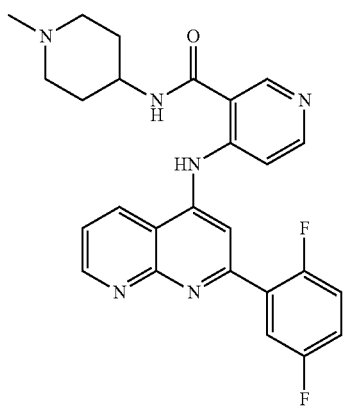
113
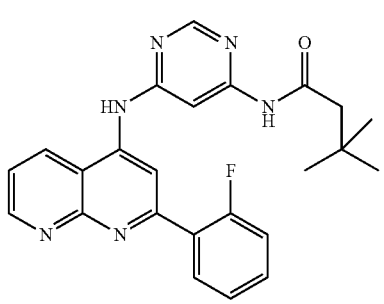
114
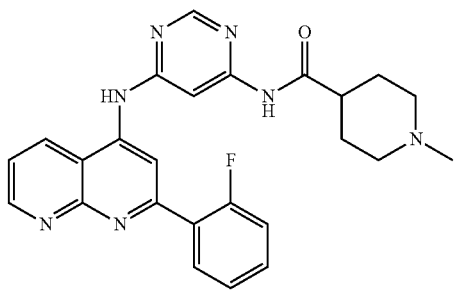
115
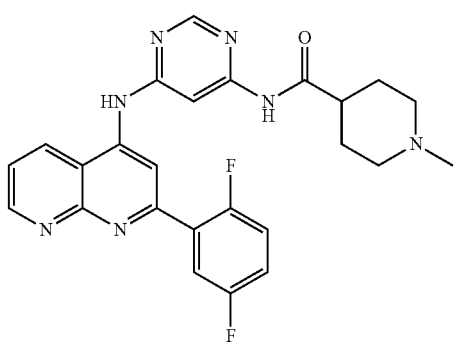
117

-continued
121 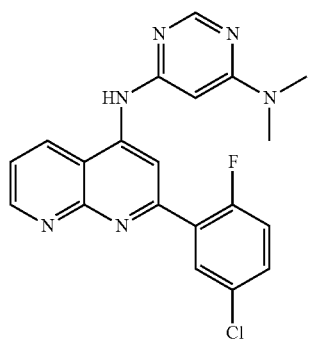
125 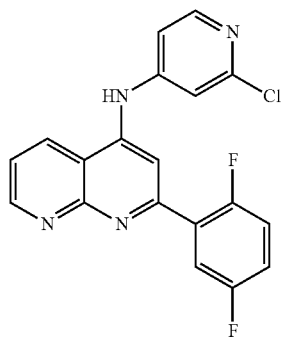
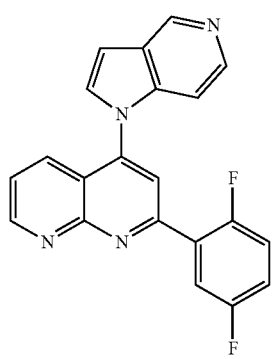
130 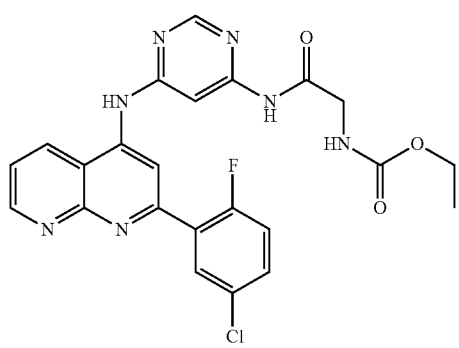
-continued
131 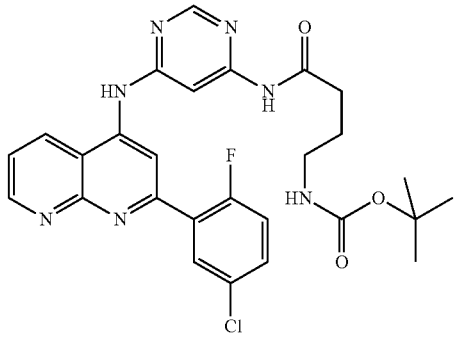
133 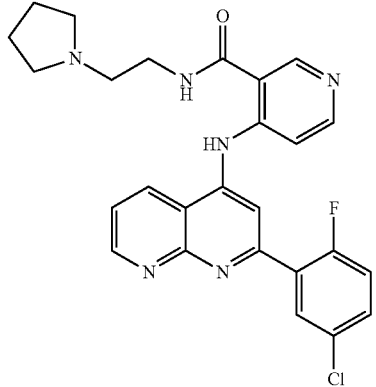
135 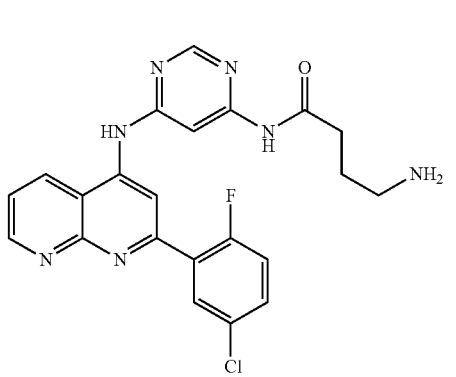
139 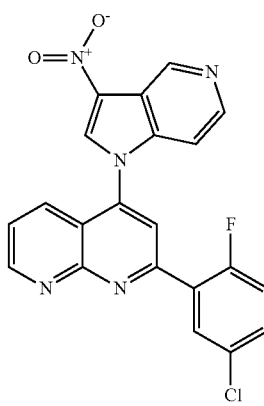

-continued

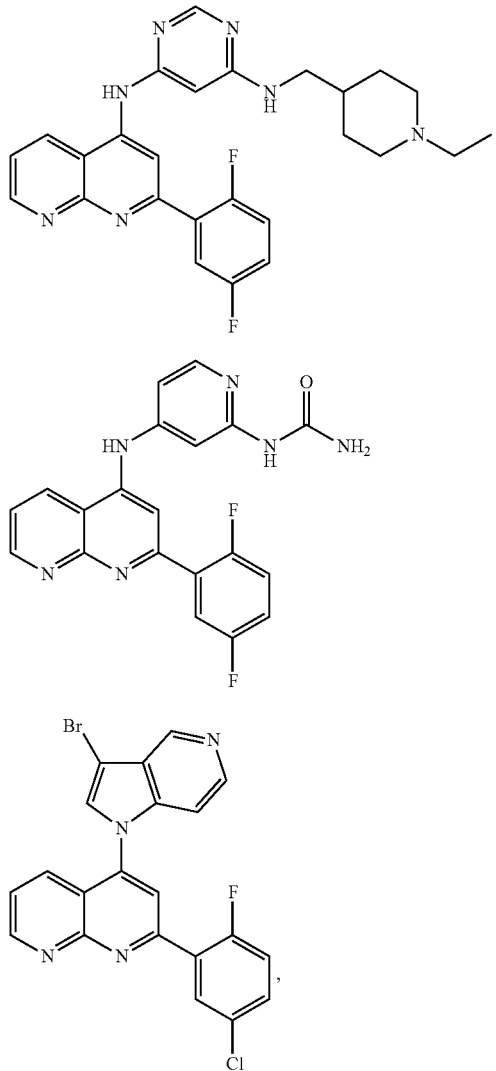

and physiologically acceptable salts thereof.

8. A process for manufacturing a compound according to claim 1, said process comprising:
(a) reacting a compound of formula (IV)

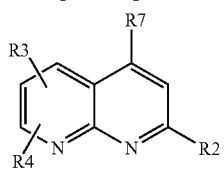

(IV)

wherein R7 denotes Hal, OY or NYY; and
R2, R3, R4, Hal and Y have the meanings as for the compound of formula (I),
with a compound of formula (V)

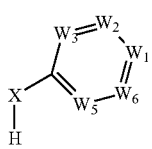

(V)

wherein X, R1, $W_1$, $W_2$, $W_3$, $W_5$ and $W_6$ have the meanings as for the compound of formula (I) under the proviso that R1, R5 together are excluded,
to yield a compound of formula (I)

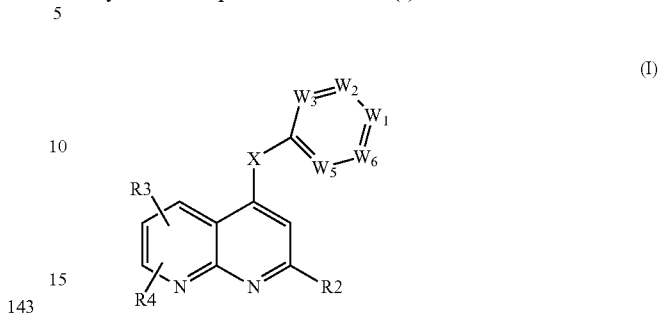

(I)

wherein X, R1, R2, R3, R4, $W_1$, $W_2$, $W_3$, $W_5$ and $W_6$ have the meanings as for the compound of formula (I) under the proviso that R1, R5 together are excluded,
and optionally
(b) converting a base or an acid of the compound of formula (I) into a salt thereof.

9. A method for inhibiting an ATP consuming protein comprising administering a compound of claim 1, wherein the IC50 of the compound amounts to less than 1 µM.

10. A pharmaceutical composition comprising as an active ingredient an effective amount of at least one compound according to claim 1 and at least one pharmaceutically tolerable adjuvants, and optionally at least other active ingredient selected from: (1) estrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors.

11. A compound according to claim 2, wherein
$W_1$ denotes N,
$W_3$ denotes CR5, and
$W_5$ denotes CH.

12. A method according to claim 9, wherein said ATP consuming protein is a TGF-beta receptor kinase.

13. A method according to claim 9, wherein said compound has an IC50 of less than 0.1 µM.

14. A compound according to claim 1, wherein in the structure

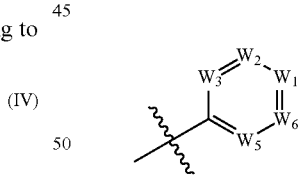

is pyridin-4-yl wherein $W_1$ is N in position 1, which is unsubstituted or is substituted by R6 in position 2 and/or substituted by R5 in position 3; and X is NR1.

15. A compound according to claim 1, wherein in the structure

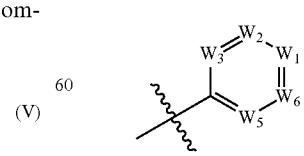

is 1,3-pyrimidin-4-yl or 1,5-pyrimidin-4-yl wherein $W_1$ is N in position 1, and either $W_3$ or $W_5$ is N, which in each case is unsubstituted or is substituted by R6 in position 2; and X is NR1.

16. A compound according to claim 1, wherein in the structure

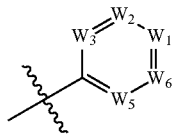

is 1,3,5-triazin-4-yl wherein $W_1$, $W_3$ and $W_5$ are N, which is unsubstituted or is substituted by R6 in position 2; and X is NR1.

17. A compound according to claim 1, wherein X denotes NR1, O or S.

18. A compound according to claim 1, wherein R2 denotes phenyl, pyrazolyl or pyrazinyl, each of which is unsubstituted or mono-, di- or trisubstituted by at least one substituent selected from F, Cl, Br, $CH_3$, $CF_3$, CN, $OCH_3$, and $OCF_3$.

19. A compound according to claim 1, wherein $W_6$ is CH.

20. A compound according to claim 1, wherein R6 denotes H, A, Hal, OY, CN, -Alk-OY, COOY, —CO—NYY, NYY, —NY—COOY, —NH-Alk-NYY, —NH—COA, —NH—CO-Alk-NYY, —NH-Het², —OAr, —NY—Ar, —OHet¹, NY-Het¹, Het¹, —NH—SO₂Y, —NH-Cyc, —NH-Het³, —NH-Alk-Het³, —NH-Alk-OY, —NH—CO—NYY, —NH—CO-Het³, —CO—NH-Het³, —NH—CO-Alk-OY, —NH—CO-Alk-Het³, —CO—NH-Alk-Het³, NH—CO-Alk-NH COOY, CO NH Alk NYY, or piperazine, piperidine, pyrrolidine, piperidone, morpholinone or pyrrolidone, each of which piperazine, piperidine, pyrrolidine, piperidone, morpholinone or pyrrolidone is unsubstituted or monosubstituted by A, Hal, COOY or NYY.

* * * * *